US012635921B2

(12) United States Patent
Al-Ali

(10) Patent No.: US 12,635,921 B2
(45) Date of Patent: **\*May 26, 2026**

(54) PHYSIOLOGICAL MEASUREMENT DEVICES, SYSTEMS, AND METHODS

(71) Applicant: MASIMO CORPORATION, Irvine, CA (US)

(72) Inventor: Ammar Al-Ali, San Juan Capistrano, CA (US)

(73) Assignee: Masimo Corporation, Irvine, CA (US)

( \* ) Notice: Subject to any disclaimer, the term of this patent is extended or adjusted under 35 U.S.C. 154(b) by 0 days.

This patent is subject to a terminal disclaimer.

(21) Appl. No.: 18/600,517

(22) Filed: Mar. 8, 2024

(65) Prior Publication Data

US 2024/0245330 A1 Jul. 25, 2024

Related U.S. Application Data

(63) Continuation of application No. 16/871,874, filed on May 11, 2020, which is a continuation of application (Continued)

(51) Int. Cl.
*A61B 5/1455* (2006.01)
*A61B 5/00* (2006.01)
(Continued)

(52) U.S. Cl.
CPC ........ *A61B 5/14552* (2013.01); *A61B 5/0002* (2013.01); *A61B 5/02416* (2013.01);
(Continued)

(58) Field of Classification Search
CPC .............. A61B 5/1455; A61B 5/14532; A61B 5/14552
See application file for complete search history.

(56) References Cited

U.S. PATENT DOCUMENTS

| | | | |
|---|---|---|---|
| 3,638,640 | A | 2/1972 | Shaw |
| 3,910,701 | A | 10/1975 | Henderson et al. |

(Continued)

FOREIGN PATENT DOCUMENTS

| | | |
|---|---|---|
| CA | 2105681 | 10/1992 |
| CA | 2137878 | 4/2007 |

(Continued)

OTHER PUBLICATIONS

Preliminary Amendment as filed with Request for Ex Parte Reexamination in Reexamination U.S. Appl. No. 90/019,457, filed Mar. 25, 2024 in 10 pages.

(Continued)

*Primary Examiner* — Marjan Fardanesh
(74) *Attorney, Agent, or Firm* — Knobbe, Martens, Olson & Bear, LLP

(57) ABSTRACT

A non-invasive, optical-based physiological monitoring system is disclosed. One embodiment includes an emitter configured to emit light. A diffuser is configured to receive and spread the emitted light, and to emit the spread light at a tissue measurement site. The system further includes a concentrator configured to receive the spread light after it has been attenuated by or reflected from the tissue measurement site. The concentrator is also configured to collect and concentrate the received light and to emit the concentrated light to a detector. The detector is configured to detect the concentrated light and to transmit a signal representative of the detected light. A processor is configured to receive the transmitted signal and to determine a physiological parameter, such as, for example, arterial oxygen saturation, in the tissue measurement site.

22 Claims, 7 Drawing Sheets

Related U.S. Application Data

No. 16/835,712, filed on Mar. 31, 2020, now Pat. No. 10,687,744, which is a continuation of application No. 16/791,955, filed on Feb. 14, 2020, now Pat. No. 10,687,743, which is a continuation of application No. 16/532,061, filed on Aug. 5, 2019, now Pat. No. 10,638,961, which is a continuation of application No. 15/195,199, filed on Jun. 28, 2016, now Pat. No. 10,448,871.

(60) Provisional application No. 62/188,430, filed on Jul. 2, 2015.

(51) Int. Cl.
  *A61B 5/024*         (2006.01)
  *A61B 5/145*         (2006.01)

(52) U.S. Cl.
  CPC ...... *A61B 5/14532* (2013.01); *A61B 5/14546* (2013.01); *A61B 5/4875* (2013.01); *A61B 5/6826* (2013.01); *A61B 5/7278* (2013.01); *A61B 5/742* (2013.01); *A61B 2562/04* (2013.01)

(56)         References Cited

U.S. PATENT DOCUMENTS

| | | | |
|---|---|---|---|
| 4,086,916 A | 5/1978 | Freeman et al. | |
| 4,120,294 A | 10/1978 | Wolfe | |
| 4,129,124 A | 12/1978 | Thalmann | |
| 4,163,447 A | 8/1979 | Orr | |
| 4,216,462 A | 8/1980 | McGrath et al. | |
| 4,224,948 A | 9/1980 | Cramer et al. | |
| 4,248,244 A | 2/1981 | Charnitski et al. | |
| 4,295,472 A | 10/1981 | Adams | |
| 4,375,219 A | 3/1983 | Schmid | |
| 4,407,290 A | 10/1983 | Wilber | |
| 4,448,199 A | 5/1984 | Schmid | |
| 4,606,352 A | 8/1986 | Geddes et al. | |
| 4,635,646 A | 1/1987 | Gilles et al. | |
| 4,880,304 A | 11/1989 | Jaeb et al. | |
| 4,960,128 A | 10/1990 | Gordon et al. | |
| 4,964,408 A | 10/1990 | Hink et al. | |
| 5,041,187 A | 8/1991 | Hink et al. | |
| 5,069,213 A | 12/1991 | Hink et al. | |
| 5,099,842 A | 3/1992 | Mannheimer et al. | |
| 5,158,091 A | 10/1992 | Butterfield et al. | |
| 5,163,438 A | 11/1992 | Gordon et al. | |
| 5,164,858 A | 11/1992 | Aguilera, Jr. et al. | |
| 5,171,085 A | 12/1992 | Jaksich | |
| 5,184,620 A | 2/1993 | Cudahy et al. | |
| 5,191,891 A | 3/1993 | Righter | |
| 5,203,329 A | 4/1993 | Takatani et al. | |
| 5,209,230 A | 5/1993 | Swedlow et al. | |
| 5,228,449 A | 7/1993 | Christ et al. | |
| 5,316,008 A | 5/1994 | Suga et al. | |
| 5,319,355 A | 6/1994 | Russek | |
| 5,337,744 A | 8/1994 | Branigan | |
| 5,341,805 A | 8/1994 | Stavridi et al. | |
| 5,351,695 A | 10/1994 | Mills et al. | |
| 5,377,676 A | 1/1995 | Vari et al. | |
| 5,413,100 A | 5/1995 | Barthelemy et al. | |
| 5,431,170 A | 7/1995 | Mathews | |
| 5,449,731 A | 9/1995 | Suzuki et al. | |
| 5,452,717 A | 9/1995 | Branigan et al. | |
| 5,456,252 A | 10/1995 | Vari et al. | |
| 5,462,051 A | 10/1995 | Oka et al. | |
| 5,479,934 A | 1/1996 | Imran | |
| 5,482,036 A | 1/1996 | Diab et al. | |
| 5,490,505 A | 2/1996 | Diab et al. | |
| 5,490,523 A | 2/1996 | Isaacson et al. | |
| 5,494,043 A | 2/1996 | O'Sullivan et al. | |
| 5,497,771 A | 3/1996 | Rosenheimer | |
| 5,533,511 A | 7/1996 | Kaspari et al. | |
| 5,534,851 A | 7/1996 | Russek | |
| 5,564,429 A | 10/1996 | Bornn et al. | |
| 5,584,296 A | 12/1996 | Cui et al. | |
| 5,590,649 A | 1/1997 | Caro et al. | |
| 5,601,079 A | 2/1997 | Wong et al. | |
| 5,602,924 A | 2/1997 | Durand et al. | |
| 5,623,925 A | 4/1997 | Swenson et al. | |
| 5,623,926 A | 4/1997 | Weiss | |
| 5,632,272 A | 5/1997 | Diab et al. | |
| 5,638,816 A | 6/1997 | Kiani-Azarbayjany et al. | |
| 5,638,818 A | 6/1997 | Diab et al. | |
| 5,645,440 A | 7/1997 | Tobler et al. | |
| 5,663,264 A | 9/1997 | Kawai et al. | |
| 5,685,299 A | 11/1997 | Diab et al. | |
| 5,699,808 A | 12/1997 | John | |
| 5,720,284 A | 2/1998 | Aoyagi et al. | |
| 5,729,203 A | 3/1998 | Oka et al. | |
| D393,830 S | 4/1998 | Tobler et al. | |
| 5,738,104 A | 4/1998 | Lo et al. | |
| 5,743,262 A | 4/1998 | Lepper, Jr. et al. | |
| 5,758,644 A | 6/1998 | Diab et al. | |
| 5,760,910 A | 6/1998 | Lepper, Jr. et al. | |
| 5,769,785 A | 6/1998 | Diab et al. | |
| 5,782,756 A | 7/1998 | Mannheimer | |
| 5,782,757 A | 7/1998 | Diab et al. | |
| 5,785,659 A | 7/1998 | Caro et al. | |
| 5,791,347 A | 8/1998 | Flaherty et al. | |
| 5,792,052 A | 8/1998 | Isaacson et al. | |
| 5,800,349 A | 9/1998 | Isaacson et al. | |
| 5,810,734 A | 9/1998 | Caro et al. | |
| 5,823,950 A | 10/1998 | Diab et al. | |
| 5,830,131 A | 11/1998 | Caro et al. | |
| 5,830,137 A | 11/1998 | Scharf | |
| 5,833,618 A | 11/1998 | Caro et al. | |
| 5,860,919 A | 1/1999 | Kiani-Azarbayjany et al. | |
| 5,890,929 A | 4/1999 | Mills et al. | |
| 5,893,364 A | 4/1999 | Haar et al. | |
| 5,904,654 A | 5/1999 | Wohltmann et al. | |
| 5,919,134 A | 7/1999 | Diab | |
| 5,934,925 A | 8/1999 | Tobler et al. | |
| 5,940,182 A | 8/1999 | Lepper, Jr. et al. | |
| 5,952,084 A | 9/1999 | Anderson et al. | |
| 5,983,122 A | 11/1999 | Jarman et al. | |
| 5,987,343 A | 11/1999 | Kinast | |
| 5,995,855 A | 11/1999 | Kiani et al. | |
| 5,997,343 A | 12/1999 | Mills et al. | |
| 6,002,952 A | 12/1999 | Diab et al. | |
| 6,011,986 A | 1/2000 | Diab et al. | |
| 6,014,576 A | 1/2000 | Raley | |
| 6,027,452 A | 2/2000 | Flaherty et al. | |
| 6,036,642 A | 3/2000 | Diab et al. | |
| 6,045,509 A | 4/2000 | Caro et al. | |
| 6,067,462 A | 5/2000 | Diab et al. | |
| 6,069,653 A | 5/2000 | Hudson | |
| 6,075,755 A | 6/2000 | Zarchan | |
| 6,081,735 A | 6/2000 | Diab et al. | |
| 6,083,156 A | 7/2000 | Lisicck | |
| 6,088,607 A | 7/2000 | Diab et al. | |
| 6,091,530 A | 7/2000 | Duckworth | |
| 6,102,856 A | 8/2000 | Groff et al. | |
| 6,110,522 A | 8/2000 | Lepper, Jr. et al. | |
| 6,115,621 A | 9/2000 | Chin | |
| 6,124,597 A | 9/2000 | Shehada et al. | |
| 6,128,521 A | 10/2000 | Marro et al. | |
| 6,129,675 A | 10/2000 | Jay | |
| 6,144,868 A | 11/2000 | Parker | |
| 6,151,516 A | 11/2000 | Kiani-Azarbayjany et al. | |
| 6,152,754 A | 11/2000 | Gerhardt et al. | |
| 6,157,850 A | 12/2000 | Diab et al. | |
| 6,158,245 A | 12/2000 | Savant | |
| 6,165,005 A | 12/2000 | Mills et al. | |
| 6,184,521 B1 | 2/2001 | Coffin, IV et al. | |
| 6,206,830 B1 | 3/2001 | Diab et al. | |
| 6,223,063 B1 | 4/2001 | Chaiken et al. | |
| 6,229,856 B1 | 5/2001 | Diab et al. | |
| 6,232,609 B1 | 5/2001 | Snyder et al. | |
| 6,236,872 B1 | 5/2001 | Diab et al. | |
| 6,241,680 B1 | 6/2001 | Miwa | |
| 6,241,683 B1 | 6/2001 | Macklem et al. | |

(56)        References Cited

U.S. PATENT DOCUMENTS

| | | | |
|---|---|---|---|
| 6,253,097 | B1 | 6/2001 | Aronow et al. |
| 6,256,523 | B1 | 7/2001 | Diab et al. |
| 6,263,222 | B1 | 7/2001 | Diab et al. |
| 6,265,789 | B1 | 7/2001 | Honda et al. |
| 6,278,522 | B1 | 8/2001 | Lepper, Jr. et al. |
| 6,278,889 | B1 | 8/2001 | Robinson |
| 6,280,213 | B1 | 8/2001 | Tobler et al. |
| 6,285,896 | B1 | 9/2001 | Tobler et al. |
| 6,301,493 | B1 | 10/2001 | Marro et al. |
| 6,308,089 | B1 | 10/2001 | von der Ruhr et al. |
| 6,317,627 | B1 | 11/2001 | Ennen et al. |
| 6,321,100 | B1 | 11/2001 | Parker |
| 6,325,761 | B1 | 12/2001 | Jay |
| 6,331,063 | B1 | 12/2001 | Kamada et al. |
| 6,334,065 | B1 | 12/2001 | Al-Ali et al. |
| 6,343,223 | B1 | 1/2002 | Chin et al. |
| 6,343,224 | B1 | 1/2002 | Parker |
| 6,349,228 | B1 | 2/2002 | Kiani et al. |
| 6,356,203 | B1 | 3/2002 | Halleck et al. |
| 6,360,114 | B1 | 3/2002 | Diab et al. |
| 6,368,283 | B1 | 4/2002 | Xu et al. |
| 6,371,921 | B1 | 4/2002 | Caro et al. |
| 6,377,829 | B1 | 4/2002 | Al-Ali |
| 6,388,240 | B2 | 5/2002 | Schulz et al. |
| 6,397,091 | B2 | 5/2002 | Diab et al. |
| 6,398,727 | B1 | 6/2002 | Bui et al. |
| 6,430,437 | B1 | 8/2002 | Marro |
| 6,430,525 | B1 | 8/2002 | Weber et al. |
| 6,434,421 | B1 | 8/2002 | Taheri |
| 6,463,311 | B1 | 10/2002 | Diab |
| 6,470,199 | B1 | 10/2002 | Kopotic et al. |
| 6,483,976 | B2 | 11/2002 | Shie et al. |
| 6,501,975 | B2 | 12/2002 | Diab et al. |
| 6,505,059 | B1 | 1/2003 | Kollias et al. |
| 6,515,273 | B2 | 2/2003 | Al-Ali |
| 6,519,487 | B1 | 2/2003 | Parker |
| 6,522,915 | B1 | 2/2003 | Ceballos et al. |
| 6,525,386 | B1 | 2/2003 | Mills et al. |
| 6,526,300 | B1 | 2/2003 | Kiani et al. |
| 6,541,756 | B2 | 4/2003 | Schulz et al. |
| 6,542,764 | B1 | 4/2003 | Al-Ali et al. |
| 6,580,086 | B1 | 6/2003 | Schulz et al. |
| 6,584,336 | B1 | 6/2003 | Ali et al. |
| 6,594,513 | B1 | 7/2003 | Jobsis et al. |
| 6,597,932 | B2 | 7/2003 | Tian et al. |
| 6,597,933 | B2 | 7/2003 | Kiani et al. |
| 6,606,511 | B1 | 8/2003 | Ali et al. |
| 6,608,562 | B1 | 8/2003 | Kimura et al. |
| 6,632,181 | B2 | 10/2003 | Flaherty et al. |
| 6,639,668 | B1 | 10/2003 | Trepagnier |
| 6,640,116 | B2 | 10/2003 | Diab |
| 6,643,530 | B2 | 11/2003 | Diab et al. |
| 6,650,917 | B2 | 11/2003 | Diab et al. |
| 6,654,624 | B2 | 11/2003 | Diab et al. |
| 6,658,276 | B2 | 12/2003 | Kiani et al. |
| 6,661,161 | B1 | 12/2003 | Lanzo et al. |
| 6,671,526 | B1 | 12/2003 | Aoyagi et al. |
| 6,671,531 | B2 | 12/2003 | Al-Ali |
| 6,678,543 | B2 | 1/2004 | Diab et al. |
| 6,684,090 | B2 | 1/2004 | Ali et al. |
| 6,684,091 | B2 | 1/2004 | Parker |
| 6,697,656 | B1 | 2/2004 | Al-Ali |
| 6,697,657 | B1 | 2/2004 | Shehada et al. |
| 6,697,658 | B2 | 2/2004 | Al-Ali |
| RE38,476 | E | 3/2004 | Diab et al. |
| 6,699,194 | B1 | 3/2004 | Diab et al. |
| 6,707,476 | B1 | 3/2004 | Hochstedler |
| 6,714,804 | B2 | 3/2004 | Al-Ali et al. |
| RE38,492 | E | 4/2004 | Diab et al. |
| 6,721,582 | B2 | 4/2004 | Trepagnier et al. |
| 6,721,585 | B1 | 4/2004 | Parker |
| 6,725,075 | B2 | 4/2004 | Al-Ali |
| 6,728,560 | B2 | 4/2004 | Kollias et al. |
| 6,735,459 | B2 | 5/2004 | Parker |
| 6,745,060 | B2 | 6/2004 | Diab et al. |
| 6,760,607 | B2 | 7/2004 | Al-Ali |
| 6,770,028 | B1 | 8/2004 | Ali et al. |
| 6,771,994 | B2 | 8/2004 | Kiani et al. |
| 6,775,566 | B2 | 8/2004 | Nissilä |
| 6,785,568 | B2 | 8/2004 | Chance |
| 6,792,300 | B1 | 9/2004 | Diab et al. |
| 6,801,799 | B2 | 10/2004 | Mendelson |
| 6,813,511 | B2 | 11/2004 | Diab et al. |
| 6,815,694 | B2 | 11/2004 | Sfez et al. |
| 6,816,241 | B2 | 11/2004 | Grubisic |
| 6,816,741 | B2 | 11/2004 | Diab |
| 6,822,564 | B2 | 11/2004 | Al-Ali |
| 6,826,419 | B2 | 11/2004 | Diab et al. |
| 6,830,711 | B2 | 12/2004 | Mills et al. |
| 6,831,266 | B2 | 12/2004 | Paritsky et al. |
| 6,835,535 | B2 | 12/2004 | Gretton et al. |
| 6,847,836 | B1 | 1/2005 | Sujdak |
| 6,850,787 | B2 | 2/2005 | Weber et al. |
| 6,850,788 | B2 | 2/2005 | Al-Ali |
| 6,852,083 | B2 | 2/2005 | Caro et al. |
| 6,859,326 | B2 | 2/2005 | Sales |
| 6,861,639 | B2 | 3/2005 | Al-Ali |
| 6,898,452 | B2 | 5/2005 | Al-Ali et al. |
| 6,920,345 | B2 | 7/2005 | Al-Ali et al. |
| 6,931,268 | B1 | 8/2005 | Kiani-Azarbayjany et al. |
| 6,934,570 | B2 | 8/2005 | Kiani et al. |
| 6,939,305 | B2 | 9/2005 | Flaherty et al. |
| 6,943,348 | B1 | 9/2005 | Coffin IV |
| 6,950,687 | B2 | 9/2005 | Al-Ali |
| 6,961,598 | B2 | 11/2005 | Diab |
| 6,970,792 | B1 | 11/2005 | Diab |
| 6,979,812 | B2 | 12/2005 | Al-Ali |
| 6,982,930 | B1 | 1/2006 | Hung |
| 6,985,764 | B2 | 1/2006 | Mason et al. |
| 6,993,371 | B2 | 1/2006 | Kiani et al. |
| 6,996,427 | B2 | 2/2006 | Ali et al. |
| 6,999,904 | B2 | 2/2006 | Weber et al. |
| 7,003,338 | B2 | 2/2006 | Weber et al. |
| 7,003,339 | B2 | 2/2006 | Diab et al. |
| 7,008,380 | B1 | 3/2006 | Rees et al. |
| 7,015,451 | B2 | 3/2006 | Dalke et al. |
| 7,024,233 | B2 | 4/2006 | Ali et al. |
| 7,027,849 | B2 | 4/2006 | Al-Ali |
| 7,030,749 | B2 | 4/2006 | Al-Ali |
| 7,033,736 | B2 | 4/2006 | Morris et al. |
| 7,039,449 | B2 | 5/2006 | Al-Ali |
| 7,041,060 | B2 | 5/2006 | Flaherty et al. |
| 7,044,918 | B2 | 5/2006 | Diab |
| 7,048,687 | B1 | 5/2006 | Reuss et al. |
| 7,060,963 | B2 | 6/2006 | Maegawa et al. |
| 7,067,893 | B2 | 6/2006 | Mills et al. |
| 7,096,052 | B2 | 8/2006 | Mason et al. |
| 7,096,054 | B2 | 8/2006 | Abdul-Hafiz et al. |
| 7,132,641 | B2 | 11/2006 | Schulz et al. |
| 7,142,901 | B2 | 11/2006 | Kiani et al. |
| 7,149,561 | B2 | 12/2006 | Diab |
| 7,186,966 | B2 | 3/2007 | Al-Ali |
| 7,190,261 | B2 | 3/2007 | Al-Ali |
| 7,190,986 | B1 | 3/2007 | Hannula et al. |
| 7,215,984 | B2 | 5/2007 | Diab et al. |
| 7,215,986 | B2 | 5/2007 | Diab et al. |
| 7,221,971 | B2 | 5/2007 | Diab et al. |
| 7,225,006 | B2 | 5/2007 | Al-Ali et al. |
| 7,225,007 | B2 | 5/2007 | Al-Ali et al. |
| RE39,672 | E | 6/2007 | Shehada et al. |
| 7,227,156 | B2 | 6/2007 | Colvin, Jr. et al. |
| 7,239,905 | B2 | 7/2007 | Kiani-Azarbayjany et al. |
| 7,245,953 | B1 | 7/2007 | Parker |
| 7,254,429 | B2 | 8/2007 | Schurman et al. |
| 7,254,431 | B2 | 8/2007 | Al-Ali et al. |
| 7,254,433 | B2 | 8/2007 | Diab et al. |
| 7,254,434 | B2 | 8/2007 | Schulz et al. |
| 7,272,425 | B2 | 9/2007 | Al-Ali |
| 7,274,955 | B2 | 9/2007 | Kiani et al. |
| D554,263 | S | 10/2007 | Al-Ali et al. |
| 7,280,858 | B2 | 10/2007 | Al-Ali et al. |
| 7,289,835 | B2 | 10/2007 | Mansfield et al. |
| 7,292,883 | B2 | 11/2007 | De Felice et al. |
| 7,295,866 | B2 | 11/2007 | Al-Ali |

(56)           References Cited

U.S. PATENT DOCUMENTS

| | | | |
|---|---|---|---|
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| 7,349,726 B2 | 3/2008 | Casciani et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al-Ali et al. |
| 7,377,899 B2 | 5/2008 | Weber et al. |
| 7,383,070 B2 | 6/2008 | Diab et al. |
| 7,385,874 B2 | 6/2008 | Vuilleumier et al. |
| 7,399,277 B2 | 7/2008 | Saidara et al. |
| 7,415,297 B2 | 8/2008 | Al-Ali et al. |
| 7,415,298 B2 | 8/2008 | Casciani et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,455,423 B2 | 11/2008 | Takenaka |
| 7,467,002 B2 | 12/2008 | Weber et al. |
| 7,468,036 B1 | 12/2008 | Rulkov et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,502,643 B2 | 3/2009 | Farringdon et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,519,327 B2 | 4/2009 | White |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,596,398 B2 | 9/2009 | Al-Ali et al. |
| 7,601,123 B2 | 10/2009 | Tweed et al. |
| 7,613,490 B2 | 11/2009 | Sarussi et al. |
| 7,618,375 B2 | 11/2009 | Flaherty et al. |
| 7,620,212 B1 | 11/2009 | Allen et al. |
| D606,659 S | 12/2009 | Kiani et al. |
| D608,225 S | 1/2010 | Giroud |
| 7,647,083 B2 | 1/2010 | Al-Ali et al. |
| 7,650,176 B2 | 1/2010 | Sarussi et al. |
| D609,193 S | 2/2010 | Al-Ali et al. |
| 7,682,070 B2 | 3/2010 | Burton |
| D614,305 S | 4/2010 | Al-Ali et al. |
| RE41,317 E | 5/2010 | Parker |
| 7,726,209 B2 | 6/2010 | Ruotoistenmäki |
| 7,729,733 B2 | 6/2010 | Al-Ali et al. |
| 7,734,320 B2 | 6/2010 | Al-Ali |
| 7,740,588 B1 | 6/2010 | Sciarra |
| 7,740,589 B2 | 6/2010 | Maschke et al. |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D620,884 S | 8/2010 | Lee et al. |
| D621,516 S | 8/2010 | Kiani et al. |
| 7,791,155 B2 | 9/2010 | Diab |
| 7,801,581 B2 | 9/2010 | Diab |
| D626,147 S | 10/2010 | Goddard |
| 7,822,452 B2 | 10/2010 | Schurman et al. |
| RE41,912 E | 11/2010 | Parker |
| D628,110 S | 11/2010 | Boulangeot |
| 7,844,313 B2 | 11/2010 | Kiani et al. |
| 7,844,314 B2 | 11/2010 | Al-Ali |
| 7,844,315 B2 | 11/2010 | Al-Ali |
| D630,961 S | 1/2011 | Ciuchindel et al. |
| 7,862,523 B2 | 1/2011 | Ruotoistenmaki |
| 7,865,222 B2 | 1/2011 | Weber et al. |
| 7,869,849 B2 | 1/2011 | Ollerdessen et al. |
| 7,873,497 B2 | 1/2011 | Weber et al. |
| 7,876,274 B2 | 1/2011 | Hobson et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,510 B2 | 3/2011 | Hoarau |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,946,758 B2 | 5/2011 | Mooring |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,978,062 B2 | 7/2011 | LaLonde et al. |
| 7,988,637 B2 | 8/2011 | Diab |
| 7,990,382 B2 | 8/2011 | Kiani |
| 7,991,446 B2 | 8/2011 | Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| D645,818 S | 9/2011 | Guccione et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,727 B2 | 10/2011 | Schurman et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| 8,071,935 B2 | 12/2011 | Besko et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,162,804 B2 | 4/2012 | Tagliabue |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,533 B2 | 7/2012 | Diab et al. |
| 8,229,535 B2 | 7/2012 | Mensinger et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |

(56)        References Cited

U.S. PATENT DOCUMENTS

| | | | |
|---|---|---|---|
| 8,265,723 | B1 | 9/2012 | McHale et al. |
| 8,274,360 | B2 | 9/2012 | Sampath et al. |
| 8,280,469 | B2 | 10/2012 | Baker, Jr. et al. |
| 8,280,473 | B2 | 10/2012 | Al-Ali |
| 8,289,130 | B2 | 10/2012 | Nakajima et al. |
| 8,301,217 | B2 | 10/2012 | Al-Ali et al. |
| 8,306,596 | B2 | 11/2012 | Schurman et al. |
| 8,310,336 | B2 | 11/2012 | Muhsin et al. |
| 8,311,514 | B2 | 11/2012 | Bandyopadhyay et al. |
| 8,315,683 | B2 | 11/2012 | Al-Ali et al. |
| RE43,860 | E | 12/2012 | Parker |
| 8,337,403 | B2 | 12/2012 | Al-Ali et al. |
| 8,346,330 | B2 | 1/2013 | Lamego |
| 8,353,842 | B2 | 1/2013 | Al-Ali et al. |
| 8,355,766 | B2 | 1/2013 | MacNeish, III et al. |
| 8,359,080 | B2 | 1/2013 | Diab et al. |
| 8,364,223 | B2 | 1/2013 | Al-Ali et al. |
| 8,364,226 | B2 | 1/2013 | Diab et al. |
| 8,364,389 | B2 | 1/2013 | Dorogusker et al. |
| 8,374,665 | B2 | 2/2013 | Lamego |
| 8,385,995 | B2 | 2/2013 | Al-Ali et al. |
| 8,385,996 | B2 | 2/2013 | Smith et al. |
| 8,388,353 | B2 | 3/2013 | Kiani et al. |
| 8,399,822 | B2 | 3/2013 | Al-Ali |
| 8,401,602 | B2 | 3/2013 | Kiani |
| 8,405,608 | B2 | 3/2013 | Al-Ali et al. |
| 8,414,499 | B2 | 4/2013 | Al-Ali et al. |
| 8,418,524 | B2 | 4/2013 | Al-Ali |
| 8,423,106 | B2 | 4/2013 | Lamego et al. |
| 8,428,967 | B2 | 4/2013 | Olsen et al. |
| 8,430,817 | B1 | 4/2013 | Al-Ali et al. |
| 8,437,825 | B2 | 5/2013 | Dalvi et al. |
| 8,446,275 | B2 | 5/2013 | Utter, II |
| 8,452,364 | B2 | 5/2013 | Hannula et al. |
| 8,455,290 | B2 | 6/2013 | Siskavich |
| 8,457,703 | B2 | 6/2013 | Al-Ali |
| 8,457,707 | B2 | 6/2013 | Kiani |
| 8,463,349 | B2 | 6/2013 | Diab et al. |
| 8,466,286 | B2 | 6/2013 | Bellott et al. |
| 8,471,713 | B2 | 6/2013 | Poeze et al. |
| 8,473,020 | B2 | 6/2013 | Kiani et al. |
| D685,367 | S | 7/2013 | Akana et al. |
| 8,483,787 | B2 | 7/2013 | Al-Ali et al. |
| 8,489,364 | B2 | 7/2013 | Weber et al. |
| 8,496,595 | B2 | 7/2013 | Jornod |
| 8,498,684 | B2 | 7/2013 | Weber et al. |
| 8,504,128 | B2 | 8/2013 | Blank et al. |
| 8,509,867 | B2 | 8/2013 | Workman et al. |
| 8,515,509 | B2 | 8/2013 | Bruinsma et al. |
| 8,515,515 | B2 | 8/2013 | McKenna et al. |
| 8,523,781 | B2 | 9/2013 | Al-Ali |
| 8,529,301 | B2 | 9/2013 | Al-Ali et al. |
| 8,532,727 | B2 | 9/2013 | Ali et al. |
| 8,532,728 | B2 | 9/2013 | Diab et al. |
| D692,145 | S | 10/2013 | Al-Ali et al. |
| 8,547,209 | B2 | 10/2013 | Kiani et al. |
| 8,548,548 | B2 | 10/2013 | Al-Ali |
| 8,548,549 | B2 | 10/2013 | Schurman et al. |
| 8,548,550 | B2 | 10/2013 | Al-Ali et al. |
| 8,560,032 | B2 | 10/2013 | Al-Ali et al. |
| 8,560,034 | B1 | 10/2013 | Diab et al. |
| 8,570,167 | B2 | 10/2013 | Al-Ali |
| 8,570,503 | B2 | 10/2013 | Vo et al. |
| 8,571,617 | B2 | 10/2013 | Reichgott et al. |
| 8,571,618 | B1 | 10/2013 | Lamego et al. |
| 8,571,619 | B2 | 10/2013 | Al-Ali et al. |
| D694,182 | S | 11/2013 | Lee et al. |
| 8,577,431 | B2 | 11/2013 | Lamego et al. |
| 8,581,732 | B2 | 11/2013 | Al-Ali et al. |
| 8,584,345 | B2 | 11/2013 | Al-Ali et al. |
| 8,588,880 | B2 | 11/2013 | Abdul-Hafiz et al. |
| 8,591,426 | B2 | 11/2013 | Onoe et al. |
| D694,745 | S | 12/2013 | Akana et al. |
| 8,600,467 | B2 | 12/2013 | Al-Ali et al. |
| 8,606,342 | B2 | 12/2013 | Diab |
| 8,615,290 | B2 | 12/2013 | Lin et al. |
| D697,027 | S | 1/2014 | Ho |
| 8,624,836 | B1 | 1/2014 | Miller et al. |
| 8,626,255 | B2 | 1/2014 | Al-Ali et al. |
| 8,630,691 | B2 | 1/2014 | Lamego et al. |
| 8,634,889 | B2 | 1/2014 | Al-Ali et al. |
| 8,641,631 | B2 | 2/2014 | Sierra et al. |
| 8,652,060 | B2 | 2/2014 | Al-Ali |
| 8,655,004 | B2 | 2/2014 | Prest et al. |
| 8,663,107 | B2 | 3/2014 | Kiani |
| 8,666,468 | B1 | 3/2014 | Al-Ali |
| 8,667,967 | B2 | 3/2014 | Al-Ali et al. |
| 8,670,811 | B2 | 3/2014 | O'Reilly |
| 8,670,814 | B2 | 3/2014 | Diab et al. |
| 8,670,819 | B2 | 3/2014 | Iwamiya et al. |
| 8,676,286 | B2 | 3/2014 | Weber et al. |
| 8,682,407 | B2 | 3/2014 | Al-Ali |
| RE44,823 | E | 4/2014 | Parker |
| RE44,875 | E | 4/2014 | Kiani et al. |
| 8,690,799 | B2 | 4/2014 | Telfort et al. |
| 8,700,111 | B2 | 4/2014 | LeBoeuf et al. |
| 8,700,112 | B2 | 4/2014 | Kiani |
| 8,702,627 | B2 | 4/2014 | Telfort et al. |
| 8,706,179 | B2 | 4/2014 | Parker |
| 8,712,494 | B1 | 4/2014 | MacNeish, III et al. |
| D704,634 | S | 5/2014 | Eidelman et al. |
| 8,715,206 | B2 | 5/2014 | Telfort et al. |
| 8,718,735 | B2 | 5/2014 | Lamego et al. |
| 8,718,737 | B2 | 5/2014 | Diab et al. |
| 8,718,738 | B2 | 5/2014 | Blank et al. |
| 8,720,249 | B2 | 5/2014 | Al-Ali |
| 8,721,541 | B2 | 5/2014 | Al-Ali et al. |
| 8,721,542 | B2 | 5/2014 | Al-Ali et al. |
| 8,723,677 | B1 | 5/2014 | Kiani |
| 8,740,792 | B1 | 6/2014 | Kiani et al. |
| 8,754,776 | B2 | 6/2014 | Poeze et al. |
| 8,755,535 | B2 | 6/2014 | Telfort et al. |
| 8,755,856 | B2 | 6/2014 | Diab et al. |
| 8,755,872 | B1 | 6/2014 | Marinow |
| 8,760,517 | B2 | 6/2014 | Sarwar et al. |
| 8,761,850 | B2 | 6/2014 | Lamego |
| D709,873 | S | 7/2014 | Aumiller et al. |
| D709,874 | S | 7/2014 | Aumiller et al. |
| 8,764,671 | B2 | 7/2014 | Kiani |
| 8,768,423 | B2 | 7/2014 | Shakespeare et al. |
| 8,768,426 | B2 | 7/2014 | Haisley et al. |
| 8,771,204 | B2 | 7/2014 | Telfort et al. |
| 8,777,634 | B2 | 7/2014 | Kiani et al. |
| 8,781,543 | B2 | 7/2014 | Diab et al. |
| 8,781,544 | B2 | 7/2014 | Al-Ali et al. |
| 8,781,549 | B2 | 7/2014 | Al-Ali et al. |
| 8,787,984 | B2 | 7/2014 | Murakami et al. |
| 8,788,003 | B2 | 7/2014 | Schurman et al. |
| 8,790,268 | B2 | 7/2014 | Al-Ali |
| D711,372 | S | 8/2014 | Aumiller et al. |
| D711,873 | S | 8/2014 | Aumiller et al. |
| 8,801,613 | B2 | 8/2014 | Al-Ali et al. |
| 8,814,802 | B2 | 8/2014 | Iijima et al. |
| D712,930 | S | 9/2014 | Lee et al. |
| 8,821,397 | B2 | 9/2014 | Al-Ali et al. |
| 8,821,415 | B2 | 9/2014 | Al-Ali et al. |
| 8,830,449 | B1 | 9/2014 | Lamego et al. |
| 8,831,700 | B2 | 9/2014 | Schurman et al. |
| 8,838,210 | B2 | 9/2014 | Wood et al. |
| 8,840,549 | B2 | 9/2014 | Al-Ali et al. |
| 8,847,740 | B2 | 9/2014 | Kiani et al. |
| 8,849,365 | B2 | 9/2014 | Smith et al. |
| 8,852,094 | B2 | 10/2014 | Al-Ali et al. |
| 8,852,994 | B2 | 10/2014 | Wojtczuk et al. |
| 8,868,147 | B2 | 10/2014 | Stippick et al. |
| 8,868,150 | B2 | 10/2014 | Al-Ali et al. |
| 8,870,792 | B2 | 10/2014 | Al-Ali et al. |
| D718,233 | S | 11/2014 | Aumiller et al. |
| D718,234 | S | 11/2014 | Rautiainen |
| D718,236 | S | 11/2014 | Murray |
| D718,324 | S | 11/2014 | Lee et al. |
| 8,886,271 | B2 | 11/2014 | Kiani et al. |
| 8,888,539 | B2 | 11/2014 | Al-Ali et al. |
| 8,888,701 | B2 | 11/2014 | LeBoeuf et al. |

(56)                References Cited

U.S. PATENT DOCUMENTS

| | | | |
|---|---|---|---|
| 8,888,708 | B2 | 11/2014 | Diab et al. |
| 8,892,180 | B2 | 11/2014 | Weber et al. |
| 8,897,847 | B2 | 11/2014 | Al-Ali |
| D720,289 | S | 12/2014 | Chiang et al. |
| 8,909,310 | B2 | 12/2014 | Lamego et al. |
| 8,911,377 | B2 | 12/2014 | Al-Ali |
| 8,912,909 | B2 | 12/2014 | Al-Ali et al. |
| 8,920,317 | B2 | 12/2014 | Al-Ali et al. |
| 8,920,332 | B2 | 12/2014 | Hong et al. |
| 8,921,699 | B2 | 12/2014 | Al-Ali et al. |
| 8,922,382 | B2 | 12/2014 | Al-Ali et al. |
| 8,929,964 | B2 | 1/2015 | Al-Ali et al. |
| 8,942,777 | B2 | 1/2015 | Diab et al. |
| 8,948,832 | B2 | 2/2015 | Hong et al. |
| 8,948,834 | B2 | 2/2015 | Diab et al. |
| 8,948,835 | B2 | 2/2015 | Diab |
| 8,965,471 | B2 | 2/2015 | Lamego |
| D724,103 | S | 3/2015 | Akana et al. |
| 8,983,564 | B2 | 3/2015 | Al-Ali |
| 8,989,831 | B2 | 3/2015 | Al-Ali et al. |
| 8,996,085 | B2 | 3/2015 | Kiani et al. |
| D727,316 | S | 4/2015 | Song |
| 8,998,809 | B2 | 4/2015 | Kiani |
| 8,998,815 | B2 | 4/2015 | Venkatraman et al. |
| D729,238 | S | 5/2015 | Song |
| D729,796 | S | 5/2015 | Song |
| D730,347 | S | 5/2015 | Jung et al. |
| 9,028,429 | B2 | 5/2015 | Telfort et al. |
| 9,036,970 | B2 | 5/2015 | Guyon et al. |
| 9,037,207 | B2 | 5/2015 | Al-Ali et al. |
| D732,527 | S | 6/2015 | Kim et al. |
| D732,528 | S | 6/2015 | Kim et al. |
| D733,132 | S | 6/2015 | Kim et al. |
| D733,133 | S | 6/2015 | Kim et al. |
| 9,060,721 | B2 | 6/2015 | Reichgott et al. |
| 9,066,666 | B2 | 6/2015 | Kiani |
| 9,066,680 | B1 | 6/2015 | Al-Ali et al. |
| D735,131 | S | 7/2015 | Akana et al. |
| D735,190 | S | 7/2015 | Song |
| 9,072,437 | B2 | 7/2015 | Paalasmaa |
| 9,072,474 | B2 | 7/2015 | Al-Ali et al. |
| 9,078,560 | B2 | 7/2015 | Schurman et al. |
| 9,081,889 | B2 | 7/2015 | Ingrassia, Jr. et al. |
| 9,084,569 | B2 | 7/2015 | Weber et al. |
| 9,095,316 | B2 | 8/2015 | Welch et al. |
| 9,106,038 | B2 | 8/2015 | Telfort et al. |
| 9,107,625 | B2 | 8/2015 | Telfort et al. |
| 9,107,626 | B2 | 8/2015 | Al-Ali et al. |
| 9,113,831 | B2 | 8/2015 | Al-Ali |
| 9,113,832 | B2 | 8/2015 | Al-Ali |
| 9,119,595 | B2 | 9/2015 | Lamego |
| 9,131,881 | B2 | 9/2015 | Diab et al. |
| 9,131,882 | B2 | 9/2015 | Al-Ali et al. |
| 9,131,883 | B2 | 9/2015 | Al-Ali |
| 9,131,917 | B2 | 9/2015 | Telfort et al. |
| 9,138,180 | B1 | 9/2015 | Coverston et al. |
| 9,138,182 | B2 | 9/2015 | Al-Ali et al. |
| 9,138,192 | B2 | 9/2015 | Weber et al. |
| 9,142,117 | B2 | 9/2015 | Muhsin et al. |
| 9,153,112 | B1 | 10/2015 | Kiani et al. |
| 9,153,121 | B2 | 10/2015 | Kiani et al. |
| 9,161,696 | B2 | 10/2015 | Al-Ali et al. |
| 9,161,713 | B2 | 10/2015 | Al-Ali et al. |
| 9,167,995 | B2 | 10/2015 | Lamego et al. |
| 9,176,141 | B2 | 11/2015 | Al-Ali et al. |
| 9,186,102 | B2 | 11/2015 | Bruinsma et al. |
| 9,192,312 | B2 | 11/2015 | Al-Ali |
| 9,192,329 | B2 | 11/2015 | Al-Ali |
| 9,192,351 | B1 | 11/2015 | Telfort et al. |
| 9,195,385 | B2 | 11/2015 | Al-Ali et al. |
| D745,513 | S | 12/2015 | Jung et al. |
| D745,514 | S | 12/2015 | Jung et al. |
| 9,210,566 | B2 | 12/2015 | Ziemianska et al. |
| 9,211,072 | B2 | 12/2015 | Kiani |
| 9,211,095 | B1 | 12/2015 | Al-Ali |
| 9,218,454 | B2 | 12/2015 | Kiani et al. |
| D746,868 | S | 1/2016 | Akana et al. |
| 9,226,696 | B2 | 1/2016 | Kiani |
| 9,241,662 | B2 | 1/2016 | Al-Ali et al. |
| 9,245,668 | B1 | 1/2016 | Vo et al. |
| 9,259,185 | B2 | 2/2016 | Abdul-Hafiz et al. |
| 9,267,572 | B2 | 2/2016 | Barker et al. |
| D751,069 | S | 3/2016 | Choi et al. |
| D752,580 | S | 3/2016 | Choi et al. |
| D752,582 | S | 3/2016 | Jung et al. |
| 9,277,880 | B2 | 3/2016 | Poeze et al. |
| 9,289,167 | B2 | 3/2016 | Diab et al. |
| 9,295,421 | B2 | 3/2016 | Kiani et al. |
| D753,510 | S | 4/2016 | Puttorngul et al. |
| 9,307,928 | B1 | 4/2016 | Al-Ali et al. |
| 9,311,382 | B2 | 4/2016 | Varoglu et al. |
| 9,314,197 | B2 | 4/2016 | Eisen et al. |
| 9,316,495 | B2 | 4/2016 | Suzuki et al. |
| 9,323,894 | B2 | 4/2016 | Kiani |
| D755,176 | S | 5/2016 | Jung et al. |
| D755,392 | S | 5/2016 | Hwang et al. |
| D757,819 | S | 5/2016 | Akana et al. |
| 9,326,712 | B1 | 5/2016 | Kiani |
| 9,333,316 | B2 | 5/2016 | Kiani |
| 9,339,220 | B2 | 5/2016 | Lamego et al. |
| 9,339,236 | B2 | 5/2016 | Frix et al. |
| 9,341,565 | B2 | 5/2016 | Lamego et al. |
| 9,351,645 | B2 | 5/2016 | Irisawa |
| 9,351,673 | B2 | 5/2016 | Diab et al. |
| 9,351,675 | B2 | 5/2016 | Al-Ali et al. |
| 9,357,665 | B2 | 5/2016 | Myers et al. |
| D759,120 | S | 6/2016 | Akana et al. |
| D760,220 | S | 6/2016 | Aumiller et al. |
| 9,364,181 | B2 | 6/2016 | Kiani et al. |
| 9,368,671 | B2 | 6/2016 | Wojtczuk et al. |
| 9,370,325 | B2 | 6/2016 | Al-Ali et al. |
| 9,370,326 | B2 | 6/2016 | McHale et al. |
| 9,370,335 | B2 | 6/2016 | Al-Ali et al. |
| 9,375,185 | B2 | 6/2016 | Ali et al. |
| 9,386,953 | B2 | 7/2016 | Al-Ali |
| 9,386,961 | B2 | 7/2016 | Al-Ali et al. |
| 9,392,945 | B2 | 7/2016 | Al-Ali et al. |
| 9,392,946 | B1 | 7/2016 | Sarantos et al. |
| 9,397,448 | B2 | 7/2016 | Al-Ali et al. |
| 9,408,542 | B1 | 8/2016 | Kinast et al. |
| 9,423,952 | B2 | 8/2016 | Tamegai |
| D766,115 | S | 9/2016 | Ma |
| D766,235 | S | 9/2016 | Song |
| 9,436,645 | B2 | 9/2016 | Al-Ali et al. |
| 9,445,759 | B1 | 9/2016 | Lamego et al. |
| D768,622 | S | 10/2016 | Kim et al. |
| D768,724 | S | 10/2016 | Akana et al. |
| 9,460,846 | B2 | 10/2016 | Graham et al. |
| 9,466,919 | B2 | 10/2016 | Kiani et al. |
| 9,474,474 | B2 | 10/2016 | Lamego et al. |
| D770,533 | S | 11/2016 | Akana et al. |
| D771,624 | S | 11/2016 | Aumiller et al. |
| D772,228 | S | 11/2016 | Jung et al. |
| 9,480,422 | B2 | 11/2016 | Al-Ali |
| 9,480,435 | B2 | 11/2016 | Olsen |
| 9,489,081 | B2 | 11/2016 | Anzures et al. |
| 9,492,110 | B2 | 11/2016 | Al-Ali et al. |
| 9,497,534 | B2 | 11/2016 | Prest et al. |
| 9,510,779 | B2 | 12/2016 | Poeze et al. |
| 9,517,024 | B2 | 12/2016 | Kiani et al. |
| 9,526,430 | B2 | 12/2016 | Srinivas et al. |
| 9,532,722 | B2 | 1/2017 | Lamego et al. |
| 9,538,949 | B2 | 1/2017 | Al-Ali et al. |
| 9,538,980 | B2 | 1/2017 | Telfort et al. |
| 9,549,696 | B2 | 1/2017 | Lamego et al. |
| 9,553,625 | B2 | 1/2017 | Hatanaka et al. |
| 9,554,737 | B2 | 1/2017 | Schurman et al. |
| D780,223 | S | 2/2017 | Kim |
| 9,560,996 | B2 | 2/2017 | Kiani |
| 9,560,998 | B2 | 2/2017 | Al-Ali et al. |
| 9,566,019 | B2 | 2/2017 | Al-Ali et al. |
| 9,579,039 | B2 | 2/2017 | Jansen et al. |
| 9,583,256 | B2 | 2/2017 | Lapetina et al. |
| D782,537 | S | 3/2017 | Akana et al. |

(56) References Cited

U.S. PATENT DOCUMENTS

| | | | |
|---|---|---|---|
| 9,591,975 | B2 | 3/2017 | Dalvi et al. |
| 9,593,969 | B2 | 3/2017 | King |
| 9,622,692 | B2 | 4/2017 | Lamego et al. |
| 9,622,693 | B2 | 4/2017 | Diab |
| D787,714 | S | 5/2017 | Wang et al. |
| D788,079 | S | 5/2017 | Son et al. |
| D788,312 | S | 5/2017 | Al-Ali et al. |
| 9,636,055 | B2 | 5/2017 | Al Ali et al. |
| 9,636,056 | B2 | 5/2017 | Al-Ali |
| 9,649,054 | B2 | 5/2017 | Lamego et al. |
| 9,651,405 | B1 | 5/2017 | Gowreesunker et al. |
| 9,662,052 | B2 | 5/2017 | Al-Ali et al. |
| 9,668,676 | B2 | 6/2017 | Culbert |
| 9,668,679 | B2 | 6/2017 | Schurman et al. |
| 9,668,680 | B2 | 6/2017 | Bruinsma et al. |
| 9,668,703 | B2 | 6/2017 | Al-Ali |
| 9,675,286 | B2 | 6/2017 | Diab |
| 9,681,812 | B2 | 6/2017 | Presura |
| 9,683,894 | B2 | 6/2017 | Uematsu et al. |
| 9,684,900 | B2 | 6/2017 | Motoki et al. |
| 9,687,160 | B2 | 6/2017 | Kiani |
| 9,693,719 | B2 | 7/2017 | Al-Ali et al. |
| 9,693,737 | B2 | 7/2017 | Al-Ali |
| 9,697,928 | B2 | 7/2017 | Al-Ali et al. |
| 9,699,546 | B2 | 7/2017 | Qian et al. |
| 9,700,249 | B2 | 7/2017 | Johnson et al. |
| 9,716,937 | B2 | 7/2017 | Qian et al. |
| 9,717,425 | B2 | 8/2017 | Kiani et al. |
| 9,717,448 | B2 | 8/2017 | Frix et al. |
| 9,717,458 | B2 | 8/2017 | Lamego et al. |
| 9,723,997 | B1 | 8/2017 | Lamego |
| 9,724,016 | B1 | 8/2017 | Al-Ali et al. |
| 9,724,024 | B2 | 8/2017 | Al-Ali |
| 9,724,025 | B1 | 8/2017 | Kiani et al. |
| 9,730,640 | B2 | 8/2017 | Diab et al. |
| 9,743,887 | B2 | 8/2017 | Al-Ali et al. |
| 9,749,232 | B2 | 8/2017 | Sampath et al. |
| D797,809 | S | 9/2017 | Akana et al. |
| D797,810 | S | 9/2017 | Akana et al. |
| 9,750,442 | B2 | 9/2017 | Olsen |
| 9,750,443 | B2 | 9/2017 | Smith et al. |
| 9,750,461 | B1 | 9/2017 | Telfort |
| 9,752,925 | B2 | 9/2017 | Chu et al. |
| D800,172 | S | 10/2017 | Akana et al. |
| 9,775,545 | B2 | 10/2017 | Al-Ali et al. |
| 9,775,546 | B2 | 10/2017 | Diab et al. |
| 9,775,548 | B2 | 10/2017 | Sarantos et al. |
| 9,775,570 | B2 | 10/2017 | Al-Ali |
| 9,778,079 | B1 | 10/2017 | Al-Ali et al. |
| 9,781,984 | B2 | 10/2017 | Baranski et al. |
| 9,782,077 | B2 | 10/2017 | Lamego et al. |
| 9,782,110 | B2 | 10/2017 | Kiani |
| 9,787,568 | B2 | 10/2017 | Lamego et al. |
| 9,788,735 | B2 | 10/2017 | Al-Ali |
| 9,788,768 | B2 | 10/2017 | Al-Ali et al. |
| 9,795,300 | B2 | 10/2017 | Al-Ali |
| 9,795,310 | B2 | 10/2017 | Al-Ali |
| 9,795,358 | B2 | 10/2017 | Telfort et al. |
| 9,795,739 | B2 | 10/2017 | Al-Ali et al. |
| 9,801,556 | B2 | 10/2017 | Kiani |
| 9,801,588 | B2 | 10/2017 | Weber et al. |
| 9,808,188 | B1 | 11/2017 | Perea et al. |
| 9,814,418 | B2 | 11/2017 | Weber et al. |
| 9,820,691 | B2 | 11/2017 | Kiani |
| D806,063 | S | 12/2017 | Kim |
| 9,833,152 | B2 | 12/2017 | Kiani et al. |
| 9,833,180 | B2 | 12/2017 | Shakespeare et al. |
| 9,838,775 | B2 | 12/2017 | Qian et al. |
| 9,839,379 | B2 | 12/2017 | Al-Ali et al. |
| 9,839,381 | B1 | 12/2017 | Weber et al. |
| 9,847,002 | B2 | 12/2017 | Kiani et al. |
| 9,847,749 | B2 | 12/2017 | Kiani et al. |
| 9,848,800 | B1 | 12/2017 | Lee et al. |
| 9,848,806 | B2 | 12/2017 | Al-Ali |
| 9,848,807 | B2 | 12/2017 | Lamego |
| 9,848,823 | B2 | 12/2017 | Raghuram et al. |
| D807,351 | S | 1/2018 | Bang et al. |
| 9,861,298 | B2 | 1/2018 | Eckerbom et al. |
| 9,861,304 | B2 | 1/2018 | Al-Ali et al. |
| 9,861,305 | B1 | 1/2018 | Weber et al. |
| 9,866,671 | B1 | 1/2018 | Thompson et al. |
| 9,867,575 | B2 | 1/2018 | Maani et al. |
| 9,867,578 | B2 | 1/2018 | Al-Ali et al. |
| 9,872,623 | B2 | 1/2018 | Al-Ali |
| 9,876,320 | B2 | 1/2018 | Coverston et al. |
| 9,877,650 | B2 | 1/2018 | Muhsin et al. |
| 9,877,686 | B2 | 1/2018 | Al-Ali et al. |
| D809,512 | S | 2/2018 | Mistry et al. |
| 9,891,079 | B2 | 2/2018 | Dalvi |
| 9,891,590 | B2 | 2/2018 | Shim et al. |
| 9,895,107 | B2 | 2/2018 | Al-Ali et al. |
| 9,898,049 | B2 | 2/2018 | Myers et al. |
| D812,607 | S | 3/2018 | Mistry et al. |
| 9,913,617 | B2 | 3/2018 | Al-Ali et al. |
| 9,918,646 | B2 | 3/2018 | Singh Alvarado et al. |
| 9,924,874 | B2 | 3/2018 | Sato |
| 9,924,893 | B2 | 3/2018 | Schurman et al. |
| 9,924,897 | B1 | 3/2018 | Abdul-Hafiz |
| 9,936,917 | B2 | 4/2018 | Poeze et al. |
| 9,943,269 | B2 | 4/2018 | Muhsin et al. |
| 9,949,676 | B2 | 4/2018 | Al-Ali |
| 9,952,095 | B1 | 4/2018 | Hotelling et al. |
| D816,524 | S | 5/2018 | Akana et al. |
| D819,021 | S | 5/2018 | Mistry et al. |
| 9,955,937 | B2 | 5/2018 | Telfort |
| 9,965,946 | B2 | 5/2018 | Al-Ali et al. |
| 9,980,667 | B2 | 5/2018 | Kiani et al. |
| D820,865 | S | 6/2018 | Muhsin et al. |
| 9,986,919 | B2 | 6/2018 | Lamego et al. |
| 9,986,952 | B2 | 6/2018 | Dalvi et al. |
| 9,989,560 | B2 | 6/2018 | Poeze et al. |
| 9,993,200 | B2 | 6/2018 | Jeong |
| 9,993,207 | B2 | 6/2018 | Al-Ali et al. |
| 10,007,758 | B2 | 6/2018 | Al-Ali et al. |
| D822,215 | S | 7/2018 | Al-Ali et al. |
| D822,216 | S | 7/2018 | Barker et al. |
| D823,301 | S | 7/2018 | Bang et al. |
| 10,010,276 | B2 | 7/2018 | Al-Ali et al. |
| 10,032,002 | B2 | 7/2018 | Kiani et al. |
| 10,039,080 | B2 | 7/2018 | Miller et al. |
| 10,039,482 | B2 | 8/2018 | Al-Ali et al. |
| 10,039,491 | B2 | 8/2018 | Thompson et al. |
| 10,052,037 | B2 | 8/2018 | Kinast et al. |
| 10,055,121 | B2 | 8/2018 | Chaudhri et al. |
| 10,058,275 | B2 | 8/2018 | Al-Ali et al. |
| D827,831 | S | 9/2018 | Fong et al. |
| 10,064,562 | B2 | 9/2018 | Al-Ali |
| 10,066,970 | B2 | 9/2018 | Gowreesunker et al. |
| 10,076,257 | B2 | 9/2018 | Lin et al. |
| 10,078,052 | B2 | 9/2018 | Ness et al. |
| 10,085,656 | B2 | 10/2018 | Sato |
| 10,086,138 | B1 | 10/2018 | Novak, Jr. |
| 10,090,712 | B2 | 10/2018 | Jabori et al. |
| 10,092,200 | B2 | 10/2018 | Al-Ali et al. |
| 10,092,244 | B2 | 10/2018 | Chuang et al. |
| 10,092,249 | B2 | 10/2018 | Kiani et al. |
| 10,098,550 | B2 | 10/2018 | Al-Ali et al. |
| 10,098,591 | B2 | 10/2018 | Al-Ali et al. |
| 10,098,610 | B2 | 10/2018 | Al-Ali et al. |
| D833,624 | S | 11/2018 | DeJong et al. |
| 10,117,587 | B2 | 11/2018 | Han |
| 10,123,726 | B2 | 11/2018 | Al-Ali et al. |
| 10,130,289 | B2 | 11/2018 | Al-Ali et al. |
| 10,130,291 | B2 | 11/2018 | Schurman et al. |
| D835,282 | S | 12/2018 | Barker et al. |
| D835,283 | S | 12/2018 | Barker et al. |
| D835,284 | S | 12/2018 | Barker et al. |
| D835,285 | S | 12/2018 | Barker et al. |
| 10,149,616 | B2 | 12/2018 | Al-Ali et al. |
| 10,154,815 | B2 | 12/2018 | Al-Ali et al. |
| 10,159,412 | B2 | 12/2018 | Lamego et al. |
| 10,165,954 | B2 | 1/2019 | Lee |
| 10,188,296 | B2 | 1/2019 | Al-Ali et al. |
| 10,188,331 | B1 | 1/2019 | Kiani et al. |

(56) References Cited

U.S. PATENT DOCUMENTS

| | | | |
|---|---|---|---|
| 10,188,348 B2 | 1/2019 | Al-Ali et al. |
| RE47,218 E | 2/2019 | Al-Ali |
| RE47,244 E | 2/2019 | Kiani et al. |
| RE47,249 E | 2/2019 | Kiani et al. |
| D839,753 S | 2/2019 | Domke et al. |
| 10,194,847 B2 | 2/2019 | Al-Ali |
| 10,194,848 B1 | 2/2019 | Kiani et al. |
| 10,201,286 B2 | 2/2019 | Waydo |
| 10,201,298 B2 | 2/2019 | Al-Ali et al. |
| 10,205,272 B2 | 2/2019 | Kiani et al. |
| 10,205,291 B2 | 2/2019 | Scruggs et al. |
| 10,213,108 B2 | 2/2019 | Al-Ali |
| 10,215,698 B2 | 2/2019 | Han et al. |
| 10,219,706 B2 | 3/2019 | Al-Ali |
| 10,219,746 B2 | 3/2019 | McHale et al. |
| 10,219,754 B1 | 3/2019 | Lamego |
| 10,226,187 B2 | 3/2019 | Al-Ali et al. |
| 10,226,576 B2 | 3/2019 | Kiani |
| 10,231,629 B1 | 3/2019 | Pei et al. |
| 10,231,657 B2 | 3/2019 | Al-Ali et al. |
| 10,231,670 B2 | 3/2019 | Blank et al. |
| 10,231,676 B2 | 3/2019 | Al-Ali et al. |
| RE47,353 E | 4/2019 | Kiani et al. |
| 10,247,670 B2 | 4/2019 | Ness et al. |
| 10,251,585 B2 | 4/2019 | Al-Ali et al. |
| 10,251,586 B2 | 4/2019 | Lamego |
| 10,255,994 B2 | 4/2019 | Sampath et al. |
| 10,258,265 B1 | 4/2019 | Poeze et al. |
| 10,258,266 B1 | 4/2019 | Poeze et al. |
| 10,265,024 B2 | 4/2019 | Lee et al. |
| 10,271,748 B2 | 4/2019 | Al-Ali |
| 10,278,626 B2 | 5/2019 | Schurman et al. |
| 10,278,648 B2 | 5/2019 | Al-Ali et al. |
| 10,279,247 B2 | 5/2019 | Kiani |
| 10,285,626 B1 | 5/2019 | Kestelli et al. |
| 10,292,628 B1 | 5/2019 | Poeze et al. |
| 10,292,657 B2 | 5/2019 | Abdul-Hafiz et al. |
| 10,292,664 B2 | 5/2019 | Ai-Ali |
| 10,299,708 B1 | 5/2019 | Poeze et al. |
| 10,299,709 B2 | 5/2019 | Perea et al. |
| 10,305,775 B2 | 5/2019 | Lamego et al. |
| 10,307,111 B2 | 6/2019 | Muhsin et al. |
| 10,325,681 B2 | 6/2019 | Sampath et al. |
| 10,327,337 B2 | 6/2019 | Schmidt et al. |
| 10,390,716 B2 | 8/2019 | Shimuta |
| 10,398,383 B2 | 9/2019 | van Dinther et al. |
| 10,406,445 B2 | 9/2019 | Vock et al. |
| 10,416,079 B2 | 9/2019 | Magnussen et al. |
| D861,676 S | 10/2019 | Mistry et al. |
| 10,433,043 B2 | 10/2019 | Hankey et al. |
| 10,448,871 B2 | 10/2019 | Al-Ali et al. |
| 10,448,876 B2 | 10/2019 | Hutchinson |
| D866,350 S | 11/2019 | Park et al. |
| 10,466,889 B2 | 11/2019 | Tyler |
| 10,470,695 B2 | 11/2019 | Al-Ali et al. |
| 10,524,671 B2 | 1/2020 | Lamego |
| 10,537,284 B1 | 1/2020 | Ruh et al. |
| 10,542,920 B2 | 1/2020 | Sato |
| D875,092 S | 2/2020 | Akana et al. |
| 10,575,766 B2 | 3/2020 | Sato |
| D882,565 S | 4/2020 | Akana et al. |
| 10,610,157 B2 | 4/2020 | Pandya et al. |
| 10,627,783 B2 | 4/2020 | Rothkopf et al. |
| D883,279 S | 5/2020 | Akana et al. |
| 10,638,961 B2 | 5/2020 | Al-Ali et al. |
| 10,646,146 B2 | 5/2020 | Al-Ali et al. |
| 10,687,743 B1 | 6/2020 | Al-Ali et al. |
| 10,687,744 B1 | 6/2020 | Al-Ali et al. |
| 10,687,745 B1 | 6/2020 | Al-Ali et al. |
| 10,722,157 B2 | 7/2020 | Bower et al. |
| 10,722,159 B2 | 7/2020 | Al-Ali et al. |
| 10,799,128 B2 | 10/2020 | Paulussen et al. |
| 10,905,348 B2 | 2/2021 | Grunwald et al. |
| 10,912,501 B2 | 2/2021 | Poeze et al. |
| 10,912,502 B2 | 2/2021 | Poeze et al. |
| 10,942,491 B2 | 3/2021 | Rothkopf et al. |
| 10,945,648 B2 | 3/2021 | Poeze et al. |
| 10,987,054 B2 | 4/2021 | Pandya et al. |
| 11,009,390 B2 | 5/2021 | Hotelling et al. |
| 11,106,352 B2 | 8/2021 | Tyler |
| D947,842 S | 4/2022 | Akana et al. |
| D949,144 S | 4/2022 | Akana et al. |
| D949,145 S | 4/2022 | Akana et al. |
| D953,324 S | 5/2022 | Akana et al. |
| D962,933 S | 9/2022 | Akana et al. |
| D962,934 S | 9/2022 | Akana et al. |
| D962,936 S | 9/2022 | Akana et al. |
| 11,474,483 B2 | 10/2022 | Rothkopf et al. |
| 2001/0056243 A1 | 12/2001 | Ohsaki et al. |
| 2002/0015034 A1 | 2/2002 | Malmborg |
| 2002/0019586 A1 | 2/2002 | Teller et al. |
| 2002/0042558 A1 | 4/2002 | Mendelson |
| 2002/0095092 A1 | 7/2002 | Kondo et al. |
| 2002/0161291 A1 | 10/2002 | Kianl et al. |
| 2002/0184055 A1 | 12/2002 | Naghavi et al. |
| 2002/0188210 A1 | 12/2002 | Aizawa |
| 2003/0036689 A1 | 2/2003 | Diab et al. |
| 2003/0036690 A1 | 2/2003 | Geddes et al. |
| 2003/0125612 A1 | 7/2003 | Fox et al. |
| 2003/0212316 A1 | 11/2003 | Leiden et al. |
| 2004/0039272 A1 | 2/2004 | Abdul-Hafiz et al. |
| 2004/0054290 A1 | 3/2004 | Chance |
| 2004/0114783 A1 | 6/2004 | Spycher et al. |
| 2005/0030518 A1 | 2/2005 | Nishi et al. |
| 2005/0033284 A1 | 2/2005 | Hooven et al. |
| 2005/0116820 A1 | 6/2005 | Goldreich |
| 2005/0267346 A1 | 12/2005 | Faber et al. |
| 2005/0274971 A1 | 12/2005 | Wang et al. |
| 2005/0277819 A1 | 12/2005 | Kiani et al. |
| 2006/0009607 A1 | 1/2006 | Lutz et al. |
| 2006/0009698 A1 | 1/2006 | Banet et al. |
| 2006/0128869 A1 | 6/2006 | Taima |
| 2006/0142654 A1 | 6/2006 | Rytky |
| 2006/0161054 A1 | 7/2006 | Reuss et al. |
| 2006/0182659 A1 | 8/2006 | Unlu et al. |
| 2006/0253010 A1 | 11/2006 | Brady et al. |
| 2007/0021677 A1 | 1/2007 | Markel |
| 2007/0093717 A1 | 4/2007 | Nagar et al. |
| 2007/0228404 A1 | 10/2007 | Tran et al. |
| 2007/0232880 A1 | 10/2007 | Siddiqui et al. |
| 2007/0271009 A1 | 11/2007 | Conroy |
| 2007/0276270 A1 | 11/2007 | Tran |
| 2007/0282478 A1 | 12/2007 | Al-Ali et al. |
| 2008/0004904 A1 | 1/2008 | Tran |
| 2008/0030468 A1 | 2/2008 | Ali et al. |
| 2008/0165063 A1 | 7/2008 | Schlub et al. |
| 2008/0208009 A1 | 8/2008 | Shklarski |
| 2009/0018452 A1 | 1/2009 | Sugiura et al. |
| 2009/0054112 A1 | 2/2009 | Cybart et al. |
| 2009/0054751 A1 | 2/2009 | Babashan et al. |
| 2009/0059730 A1 | 3/2009 | Lyons et al. |
| 2009/0097129 A1 | 4/2009 | Naito et al. |
| 2009/0177097 A1 | 7/2009 | Ma et al. |
| 2009/0190198 A1 | 7/2009 | Kwon |
| 2009/0247984 A1 | 10/2009 | Lamego et al. |
| 2009/0275810 A1 | 11/2009 | Ayers et al. |
| 2009/0275813 A1 | 11/2009 | Davis |
| 2009/0275844 A1 | 11/2009 | Al-Ali |
| 2010/0004518 A1 | 1/2010 | Vo et al. |
| 2010/0030040 A1 | 2/2010 | Poeze et al. |
| 2010/0030043 A1 | 2/2010 | Kuhn |
| 2010/0113902 A1 | 5/2010 | Hete et al. |
| 2010/0113948 A1 | 5/2010 | Yang et al. |
| 2010/0193804 A1 | 8/2010 | Brown et al. |
| 2010/0261986 A1 | 10/2010 | Chin et al. |
| 2010/0324384 A1 | 12/2010 | Moon et al. |
| 2011/0004106 A1 | 1/2011 | Iwamiya |
| 2011/0082711 A1 | 4/2011 | Poeze et al. |
| 2011/0085721 A1 | 4/2011 | Guyon et al. |
| 2011/0105854 A1 | 5/2011 | Kiani et al. |
| 2011/0125060 A1 | 5/2011 | Telfort et al. |
| 2011/0208015 A1 | 8/2011 | Welch et al. |
| 2011/0213212 A1 | 9/2011 | Al-Ali |
| 2011/0230733 A1 | 9/2011 | Al-Ali |

(56) References Cited

U.S. PATENT DOCUMENTS

| | | |
|---|---|---|
| 2011/0237969 A1 | 9/2011 | Eckerbom et al. |
| 2011/0245697 A1 | 10/2011 | Miettinen |
| 2011/0288383 A1 | 11/2011 | Diab |
| 2011/0301444 A1 | 12/2011 | Al-Ali |
| 2012/0016219 A1 | 1/2012 | Fujii |
| 2012/0041316 A1 | 2/2012 | Al Ali et al. |
| 2012/0046557 A1 | 2/2012 | Kiani |
| 2012/0059267 A1 | 3/2012 | Lamego et al. |
| 2012/0078116 A1 | 3/2012 | Yamashita |
| 2012/0088984 A1 | 4/2012 | Al-Ali et al. |
| 2012/0104999 A1 | 5/2012 | Teggatz et al. |
| 2012/0129495 A1 | 5/2012 | Chae et al. |
| 2012/0150052 A1 | 6/2012 | Buchheim et al. |
| 2012/0165629 A1 | 6/2012 | Merritt et al. |
| 2012/0179006 A1 | 7/2012 | Jansen et al. |
| 2012/0197093 A1 | 8/2012 | LeBoeuf et al. |
| 2012/0197137 A1 | 8/2012 | Jeanne et al. |
| 2012/0209082 A1 | 8/2012 | Al-Ali |
| 2012/0209084 A1 | 8/2012 | Olsen et al. |
| 2012/0221254 A1 | 8/2012 | Kateraas et al. |
| 2012/0283524 A1 | 11/2012 | Kiani et al. |
| 2012/0288230 A1 | 11/2012 | Polonge et al. |
| 2012/0296178 A1 | 11/2012 | Lamego et al. |
| 2012/0319816 A1 | 12/2012 | Al-Ali |
| 2012/0330112 A1 | 12/2012 | Lamego et al. |
| 2013/0006074 A1 | 1/2013 | Pologe |
| 2013/0006076 A1 | 1/2013 | McHale et al. |
| 2013/0018233 A1 | 1/2013 | Cinbis et al. |
| 2013/0023775 A1 | 1/2013 | Lamego et al. |
| 2013/0041591 A1 | 2/2013 | Lamego |
| 2013/0046204 A1 | 2/2013 | Lamego et al. |
| 2013/0060147 A1 | 3/2013 | Welch et al. |
| 2013/0085346 A1 | 4/2013 | Lin et al. |
| 2013/0096405 A1 | 4/2013 | Garfio |
| 2013/0096936 A1 | 4/2013 | Sampath et al. |
| 2013/0131474 A1 | 5/2013 | Gu et al. |
| 2013/0190581 A1 | 7/2013 | Al-Ali et al. |
| 2013/0204112 A1 | 8/2013 | White et al. |
| 2013/0211214 A1 | 8/2013 | Olsen |
| 2013/0227418 A1 | 8/2013 | Sa et al. |
| 2013/0239058 A1 | 9/2013 | Yao et al. |
| 2013/0243021 A1 | 9/2013 | Siskavich |
| 2013/0253334 A1 | 9/2013 | Al-Ali et al. |
| 2013/0262730 A1 | 10/2013 | Al-Ali et al. |
| 2013/0264592 A1 | 10/2013 | Bergmann et al. |
| 2013/0267804 A1 | 10/2013 | Al-Ali |
| 2013/0267854 A1 | 10/2013 | Johnson et al. |
| 2013/0274572 A1 | 10/2013 | Al-Ali et al. |
| 2013/0296672 A1 | 11/2013 | O'Neil et al. |
| 2013/0296713 A1 | 11/2013 | Al-Ali et al. |
| 2013/0305351 A1 | 11/2013 | Narendra et al. |
| 2013/0317370 A1 | 11/2013 | Dalvi et al. |
| 2013/0324808 A1 | 12/2013 | Al-Ali et al. |
| 2013/0331660 A1 | 12/2013 | Al-Ali et al. |
| 2013/0331670 A1 | 12/2013 | Kiani |
| 2014/0012100 A1 | 1/2014 | Al-Ali et al. |
| 2014/0034353 A1 | 2/2014 | Al-Ali et al. |
| 2014/0051943 A1 | 2/2014 | Gillette |
| 2014/0051953 A1 | 2/2014 | Lamego et al. |
| 2014/0051955 A1 | 2/2014 | Tiao et al. |
| 2014/0066783 A1 | 3/2014 | Kiani et al. |
| 2014/0073887 A1 | 3/2014 | Petersen et al. |
| 2014/0073960 A1 | 3/2014 | Rodriguez-Llorente et al. |
| 2014/0077956 A1 | 3/2014 | Sampath et al. |
| 2014/0081100 A1 | 3/2014 | Muhsin et al. |
| 2014/0081175 A1 | 3/2014 | Telfort |
| 2014/0094667 A1 | 4/2014 | Schurman et al. |
| 2014/0100434 A1 | 4/2014 | Diab et al. |
| 2014/0101597 A1 | 4/2014 | Bamford et al. |
| 2014/0107493 A1 | 4/2014 | Yuen et al. |
| 2014/0114199 A1 | 4/2014 | Lamego et al. |
| 2014/0117926 A1 | 5/2014 | Hwu et al. |
| 2014/0120564 A1 | 5/2014 | Workman et al. |
| 2014/0121482 A1 | 5/2014 | Merritt et al. |
| 2014/0121483 A1 | 5/2014 | Kiani |
| 2014/0127137 A1 | 5/2014 | Bellott et al. |
| 2014/0129702 A1 | 5/2014 | Lamego et al. |
| 2014/0135588 A1 | 5/2014 | Al-Ali et al. |
| 2014/0135594 A1 | 5/2014 | Yuen et al. |
| 2014/0139486 A1 | 5/2014 | Mistry et al. |
| 2014/0142401 A1 | 5/2014 | Al-Ali et al. |
| 2014/0163344 A1 | 6/2014 | Al-Ali |
| 2014/0163402 A1 | 6/2014 | Lamego et al. |
| 2014/0166076 A1 | 6/2014 | Kiani et al. |
| 2014/0171146 A1 | 6/2014 | Ma et al. |
| 2014/0171763 A1 | 6/2014 | Diab |
| 2014/0180038 A1 | 6/2014 | Kiani |
| 2014/0180154 A1 | 6/2014 | Sierra et al. |
| 2014/0180160 A1 | 6/2014 | Brown et al. |
| 2014/0187973 A1 | 7/2014 | Brown et al. |
| 2014/0189577 A1 | 7/2014 | Shuttleworth et al. |
| 2014/0192177 A1 | 7/2014 | Bartula et al. |
| 2014/0194766 A1 | 7/2014 | Al-Ali et al. |
| 2014/0206954 A1 | 7/2014 | Yuen et al. |
| 2014/0206963 A1 | 7/2014 | Al-Ali |
| 2014/0213864 A1 | 7/2014 | Abdul-Hafiz et al. |
| 2014/0221854 A1 | 8/2014 | Wai |
| 2014/0266790 A1 | 9/2014 | Al-Ali et al. |
| 2014/0275808 A1 | 9/2014 | Poeze et al. |
| 2014/0275835 A1 | 9/2014 | Lamego et al. |
| 2014/0275852 A1 | 9/2014 | Hong et al. |
| 2014/0275854 A1 | 9/2014 | Venkatraman et al. |
| 2014/0275871 A1 | 9/2014 | Lamego et al. |
| 2014/0275872 A1 | 9/2014 | Merritt et al. |
| 2014/0275881 A1 | 9/2014 | Lamego et al. |
| 2014/0276013 A1 | 9/2014 | Muehlemann et al. |
| 2014/0276115 A1 | 9/2014 | Dalvi et al. |
| 2014/0276116 A1 | 9/2014 | Takahashi et al. |
| 2014/0288400 A1 | 9/2014 | Diab et al. |
| 2014/0303520 A1 | 10/2014 | Telfort et al. |
| 2014/0316217 A1 | 10/2014 | Purdon et al. |
| 2014/0316218 A1 | 10/2014 | Purdon et al. |
| 2014/0316228 A1 | 10/2014 | Blank et al. |
| 2014/0323825 A1 | 10/2014 | Al-Ali et al. |
| 2014/0323829 A1 | 10/2014 | LeBoeuf et al. |
| 2014/0323897 A1 | 10/2014 | Brown et al. |
| 2014/0323898 A1 | 10/2014 | Purdon et al. |
| 2014/0330092 A1 | 11/2014 | Al-Ali et al. |
| 2014/0330098 A1 | 11/2014 | Merritt et al. |
| 2014/0330099 A1 | 11/2014 | Al-Ali et al. |
| 2014/0336481 A1 | 11/2014 | Shakespeare et al. |
| 2014/0357966 A1 | 12/2014 | Al-Ali et al. |
| 2014/0361147 A1 | 12/2014 | Fei |
| 2014/0371548 A1 | 12/2014 | Al-Ali et al. |
| 2014/0371632 A1 | 12/2014 | Al-Ali et al. |
| 2014/0378784 A1 | 12/2014 | Kiani et al. |
| 2014/0378844 A1 | 12/2014 | Fei |
| 2015/0005600 A1 | 1/2015 | Blank et al. |
| 2015/0011907 A1 | 1/2015 | Purdon et al. |
| 2015/0012231 A1 | 1/2015 | Poeze et al. |
| 2015/0018647 A1 | 1/2015 | Mandel et al. |
| 2015/0018650 A1 | 1/2015 | Al-Ali et al. |
| 2015/0025406 A1 | 1/2015 | Al-Ali |
| 2015/0032029 A1 | 1/2015 | Al-Ali et al. |
| 2015/0038859 A1 | 2/2015 | Dalvi et al. |
| 2015/0045637 A1 | 2/2015 | Dalvi |
| 2015/0045685 A1 | 2/2015 | Al-Ali et al. |
| 2015/0051462 A1 | 2/2015 | Olsen |
| 2015/0065889 A1 | 3/2015 | Gandelman et al. |
| 2015/0080754 A1 | 3/2015 | Purdon et al. |
| 2015/0087936 A1 | 3/2015 | Al-Ali et al. |
| 2015/0094546 A1 | 4/2015 | Al-Ali |
| 2015/0095819 A1 | 4/2015 | Hong et al. |
| 2015/0097701 A1 | 4/2015 | Muhsin et al. |
| 2015/0099324 A1 | 4/2015 | Wojtczuk et al. |
| 2015/0099950 A1 | 4/2015 | Al-Ali et al. |
| 2015/0099951 A1 | 4/2015 | Al-Ali et al. |
| 2015/0099955 A1 | 4/2015 | Al-Ali et al. |
| 2015/0101844 A1 | 4/2015 | Al-Ali et al. |
| 2015/0106121 A1 | 4/2015 | Muhsin et al. |
| 2015/0112151 A1 | 4/2015 | Muhsin et al. |
| 2015/0112168 A1 | 4/2015 | Conrad et al. |
| 2015/0116076 A1 | 4/2015 | Al-Ali et al. |
| 2015/0119657 A1 | 4/2015 | LeBoeuf et al. |

(56) References Cited

U.S. PATENT DOCUMENTS

| | | |
|---|---|---|
| 2015/0119725 A1 | 4/2015 | Martin et al. |
| 2015/0126830 A1 | 5/2015 | Schurman et al. |
| 2015/0133755 A1 | 5/2015 | Smith et al. |
| 2015/0135310 A1 | 5/2015 | Lee |
| 2015/0140863 A1 | 5/2015 | Al-Ali et al. |
| 2015/0141781 A1 | 5/2015 | Weber et al. |
| 2015/0153843 A1 | 6/2015 | Lee |
| 2015/0165312 A1 | 6/2015 | Kiani |
| 2015/0173671 A1 | 6/2015 | Paalasmaa et al. |
| 2015/0196237 A1 | 7/2015 | Lamego |
| 2015/0201874 A1 | 7/2015 | Diab |
| 2015/0208966 A1 | 7/2015 | Al-Ali |
| 2015/0214749 A1 | 7/2015 | Park et al. |
| 2015/0216459 A1 | 8/2015 | Al-Ali et al. |
| 2015/0230755 A1 | 8/2015 | Al-Ali et al. |
| 2015/0238722 A1 | 8/2015 | Al-Ali |
| 2015/0245773 A1 | 9/2015 | Lamego et al. |
| 2015/0245793 A1 | 9/2015 | Al-Ali et al. |
| 2015/0245794 A1 | 9/2015 | Al-Ali |
| 2015/0255001 A1 | 9/2015 | Haughav et al. |
| 2015/0257689 A1 | 9/2015 | Al-Ali et al. |
| 2015/0272444 A1 | 10/2015 | Maslov et al. |
| 2015/0272514 A1 | 10/2015 | Kiani et al. |
| 2015/0281424 A1 | 10/2015 | Vock et al. |
| 2015/0282739 A1 | 10/2015 | Nishida et al. |
| 2015/0318100 A1 | 11/2015 | Rothkopf et al. |
| 2015/0346976 A1 | 12/2015 | Karunamuni et al. |
| 2015/0351697 A1 | 12/2015 | Weber et al. |
| 2015/0351704 A1 | 12/2015 | Kiani et al. |
| 2015/0355604 A1 | 12/2015 | Fraser et al. |
| 2015/0359429 A1 | 12/2015 | Al-Ali et al. |
| 2015/0366472 A1 | 12/2015 | Kiani |
| 2015/0366507 A1 | 12/2015 | Blank et al. |
| 2015/0374298 A1 | 12/2015 | Al-Ali et al. |
| 2015/0380875 A1 | 12/2015 | Coverston et al. |
| 2016/0000362 A1 | 1/2016 | Diab et al. |
| 2016/0007930 A1 | 1/2016 | Weber et al. |
| 2016/0019360 A1 | 1/2016 | Pahwa et al. |
| 2016/0022160 A1 | 1/2016 | Pi et al. |
| 2016/0023245 A1 | 1/2016 | Zadesky et al. |
| 2016/0029932 A1 | 2/2016 | Al-Ali |
| 2016/0029933 A1 | 2/2016 | Al-Ali et al. |
| 2016/0038045 A1 | 2/2016 | Shapiro |
| 2016/0041531 A1 | 2/2016 | Mackie et al. |
| 2016/0042162 A1 | 2/2016 | Newell |
| 2016/0045118 A1 | 2/2016 | Kiani |
| 2016/0051147 A1 | 2/2016 | Cohen et al. |
| 2016/0051157 A1 | 2/2016 | Waydo |
| 2016/0051158 A1 | 2/2016 | Silva |
| 2016/0051205 A1 | 2/2016 | Al-Ali et al. |
| 2016/0058302 A1 | 3/2016 | Raghuram et al. |
| 2016/0058309 A1 | 3/2016 | Han |
| 2016/0058310 A1 | 3/2016 | Lijima |
| 2016/0058312 A1 | 3/2016 | Han et al. |
| 2016/0058338 A1 | 3/2016 | Schurman et al. |
| 2016/0058347 A1 | 3/2016 | Reichgott et al. |
| 2016/0058356 A1 | 3/2016 | Raghuram et al. |
| 2016/0058370 A1 | 3/2016 | Raghuram et al. |
| 2016/0058375 A1 | 3/2016 | Rothkopf |
| 2016/0066823 A1 | 3/2016 | Al-Ali et al. |
| 2016/0066824 A1 | 3/2016 | Al-Ali et al. |
| 2016/0066879 A1 | 3/2016 | Telfort et al. |
| 2016/0071392 A1 | 3/2016 | Hankey et al. |
| 2016/0072429 A1 | 3/2016 | Kiani et al. |
| 2016/0073914 A1 | 3/2016 | Lapetina et al. |
| 2016/0073967 A1 | 3/2016 | Lamego et al. |
| 2016/0081552 A1 | 3/2016 | Wojtczuk et al. |
| 2016/0095543 A1 | 4/2016 | Telfort et al. |
| 2016/0095548 A1 | 4/2016 | Al-Ali et al. |
| 2016/0098137 A1 | 4/2016 | Kim et al. |
| 2016/0103598 A1 | 4/2016 | Al-Ali et al. |
| 2016/0103985 A1 | 4/2016 | Shim et al. |
| 2016/0106367 A1 | 4/2016 | Jorov et al. |
| 2016/0113527 A1 | 4/2016 | Al-Ali |
| 2016/0143548 A1 | 5/2016 | Al-Ali |
| 2016/0154950 A1 | 6/2016 | Nakajima et al. |
| 2016/0157780 A1 | 6/2016 | Rimminen et al. |
| 2016/0166182 A1 | 6/2016 | Al-Ali et al. |
| 2016/0166183 A1 | 6/2016 | Poeze et al. |
| 2016/0196388 A1 | 7/2016 | Lamego |
| 2016/0197436 A1 | 7/2016 | Barker et al. |
| 2016/0213281 A1 | 7/2016 | Eckerbom et al. |
| 2016/0213309 A1 | 7/2016 | Sannholm et al. |
| 2016/0228043 A1 | 8/2016 | O'Neil et al. |
| 2016/0228064 A1 | 8/2016 | Jung et al. |
| 2016/0233632 A1 | 8/2016 | Scruggs et al. |
| 2016/0234944 A1 | 8/2016 | Schmidt et al. |
| 2016/0256058 A1 | 9/2016 | Pham et al. |
| 2016/0256082 A1 | 9/2016 | Ely et al. |
| 2016/0267238 A1 | 9/2016 | Nag |
| 2016/0270735 A1 | 9/2016 | Diab et al. |
| 2016/0283665 A1 | 9/2016 | Sampath et al. |
| 2016/0287090 A1 | 10/2016 | Al-Ali et al. |
| 2016/0287107 A1 | 10/2016 | Szabados et al. |
| 2016/0287181 A1 | 10/2016 | Han et al. |
| 2016/0287786 A1 | 10/2016 | Kiani |
| 2016/0296169 A1 | 10/2016 | McHale et al. |
| 2016/0296173 A1 | 10/2016 | Culbert |
| 2016/0296174 A1 | 10/2016 | Isikman et al. |
| 2016/0310027 A1 | 10/2016 | Han |
| 2016/0310052 A1 | 10/2016 | Al-Ali et al. |
| 2016/0314260 A1 | 10/2016 | Kiani |
| 2016/0324488 A1 | 11/2016 | Olsen |
| 2016/0327984 A1 | 11/2016 | Al-Ali et al. |
| 2016/0331332 A1 | 11/2016 | Al-Ali |
| 2016/0338598 A1 | 11/2016 | Kegasawa |
| 2016/0367173 A1 | 12/2016 | Dalvi et al. |
| 2016/0378069 A1 | 12/2016 | Rothkopf |
| 2016/0378071 A1 | 12/2016 | Rothkopf |
| 2017/0000394 A1 | 1/2017 | Al-Ali et al. |
| 2017/0007134 A1 | 1/2017 | Al-Ali et al. |
| 2017/0007183 A1 | 1/2017 | Dusan et al. |
| 2017/0007198 A1 | 1/2017 | Al-Ali et al. |
| 2017/0010858 A1 | 1/2017 | Prest et al. |
| 2017/0011210 A1 | 1/2017 | Cheong et al. |
| 2017/0014083 A1 | 1/2017 | Diab et al. |
| 2017/0014084 A1 | 1/2017 | Al-Ali et al. |
| 2017/0024748 A1 | 1/2017 | Haider |
| 2017/0042488 A1 | 2/2017 | Muhsin |
| 2017/0046024 A1 | 2/2017 | Dascola et al. |
| 2017/0055851 A1 | 3/2017 | Al-Ali |
| 2017/0055882 A1 | 3/2017 | Al-Ali et al. |
| 2017/0055887 A1 | 3/2017 | Al-Ali |
| 2017/0055896 A1 | 3/2017 | Al-Ali |
| 2017/0074897 A1 | 3/2017 | Mermel et al. |
| 2017/0079594 A1 | 3/2017 | Telfort et al. |
| 2017/0084133 A1 | 3/2017 | Cardinali et al. |
| 2017/0086689 A1 | 3/2017 | Shui et al. |
| 2017/0086723 A1 | 3/2017 | Al-Ali et al. |
| 2017/0086742 A1 | 3/2017 | Harrison-Noonan et al. |
| 2017/0086743 A1 | 3/2017 | Bushnell et al. |
| 2017/0094450 A1 | 3/2017 | Tu et al. |
| 2017/0119262 A1 | 5/2017 | Shim et al. |
| 2017/0143281 A1 | 5/2017 | Olsen |
| 2017/0147774 A1 | 5/2017 | Kiani |
| 2017/0156620 A1 | 6/2017 | Al-Ali et al. |
| 2017/0164884 A1 | 6/2017 | Culbert et al. |
| 2017/0172435 A1 | 6/2017 | Presura |
| 2017/0172476 A1 | 6/2017 | Schilthuizen |
| 2017/0173632 A1 | 6/2017 | Al-Ali |
| 2017/0187146 A1 | 6/2017 | Kiani et al. |
| 2017/0188919 A1 | 7/2017 | Al-Ali et al. |
| 2017/0196464 A1 | 7/2017 | Jansen et al. |
| 2017/0196470 A1 | 7/2017 | Lamego et al. |
| 2017/0202505 A1 | 7/2017 | Kirenko et al. |
| 2017/0209095 A1 | 7/2017 | Wagner et al. |
| 2017/0215743 A1 | 8/2017 | Meer et al. |
| 2017/0224262 A1 | 8/2017 | Al-Ali |
| 2017/0228516 A1 | 8/2017 | Sampath et al. |
| 2017/0245790 A1 | 8/2017 | Al-Ali et al. |
| 2017/0248446 A1 | 8/2017 | Gowreesunker et al. |
| 2017/0251974 A1 | 9/2017 | Shreim et al. |
| 2017/0251975 A1 | 9/2017 | Shreim et al. |
| 2017/0258403 A1 | 9/2017 | Abdul-Hafiz et al. |

(56) References Cited

U.S. PATENT DOCUMENTS

| | | |
|---|---|---|
| 2017/0273619 A1 | 9/2017 | Alvarado et al. |
| 2017/0281024 A1 | 10/2017 | Narasimhan et al. |
| 2017/0293727 A1 | 10/2017 | Klaassen et al. |
| 2017/0311851 A1 | 11/2017 | Schurman et al. |
| 2017/0311891 A1 | 11/2017 | Kiani et al. |
| 2017/0325698 A1 | 11/2017 | Allec et al. |
| 2017/0325728 A1 | 11/2017 | Al-Ali et al. |
| 2017/0325744 A1 | 11/2017 | Allec et al. |
| 2017/0332976 A1 | 11/2017 | Al-Ali |
| 2017/0340209 A1 | 11/2017 | Klaassen et al. |
| 2017/0340219 A1 | 11/2017 | Sullivan et al. |
| 2017/0340293 A1 | 11/2017 | Al-Ali et al. |
| 2017/0347885 A1 | 12/2017 | Tan et al. |
| 2017/0354332 A1 | 12/2017 | Lamego |
| 2017/0354795 A1 | 12/2017 | Blahnik et al. |
| 2017/0358239 A1 | 12/2017 | Arney et al. |
| 2017/0358240 A1 | 12/2017 | Blahnik et al. |
| 2017/0358242 A1 | 12/2017 | Thompson et al. |
| 2017/0360306 A1 | 12/2017 | Narasimhan et al. |
| 2017/0360310 A1 | 12/2017 | Kiani |
| 2017/0366657 A1 | 12/2017 | Thompson et al. |
| 2017/0367632 A1 | 12/2017 | Al-Ali et al. |
| 2018/0008146 A1 | 1/2018 | Al-Ali et al. |
| 2018/0013562 A1 | 1/2018 | Haider et al. |
| 2018/0014752 A1 | 1/2018 | Al-Ali et al. |
| 2018/0014781 A1 | 1/2018 | Clavelle et al. |
| 2018/0025287 A1 | 1/2018 | Mathew et al. |
| 2018/0028124 A1 | 2/2018 | Al-Ali et al. |
| 2018/0042556 A1 | 2/2018 | Shahparnia et al. |
| 2018/0049656 A1 | 2/2018 | Paulussen et al. |
| 2018/0049694 A1 | 2/2018 | Singh Alvarado et al. |
| 2018/0050235 A1 | 2/2018 | Tan et al. |
| 2018/0055375 A1 | 3/2018 | Martinez et al. |
| 2018/0055385 A1 | 3/2018 | Al-Ali |
| 2018/0055390 A1 | 3/2018 | Kiani et al. |
| 2018/0055430 A1 | 3/2018 | Diab et al. |
| 2018/0055439 A1 | 3/2018 | Pham et al. |
| 2018/0056129 A1 | 3/2018 | Narasimha Rao et al. |
| 2018/0064381 A1 | 3/2018 | Shakespeare et al. |
| 2018/0069776 A1 | 3/2018 | Lamego et al. |
| 2018/0070867 A1 | 3/2018 | Smith et al. |
| 2018/0078151 A1 | 3/2018 | Allec et al. |
| 2018/0078182 A1 | 3/2018 | Chen et al. |
| 2018/0082767 A1 | 3/2018 | Al-Ali et al. |
| 2018/0085068 A1 | 3/2018 | Telfort |
| 2018/0087937 A1 | 3/2018 | Al-Ali et al. |
| 2018/0103874 A1 | 4/2018 | Lee et al. |
| 2018/0103905 A1 | 4/2018 | Kiani |
| 2018/0110469 A1 | 4/2018 | Maani et al. |
| 2018/0110478 A1 | 4/2018 | Al-Ali |
| 2018/0116575 A1 | 5/2018 | Perea et al. |
| 2018/0125368 A1 | 5/2018 | Lamego et al. |
| 2018/0125430 A1 | 5/2018 | Al-Ali et al. |
| 2018/0125445 A1 | 5/2018 | Telfort et al. |
| 2018/0130325 A1 | 5/2018 | Kiani et al. |
| 2018/0132769 A1 | 5/2018 | Weber et al. |
| 2018/0132770 A1 | 5/2018 | Lamego |
| 2018/0146901 A1 | 5/2018 | Al-Ali et al. |
| 2018/0146902 A1 | 5/2018 | Kiani et al. |
| 2018/0153418 A1 | 6/2018 | Sullivan et al. |
| 2018/0153442 A1 | 6/2018 | Eckerbom et al. |
| 2018/0153446 A1 | 6/2018 | Kiani |
| 2018/0153447 A1 | 6/2018 | Al-Ali et al. |
| 2018/0153448 A1 | 6/2018 | Weber et al. |
| 2018/0161499 A1 | 6/2018 | Al-Ali et al. |
| 2018/0164853 A1 | 6/2018 | Myers et al. |
| 2018/0168491 A1 | 6/2018 | Al-Ali et al. |
| 2018/0174679 A1 | 6/2018 | Sampath et al. |
| 2018/0174680 A1 | 6/2018 | Sampath et al. |
| 2018/0177401 A1 | 6/2018 | Yang et al. |
| 2018/0182484 A1 | 6/2018 | Sampath et al. |
| 2018/0184917 A1 | 7/2018 | Kiani |
| 2018/0192924 A1 | 7/2018 | Al-Ali |
| 2018/0192953 A1 | 7/2018 | Shreim et al. |
| 2018/0192955 A1 | 7/2018 | Al-Ali et al. |
| 2018/0196514 A1 | 7/2018 | Allec et al. |
| 2018/0199871 A1 | 7/2018 | Pauley et al. |
| 2018/0206795 A1 | 7/2018 | Al-Ali |
| 2018/0206815 A1 | 7/2018 | Telfort |
| 2018/0213583 A1 | 7/2018 | Al-Ali |
| 2018/0214031 A1 | 8/2018 | Kiani et al. |
| 2018/0214090 A1 | 8/2018 | Al-Ali et al. |
| 2018/0218792 A1 | 8/2018 | Muhsin et al. |
| 2018/0225960 A1 | 8/2018 | Al-Ali et al. |
| 2018/0228414 A1 | 8/2018 | Shao et al. |
| 2018/0235542 A1 | 8/2018 | Yun et al. |
| 2018/0238718 A1 | 8/2018 | Dalvi |
| 2018/0238734 A1 | 8/2018 | Hotelling et al. |
| 2018/0242853 A1 | 8/2018 | Al-Ali |
| 2018/0242921 A1 | 8/2018 | Muhsin et al. |
| 2018/0242923 A1 | 8/2018 | Al-Ali et al. |
| 2018/0242924 A1 | 8/2018 | Barker et al. |
| 2018/0242926 A1 | 8/2018 | Muhsin et al. |
| 2018/0247353 A1 | 8/2018 | Al-Ali et al. |
| 2018/0247712 A1 | 8/2018 | Muhsin et al. |
| 2018/0249933 A1 | 9/2018 | Schurman et al. |
| 2018/0253947 A1 | 9/2018 | Muhsin et al. |
| 2018/0256087 A1 | 9/2018 | Al-Ali et al. |
| 2018/0256113 A1 | 9/2018 | Weber et al. |
| 2018/0279956 A1 | 10/2018 | Waydo et al. |
| 2018/0285094 A1 | 10/2018 | Housel et al. |
| 2018/0289325 A1 | 10/2018 | Poeze et al. |
| 2018/0289337 A1 | 10/2018 | Al-Ali et al. |
| 2018/0296161 A1 | 10/2018 | Shreim et al. |
| 2018/0300919 A1 | 10/2018 | Muhsin et al. |
| 2018/0310822 A1 | 11/2018 | Indorf et al. |
| 2018/0310823 A1 | 11/2018 | Al-Ali et al. |
| 2018/0317826 A1 | 11/2018 | Muhsin et al. |
| 2018/0317841 A1 | 11/2018 | Novak, Jr. |
| 2018/0333053 A1 | 11/2018 | Verkruijsse et al. |
| 2018/0333055 A1 | 11/2018 | Lamego et al. |
| 2018/0333087 A1 | 11/2018 | Al-Ali |
| 2018/0360326 A1 | 12/2018 | Lee et al. |
| 2018/0360373 A1 | 12/2018 | Aarts et al. |
| 2019/0000317 A1 | 1/2019 | Muhsin et al. |
| 2019/0000362 A1 | 1/2019 | Kiani et al. |
| 2019/0015023 A1 | 1/2019 | Monfre |
| 2019/0021638 A1 | 1/2019 | Al-Ali et al. |
| 2019/0029574 A1 | 1/2019 | Schurman et al. |
| 2019/0029578 A1 | 1/2019 | Al-Ali et al. |
| 2019/0038143 A1 | 2/2019 | Al-Ali |
| 2019/0058280 A1 | 2/2019 | Al-Ali et al. |
| 2019/0058281 A1 | 2/2019 | Al-Ali et al. |
| 2019/0069813 A1 | 3/2019 | Al-Ali |
| 2019/0069814 A1 | 3/2019 | Al-Ali |
| 2019/0076028 A1 | 3/2019 | Al-Ali et al. |
| 2019/0082979 A1 | 3/2019 | Al-Ali et al. |
| 2019/0090748 A1 | 3/2019 | Al-Ali |
| 2019/0090760 A1 | 3/2019 | Kinast et al. |
| 2019/0090764 A1 | 3/2019 | Al-Ali |
| 2019/0104973 A1 | 4/2019 | Poeze et al. |
| 2019/0110719 A1 | 4/2019 | Poeze et al. |
| 2019/0117070 A1 | 4/2019 | Muhsin et al. |
| 2019/0117139 A1 | 4/2019 | Al-Ali et al. |
| 2019/0117140 A1 | 4/2019 | Al-Ali et al. |
| 2019/0117141 A1 | 4/2019 | Al-Ali |
| 2019/0117930 A1 | 4/2019 | Al-Ali |
| 2019/0122763 A1 | 4/2019 | Sampath et al. |
| 2019/0133525 A1 | 5/2019 | Al-Ali et al. |
| 2019/0142283 A1 | 5/2019 | Lamego et al. |
| 2019/0142344 A1 | 5/2019 | Telfort et al. |
| 2019/0150800 A1 | 5/2019 | Poeze et al. |
| 2019/0150856 A1 | 5/2019 | Kiani et al. |
| 2019/0167114 A1 | 6/2019 | Islam |
| 2019/0167161 A1 | 6/2019 | Al-Ali et al. |
| 2019/0175019 A1 | 6/2019 | Al-Ali et al. |
| 2019/0192076 A1 | 6/2019 | McHale et al. |
| 2019/0196411 A1 | 6/2019 | Yuen |
| 2019/0324593 A1 | 10/2019 | Chung et al. |

(56) References Cited

U.S. PATENT DOCUMENTS

| | | | |
|---|---|---|---|
| 2020/0000345 A1 | 1/2020 | Connor | |
| 2020/0121941 A1 | 4/2020 | Kwon et al. | |

FOREIGN PATENT DOCUMENTS

| | | |
|---|---|---|
| CN | 1482448 | 3/2004 |
| CN | 100518630 C | 7/2009 |
| CN | 101484065 | 7/2009 |
| CN | 101564290 | 10/2009 |
| CN | 302687306 S | 12/2013 |
| CN | 103906468 | 7/2014 |
| CN | 203732900 | 7/2014 |
| CN | 302942795 S | 9/2014 |
| CN | 302972990 S | 10/2014 |
| CN | 302864470 | 11/2014 |
| CN | 303285726 S | 7/2015 |
| CN | 303296619 S | 7/2015 |
| CN | 303306604 S | 7/2015 |
| CN | 303327831 S | 8/2015 |
| CN | 303518893 S | 12/2015 |
| CN | 205041396 | 2/2016 |
| CN | 303646405 S | 4/2016 |
| CN | 303737075 S | 7/2016 |
| CN | 106236051 | 12/2016 |
| CN | 104181809 | 1/2017 |
| CN | 304027493 S | 2/2017 |
| CN | 106527106 | 3/2017 |
| CN | 304385323 S | 12/2017 |
| CN | 304471666 S | 1/2018 |
| CN | 105379306 | 2/2020 |
| EM | 001383434-0008 | 9/2013 |
| EM | 001383434-0009 | 9/2013 |
| EM | 002743575-0001 | 7/2015 |
| EM | 004428274-0003 | 10/2017 |
| EM | 005940459-0005 | 12/2018 |
| EM | 005940459-0011 | 12/2018 |
| EM | 005940459-0013 | 12/2018 |
| EM | 005940459-0014 | 12/2018 |
| EM | 005940459-0015 | 12/2018 |
| EM | 006302279-0001 | 3/2019 |
| EM | 006302279-0002 | 3/2019 |
| EM | 007127113-0001 | 10/2019 |
| EP | 0 505 627 | 9/1992 |
| EP | 0 630 208 | 12/1994 |
| EP | 0 770 349 | 5/1997 |
| EP | 0 781 527 | 7/1997 |
| EP | 0 880 936 | 12/1998 |
| EP | 0 985 373 | 3/2000 |
| EP | 1 080 683 | 3/2001 |
| EP | 1 124 609 | 8/2001 |
| EP | 1 213 037 | 6/2002 |
| EP | 2 277 440 | 1/2011 |
| EP | 14163114.3 | 4/2014 |
| EP | 2 194 842 | 4/2015 |
| EP | 3 015 062 | 5/2016 |
| EP | 3316779 | 5/2018 |
| EP | 3 430 980 | 1/2019 |
| EP | 3 488 776 | 5/2019 |
| EP | 3 626 159 | 3/2020 |
| EP | 3 033 992 | 4/2020 |
| GB | 2243691 | 11/1991 |
| GB | 4032616 | 1/2014 |
| JP | S57-037438 | 3/1982 |
| JP | H06-66633 | 9/1994 |
| JP | 09-173322 | 7/1997 |
| JP | H09257508 | 10/1997 |
| JP | H10314133 | 12/1998 |
| JP | H1170086 | 3/1999 |
| JP | 2919326 | 7/1999 |
| JP | 2004-298606 | 10/2004 |
| JP | 2004-337605 | 12/2004 |
| JP | 2004-344668 | 12/2004 |
| JP | 2005-270543 | 10/2005 |
| JP | 2006-102159 | 4/2006 |
| JP | 2006-288835 | 10/2006 |
| JP | 2008-119026 | 5/2008 |
| JP | 2008-126017 | 6/2008 |
| JP | 2009-106373 | 5/2009 |
| JP | 2010-136921 | 6/2010 |
| JP | D1400735 | 11/2010 |
| JP | 2011-147746 | 8/2011 |
| JP | D1436448 | 3/2012 |
| JP | 5056867 | 10/2012 |
| JP | 2013-515528 | 5/2013 |
| JP | 2013-118978 | 6/2013 |
| JP | 2013-212315 | 10/2013 |
| JP | D1489271 | 12/2013 |
| JP | 2015-112488 | 6/2015 |
| JP | 2016-054822 | 4/2016 |
| JP | 2016-154754 | 9/2016 |
| JP | D1568369 | 12/2016 |
| JP | 2018-524073 | 8/2018 |
| KR | 20-0195400 | 9/2000 |
| KR | 10-2016-0089718 | 11/2003 |
| KR | 10-2006-0083552 | 7/2006 |
| KR | 10-2006-0111159 | 10/2006 |
| KR | 10-2007-0011685 | 1/2007 |
| KR | 10-2007-0058900 | 6/2007 |
| KR | 10-2007-0102089 | 10/2007 |
| KR | 10-2007-0056925 | 4/2008 |
| KR | 10-2008-0048010 | 5/2008 |
| KR | 20100091592 | 8/2010 |
| KR | 30-0645410 | 5/2012 |
| KR | 10-2013-0107833 | 10/2013 |
| KR | 30-0740673 | 4/2014 |
| KR | 30-0817671 | 9/2015 |
| KR | 10-2016-0041623 | 4/2016 |
| KR | 10-2016-0044811 | 4/2016 |
| KR | 10-2016-0058476 | 5/2016 |
| KR | 10-2016-0069623 | 8/2016 |
| KR | 10-2016-0096902 | 8/2016 |
| KR | 10-2017-0049279 | 5/2017 |
| KR | 10-2018-0038206 | 4/2018 |
| KR | 10-2019-0115313 | 10/2019 |
| KR | 10-2136836 | 8/2020 |
| KR | 20200093247 | 8/2020 |
| WO | WO 82/000088 | 1/1982 |
| WO | WO 94/021173 | 9/1994 |
| WO | WO 94/023643 | 10/1994 |
| WO | WO 95/000070 | 1/1995 |
| WO | WO 96/027325 | 9/1996 |
| WO | WO 97/000923 | 1/1997 |
| WO | WO 97/009923 | 3/1997 |
| WO | WO 96/063883 | 12/1999 |
| WO | WO 99/063883 | 12/1999 |
| WO | WO 00/028892 | 5/2000 |
| WO | WO 01/017421 | 3/2001 |
| WO | WO 02/028274 | 4/2002 |
| WO | WO 03/031961 | 4/2003 |
| WO | WO 2004/082472 | 9/2004 |
| WO | WO 2005/092182 | 10/2005 |
| WO | WO 2006/113070 | 10/2006 |
| WO | WO 2008/040736 | 4/2008 |
| WO | WO 2008/107238 | 9/2008 |
| WO | WO 2008/133394 | 11/2008 |
| WO | WO 2009/001988 | 12/2008 |
| WO | WO 2009/137524 | 11/2009 |
| WO | WO 2011/051888 | 5/2011 |
| WO | WO 2011/069122 | 6/2011 |
| WO | WO 2011/076886 | 6/2011 |
| WO | WO 2012/140559 | 10/2012 |
| WO | WO 2013/027357 | 2/2013 |
| WO | WO 2013/030744 | 3/2013 |
| WO | WO 2013/066642 | 5/2013 |
| WO | WO 2013/076656 | 5/2013 |
| WO | WO 2013/089712 | 6/2013 |
| WO | WO 2013/106607 | 7/2013 |
| WO | WO 2013/124750 | 8/2013 |
| WO | WO 2013/181368 | 12/2013 |
| WO | WO 2014/018447 | 1/2014 |
| WO | WO D083678-002 | 6/2014 |
| WO | WO 2014/115075 | 7/2014 |
| WO | WO 2014/153200 | 9/2014 |
| WO | WO 2014/178793 | 11/2014 |

(56)         References Cited

FOREIGN PATENT DOCUMENTS

| WO | WO 2014/184447 | 11/2014 |
| WO | WO 2015/034149 | 3/2015 |
| WO | WO D086018-0001 | 3/2015 |
| WO | WO D086018-0002 | 3/2015 |
| WO | WO 2015/049108 | 4/2015 |
| WO | WO D086693-004 | 7/2015 |
| WO | WO 2015/116111 | 8/2015 |
| WO | WO 2015/150199 | 10/2015 |
| WO | WO 2015/187732 | 12/2015 |
| WO | WO 2016/066312 | 5/2016 |
| WO | WO 2017/004260 | 1/2017 |
| WO | WO 2017/165532 | 9/2017 |

OTHER PUBLICATIONS

Appendix as filed in Reexamination U.S. Appl. No. 90/019,45, filed Mar. 25, 2024 in 89 pages.

Statement Accompanying Reexam Request as filed in Reexamination U.S. Appl. No. 90/019,457, filed Mar. 25, 2024 in 59 pages.

Reexamination Request as filed in Reexamination U.S. Appl. No. 90/019,457, filed Mar. 25, 2024 in 4 pages.

Interview Summary as received in Reexamination U.S. Appl. No. 90/019,457, filed Mar. 29, 2024 in 2 pages.

Order Granting Request for Ex Parte Reexamination as received in Reexamination U.S. Appl. No. 90/019,457, filed Apr. 19, 2024 in 20 pages.

U.S. Appl. No. 61/932,258, filed Jan. 28, 2014, Park et al.

U.S. Appl. No. 61/976,388, filed Apr. 7, 2014, Fei.

Bacchillone, et al. "A flexible home gateway system for telecare of patients affected by chronic heart failure," APL_DEL00032311, 2011, in 4 pages.

Bailey, et al. "Development of a Remote Pulse Oximeter," APL_DEL00032315, 2010, in 91 pages.

Chang, et al. "Microlens array diffuser for a light-emitting diode backlight system," APL_DEL00030110, 2+B256006, in 4 pages.

Donati, et al. "A flexible home monitoring platform for patients affected by chronic heart failure directly integrated with the remote Hospital Information System," APL_DEL00032456, 2011, in 8 pages.

Fantini, et al. "Frequency-domain multichannel optical detector for noninvasive tissue spectroscopy and oximetry," APL_DEL00037609, 1995, in 12 pages.

Lin, et al. "Wireless PDA-Based Physiological Monitoring System for Patient Transport," APL_DEL00031220, Dec. 2004, in 9 pages.

Moyle, "Pulse Oximetry," APL_DEL00031253, 2002, in 192 pages.

Nogawa, et al. "New hybrid reflectance optical pulse oximetry sensor for lower oxygen saturation measurement and for broader clinical application," APL_DEL00037781, 1997, in 11 pages.

Rodrigues, et al. "Using Discovery and Monitoring Services to Support Context-Aware Remote Assisted Living Applications," APL_DEL00036886, 2009, in 6 pages.

Tablado, et al. "A Flexible Data Processing Technique for a Tele-assistance System of Elderly People," APL_DEL00032254, 2004, in 24 pages.

"A New Family of Sensors for Pulse Oximetry," Hewlett-Packard Journal, Feb. 1997 (APL_DEL00037653), in 17 pages. Apple alleges that this reference has a prior art date of 1997.

"A Technology Overview of the Nellcor OxiMax Pulse Oximetry System," Nellcor Technical Staff, 2003 (APL_DEL00031781, APL_DEL00037976), in 8 pages. Apple alleges that this reference has a prior art date of 2003.

"Masimo Signal Extraction Technology," Masimo Corp., 2001 (APL_DEL00037764), in 8 pages. Apple alleges that this reference has a prior art date of 2003.

"Masimo Signal Extraction Technology: Technical Bulletin 1," Masimo Corp., 2001 (APL_DEL00037757), in 7 pages. Apple alleges that this reference has a prior art date of 2003.

"Non-Invasive Cardiac Output Monitor Model 7300: User's Manual," Novametrix, 2001 (APL_DEL00031974), in 100 pages. Apple alleges that this reference has a prior art date of 2001.

"NPB-195 Pulse Oximeter: Home Use Guide," Nellcor, 1997 (APL_DEL00032149), in 105 pages. Apple alleges that this reference has a prior art date of 1999.

"NPB-195 Pulse Oximeter: Operator's Manual," Mallinckrodt, 1999 (APL_DEL00032074), in 75 pages. Apple alleges that this reference has a prior art date of 1999.

"OxiMax N-595 Pulse Oximeter Operator's Manual," Nellcor, 2002 (APL_DEL00031597, APL_DEL00037792), in 184 pages. Apple alleges that this reference has a prior art date of 2003.

"Oxinet II Monitoring System Operator's Manual," Nellcor, 2002 (APL_DEL00031789), in 132 pages. Apple alleges that this reference has a prior art date of 2003.

"Oxinet III Central Station and Paging System," Nellcor, 2003 (APL_DEL00031921), in 2 pages. Apple alleges that this reference has a prior art date of 2003.

"Oxinet III Service Manual," Nellcor, 2005 (APL_DEL00031535), in 62 pages. Apple alleges that this reference has a prior art date of 2003.

"Pulse Oximetry Sensors: LNOP & NR," Masimo SET, 2003 (APL_DEL00037755), in 2 pages. Apple alleges that this reference has a prior art date of 2003.

"Radical Signal Extraction Pulse Oximeter: Operator's Manual," Masimo, 2001 (APL_DEL00034347), in 78 pages. Apple alleges that this reference has a prior art date of 2001.

"Sotera Wireless," Tuck School of Business at Dartmouth: Center for Digital Strategies Case Series, Sep. 4, 2012 (APL_DEL00037109), in 20 pages. Apple alleges that this reference has a prior art date of 2011.

A Decision Support Service Platform for Neurodegenerative Disease Patients, Sixth International Conference on Networking and Services, 2010 (APL_DEL00034343), in 4 pages. Apple alleges that this reference has a prior art date of 2010.

Android-based Healthcare Smartphone Packed with Medical Sensors, Jul. 5, 2012 (APL_DEL00038072), in 3 pages. Apple alleges that this reference has a prior art date of 2012.

CODE-STAT 10 Basic Annotation Guide, 2015 (APL_DEL00032565), in 62 pages. Apple alleges that this reference has a prior art date of 2011.

CODE-STAT data review software and service, Jun. 5, 2023 (APL_DEL00032627), in 4 pages. Apple alleges that this reference has a prior art date of 2011.

DC Rainmaker, Fitbit Surge In-Depth Review, Jan. 20, 2015 ("Surge Review") (APL_DEL00030150), in 109 pages. Apple alleges that this reference has a prior art date of May 2015.

Dynamic Adaptive Remote Health Monitoring for Patients with Chronic Disease, University of California, Los Angeles, 2012 (APL_DEL00038075), in 127 pages. Apple alleges that this reference has a prior art date of 2012.

Fitbit, Fitbit Surge Fitness Super Watch User Manual Version 1.0 ("Surge Manual") (APL_DEL00030259), in 49 pages. Apple alleges that this reference has a prior art date of May 2015.

Fitbit's New Fitness Watch Can Display Your Calls And Track Your Location While You Run, Oct. 27, 2014 ("Fitbit's New Fitness Watch") (APL_DEL00030308), in 5 pages. Apple alleges that this reference has a prior art date of May 2015.

Hamamatsu, "Lens for Side-on Type Photomultiplier Tubes" (Mar. 1999) (APL_DEL00037641), in 4 pages. Apple alleges that this reference has a prior art date of Mar. 1999.

How ViSi Mobile Can Help With Infectious Disease / Sotera ViSi Mobile Brochures (APL_DEL00036979), in 1 page. Apple alleges that this reference has a prior art date of 2011.

https://www.stryker.com/us/en/emergencycare/products/lifepak-15.html (APL_DEL00033792), in 6 pages. Apple alleges that this reference has a prior art date of 2011.

Human-Centered Phone Oximeter Interface Design for the Operating Room, Proceedings of the International Conference on Health Informatics, SciTePress (APL_DEL00032489), in 6 pages. Apple alleges that this reference has a prior art date of 2011.

Ideal Life SpO2 Manager, 2011 (APL_DEL00038204), in 2 pages. Apple alleges that this reference has a prior art date of 2012.

(56) References Cited

OTHER PUBLICATIONS

IntelliVue MX40 Brochures, Mar. 2016 (APL_DEL00036603), in 8 pages. Apple alleges that this reference has a prior art date of Feb. 2012.

IntelliVue MX40 Brochures (APL_DEL00036821), in 3 pages. Apple alleges that this reference has a prior art date of Feb. 2012.

IntelliVue MX40 Brochures, Jan. 2020 (APL_DEL00036861), in 17 pages. Apple alleges that this reference has a prior art date of Feb. 2012.

IntelliVue MX40 Brochures (APL_DEL00036878), in 8 pages. Apple alleges that this reference has a prior art date of Feb. 2012.

IntelliVue MX40 Installation and Service, Jun. 2012 (APL_DEL00035983), in 158 pages. Apple alleges that this reference has a prior art date of Feb. 2012.

IntelliVue MX40 Instructions for Use, Feb. 2012 (APL_DEL00036141), in 246 pages. Apple alleges that this reference has a prior art date of Feb. 2012. [Uploaded in 2 parts].

IntelliVue MX40 Instructions for Use, Jun. 2011 (APL_DEL00036611), in 210 pages. Apple alleges that this reference has a prior art date of Feb. 2012.

IntelliVue MX40 with Masimo SET Reusable Adapter and Patient Cables Instructions for Use, 2020 (APL_DEL00036387), in 206 pages. Apple alleges that this reference has a prior art date of Feb. 2012.

LifePak 15 Monitor Defibrillator Operating Instructions, Jun. 2015 (APL_DEL00032631), in 284 pages. Apple alleges that this reference has a prior art date of 2011. [Uploaded in 2 parts].

LifePak 15 Monitor Defibrillator Power Module Upgrade (APL_DEL00032915), in 52 pages. Apple alleges that this reference has a prior art date of 2011.

LifePak 15 Monitor Defibrillator Service Manuals, Mar. 2019 (APL_DEL00032967), in 507 pages. Apple alleges that this reference has a prior art date of 2011. [Uploaded in 2 parts].

LifePak 15 Monitor Defibrillator Service Manuals, Jun. 2015 (APL_DEL00033798), in 527 pages. Apple alleges that this reference has a prior art date of 2011. [Uploaded in 2 parts].

LifePak 15 Operating Instructions, Jan. 2019 (APL_DEL00033474), in 318 pages. Apple alleges that this reference has a prior art date of 2011. [Uploaded in 3 parts].

LifeWatch V User Manual, 2012 (APL_DEL00038208), in 136 pages. Apple alleges that this reference has a prior art date of 2012.

LifeWatch V, A smartphone that connects to you, Jul. 7, 2012 (APL_DEL00038344), in 1 page. Apple alleges that this reference has a prior art date of 2012.

Lucas 3 Quick User Guide (APL_DEL00034325), 2020, in 5 pages. Apple alleges that this reference has a prior art date of 2011.

Microsoft HealthVault Drivers—Installation Quick Start Guide (APL_DEL00034971), in 4 pages. Apple alleges that this reference has a prior art date of 2008.

Microsoft HealthVault Service Specification, Mar. 27, 2009 (APL_DEL00034580), in 391 pages. Apple alleges that this reference has a prior art date of 2008.

Model 3150 WristOx2 Operator's Manual and 3150SC USB Cable Driver Software (APL_DEL00035230), in 699 pages. Apple alleges that this reference has a prior art date of 2011. [Uploaded in 6 parts].

Nellcor N-3000 Pulse Oximeter Service Manual, 1996 (APL_DEL00034470), in 110 pages. Apple alleges that this reference has a prior art date of 1996.

Nonin Comparative Accuracy Testing of Nonin PureSAT, Nov. 8, 2004 (APL_DEL00034975), in 6 pages. Apple alleges that this reference has a prior art date of 2008.

Nonin nVision Operator's Manual (APL_DEL00035127), 2017, in 54 pages. Apple alleges that this reference has a prior art date of 2008.

Nonin nVision SpO2 Data Management Software (APL_DEL00035111), 2009, in 4 pages. Apple alleges that this reference has a prior art date of 2008.

Nonin nVision User Guide (APL_DEL00035018), 2014, in 89 pages. Apple alleges that this reference has a prior art date of 2008.

Nonin OEM Family Brochure (APL_DEL00035115), 2005, in 12 pages. Apple alleges that this reference has a prior art date of 2008.

Nonin Onyx II 9560 User Manual (APL_DEL00035014), 2008, in 4 pages. Apple alleges that this reference has a prior art date of 2008.

Nonin Onyx II Model 9560 Finger Pulse Oximeter Instructions for Use—English (APL_DEL00034981), 2012, in 9 pages. Apple alleges that this reference has a prior art date of 2008.

Nonin Pulse Oximeter Avant 4100 Service Manual (APL_DEL00035929), 2005, in 44 pages. Apple alleges that this reference has a prior art date of 2008.

Nonin Sample nVision Report (APL_DEL00035107), in 4 pages. Apple alleges that this reference has a prior art date of 2008.

Nonin WristOx 3100 Operator's Manual (APL_DEL00035187), 2005, in 43 pages. Apple alleges that this reference has a prior art date of 2011.

Nonin WristOx2 3150 Bluetooth Connection Tutorial (APL_DEL00034990), in 20 pages. Apple alleges that this reference has a prior art date of 2011.

OxiMax N-595 Pulse Oximeter Home Use Guide APL_DEL00031445), in 90 pages. Apple alleges that this reference has a prior art date of 2003.

PAS: A Wireless-Enabled, Cell-Phone-Incorporated Personal Assistance System for Independent and Assisted Living, 28th International Conference on Distributed Computing Systems, 2008 (APL_DEL00035973), in 10 pages. Apple alleges that this reference has a prior art date of 2008.

Philips IntelliVue Information Center iX Brochures (APL_DEL00036593), 2014, in 2 pages. Apple alleges that this reference has a prior art date of Feb. 2012.

Philips IntelliVue Information Center iX Brochures (APL_DEL00036595), Nov. 2015, in 8 pages. Apple alleges that this reference has a prior art date of Feb. 2012.

Philips IntelliVue Information Center iX Brochures (APL_DEL00036824), Sep. 2019, in 16 pages. Apple alleges that this reference has a prior art date of Feb. 2012.

Philips IntelliVue Information Center iX Brochures, Jun. 2015 (APL_DEL00036842), in 4 pages. Apple alleges that this reference has a prior art date of Feb. 2012.

Philips IntelliVue Information Center iX Brochures, Apr. 2015 (APL_DEL00036846), in 4 pages. Apple alleges that this reference has a prior art date of Feb. 2012.

Philips IntelliVue Information Center iX Brochures, Jun. 2015 (APL_DEL00036850), in 4 pages. Apple alleges that this reference has a prior art date of Feb. 2012.

Philips IntelliVue Information Center iX Brochures, Jun. 2022 (APL_DEL00036854), in 7 pages. Apple alleges that this reference has a prior art date of Feb. 2012.

Philips IntelliVue Smart-Hopping Network Product Website (APL_DEL00036840), in 2 pages. Apple alleges that this reference has a prior art date of Feb. 2012.

Physio-Control CODE-STAT 10.0 Data Review Software (APL_DEL00034330), in 2 pages. Apple alleges that this reference has a prior art date of 2011.

Sanofi-aventis and AgaMatrix Unveil iBGStar Plug-In Glucose Meter for the iPhone, Medgadget, Sep. 21, 2010 (APL_DEL00038345), in 4 pages. Apple alleges that this reference has a prior art date of 2010.

Sanofi-aventis to launch blood glucose monitoring devices, PharmaBiz.com, Sep. 22, 2010 (APL_DEL00038349), in 2 pages. Apple alleges that this reference has a prior art date of 2010.

Santa Barbara Cottage Hospital, Nonin's Onyx II Fingertip Pulse Oximeter, 2007 (APL_DEL00035181), in 4 pages. Apple alleges that this reference has a prior art date of 2008.

Sotera ViSi Mobile Brochures, Oct. 9, 2013 (APL_DEL00036984), in 2 pages. Apple alleges that this reference has a prior art date of 2011.

Sotera ViSi Mobile Brochures (APL_DEL00037129), in 6 pages. Apple alleges that this reference has a prior art date of 2011.

Sotera ViSi Mobile Brochures (APL_DEL00037305), Aug. 21, 2012, in 1 page. B258.

Sotera ViSi Mobile Brochures, 2018 (APL_DEL00037313), in 2 pages. Apple alleges that this reference has a prior art date of 2011.

(56)                    References Cited

OTHER PUBLICATIONS

Sotera ViSi Mobile Monitoring System Technical Reference Manual, Jul. 2015 (APL_DEL00036993), in 116 pages. Apple alleges that this reference has a prior art date of 2011.

Sotera ViSi Mobile Monitoring System User Manual, Aug. 2012 (APL_DEL00037135), in 170 pages. Apple alleges that this reference has a prior art date of 2011.

Sotera ViSi Mobile Technical Specifications, Oct. 9, 2013 (APL_DEL00036986), in 7 pages. Apple alleges that this reference has a prior art date of 2011.

SpO2 Accuracy of PureSAT Signal Processing Technology—The Onyx II, Aug. 8, 2006 (APL_DEL00035185), in 2 pages. Apple alleges that this reference has a prior art date of 2008.

ViSi Mobile Monitoring System 510(k) Summary, 2013 (APL_DEL00036980), in 4 pages. Apple alleges that this reference has a prior art date of 2011.

ViSi Mobile System General Information (APL_DEL00037307), in 6 pages. Apple alleges that this reference has a prior art date of 2011.

Wanda B.: Weight and Activity with Blood Pressure Monitoring System for Heart Failure Patients, 2010 (APL_DEL00038351), in 7 pages. Apple alleges that this reference has a prior art date of 2012.

Wayback Machine, Fitbit Surge Fitness Super Watch User Manual Version 1.0, May 2015 ("Wayback Machine: Fitbit Surge") (APL_DEL00030689), in 1 page. Apple alleges that this reference has a prior art date of May 2015.

WristOx2, Model 3150 Wrist-worn Pulse Oximeter, 2011 (APL_DEL00035010), in 2 pages. Apple alleges that this reference has a prior art date of 2011.

WristOx2, Model 3150 Wrist-worn Pulse Oximeter, 2011 (APL_DEL00035012), in 2 pages. Apple alleges that this reference has a prior art date of 2011.

Screen captures from YouTube video clip entitled "LifeWatch V—Blood Oxygen Saturation Level Test Tutorial," in 3 pages, uploaded on Jul. 8, 2013 by user "LifeWatchTech". Retrieved from Internet: <https://www.youtube.com/watch?v=68UHtoo1KlY>. Corresponds to "LifeWatch V, Blood Oxygen Saturation Level Test Tutorial" (APL_DEL00038207). Apple alleges that this reference has a prior art date of 2012.

Screen captures from YouTube video clip entitled "LifeWatch V—A Smartphone that Connects to You," in 9 pages, uploaded on Jul. 4, 2012 by user "LifeWatchTech". Retrieved from Internet: <https://www.youtube.com/watch?v=A75GggZSWgc>. Corresponds to "LifeWatch V, A smartphone that connects to you" (APL_DEL00038206). Apple alleges that this reference has a prior art date of 2012.

Screen captures from YouTube video clip entitled "iBGStar Review," in 1 page, uploaded on Mar. 27, 2012 by user "Valerie Anne C". Retrieved from Internet: <https://www.youtube.com/watch?v=0uGbNsh-pUc>. Corresponds to "Sanofi-aventis and AgaMatrix Unveil iBGStar Plug-In Glucose Meter for the iPhone, Medgadget" (APL_DEL00038203). Apple alleges that this reference has a prior art date of 2010.

Screen captures from YouTube video clip entitled "iBGStar bloedglucosemeter instructievideo," in 5 pages, uploaded on Mar. 9, 2011 by user "gezondheidbovenalles". Retrieved from Internet: <https://www.youtube.com/watch?v=ZlS-tTFfoUY>. Corresponds to "Sanofi-aventis and AgaMatrix Unveil iBGStar Plug-In Glucose Meter for the iPhone, Medgadget" (APL_DEL00038202). Apple alleges that this reference has a prior art date of 2010.

Screen captures from YouTube video clip entitled "Visi Mobile System for Vital Signs | Sotera Wireless," in 5 pages, uploaded on Aug. 29, 2012 by user "Eastman". Retrieved from Internet: <https://www.youtube.com/watch?v=ug9U43bsn6g>. Corresponds to "ViSi Mobile Patient Monitoring System Promotional Video" (APL_DEL00037306). Apple alleges that this reference has a prior art date of 2011.

Ashley et al., "Cardiology Explained", Remedica, 2004, pp. 257. [Uploaded in 2 parts].

Aldinger et al., "Advanced Ceramics and Future Materials: An Introduction to Structure, Properties, Technologies, Methods", Wiley-VCH GmbH & Co., 2010, pp. 17.

Shi, Feng, "Ceramic Materials—Progress in Modern Ceramics", InTech, Apr. 2012, pp. 6.

Francis, Johnson, "ECG monitoring leads and special leads", Indian Pacing and Electrophysiology Journal, vol. 16, 2016, pp. 92-95.

Shackelford et al., "Ceramic and Glass Materials: Structure, Properties and Processing", Springer, 2008, pp. 33.

Johns et al., "Adapting Qi-compliant wireless-power solutions to low-power wearable products", Texas Instruments, Analog Applications Journal, 2Q, 2014, pp. 7.

Loehman et al., "Characterization of Ceramics", Materials Characterization Series; Surfaces, Interfaces, Thin Films, Butterworth-Heinemann, 1993, pp. 13.

"Android 4.2 Compatibility Definition", Android Compatibility Program, chrome-extension://efaidnbmnnnibpcajpcglclefindmkaj/https://source.android.com/docs/compatibility/4.2/android-4.2-cdd.pdf, Jun. 10, 2013, pp. 36.

Chad, "Widget Tutorial Part 2—How to add lockscreen widgets on your device", https://digibites.zendesk.com/hc/en-US/articles/200351831-Widget-tutorial-part-2-How-to-add-lockscreen-widgets-on-your-device, Jan. 25, 2016, pp. 11.

Ion et al., "Hands-on: Multiple users, lock screen widgets round out Android 4.2", ARSTechnica, https://arstechnica.com/gadgets/2012/11/hands-on-multiple-users-lock-screen-widgets-round-out-android-4-2/, Nov. 14, 2012, pp. 12.

Kingery, W.D., "Introduction to Ceramics", John Wiley & Sons, Inc., 1960, pp. 23.

Ling et al., "The effects of link format and screen location on visual search of web pages," Ergonomics, vol. 47, No. 8, Jun. 22, 2004, pp. 18.

McCarthy et al., "Could I have the Menu Please? An Eye Tracking Study of Design Conventions", People and Computers XVII—Designing for Society, 2003, pp. 20.

Nielsen, Jakob, "Do Interface Standards Stifle Design Creativity?", Alertbox, https://web.archive.org/web/19991128143803/http://www.useit.com/alertbox/990822.html, Aug. 22, 1999, pp. 2.

Nielsen, Jakob, "Enhancing the Explanatory Power of Usability Heuristics", Human Factors in Computing Systems, CHI '94 Conference Proceedings, Aug. 1994, pp. 14.

Norman, Donald A., "The Design of Everyday Things", Double Day, 1988, pp. 37.

|Samsung Galaxy S4, 4G LTE Smartphone, User Manual, 2013, pp. 260. [Uploaded in 3 parts].

Samsung GT-19500, User Manual, 2013, pp. 147.

Santa-Maria et al., "The effect of violating visual conventions of a website on user performance and disorientation. How bad can it be?," SIGDOC'08, Sep. 22-24, 2008, pp. 8.

YouTube, "Adidas MiCoach Smart Run review | Engadget", https://www.youtube.com/watch?v=k5LpMY0okVo, Nov. 20, 2013, pp. 4.

YouTube, "Agent Smartwatch", https://www.youtube.com/watch?v=IsIEOILBuKM, Jun. 27, 2013, pp. 3.

YouTube, "Android 4.2 Lock Screen Widgets", https://www.youtube.com/watch?v=ZpN8Wyu_z6Y, Nov. 12, 2012, pp. 6.

YouTube, "Galaxy S8 review, how does the home button feel? [4K]", https://www.youtube.com/watch?v=_DlHga3ByoE, Apr. 5, 2017, pp. 5.

YouTube, "LG G Flex—How to reorganize page, app and widget". https://www.youtube.com/watch?v=J_12W-MrkVM, Dec. 6, 2013, pp. 3.

YouTube, "LG G2 Quick Tips—Adding Widgets to the Home Screen", https://www.youtube.com/watch?v=9xEwmiNoKok, Oct. 15, 2013, pp. 3.

YouTube, "Small, thin, and light LG Watch Style unboxing & review! (LG Watch Style Unboxing&Review)", https://www.youtube.com/watch?v=IJYtazmdMl0, Mar. 24, 2017, pp. 5.

YouTube, "Samsung Galaxy S4 Lock Screen Widget Tutorial", https://www.youtube.com/watch?v=oaWa905892s, Apr. 25, 2013, pp. 8.

(56) References Cited

OTHER PUBLICATIONS

Prior Use of Android Devices ("Android Prior Use"), Android versions: A living history from 1.0 to 14, available at https://www.computerworld.com/article/3235946/android-versions-a-living-history-from-1-0-to-today.html, pp. 18.
2012 LG Nexus 4 https://www.gsmarena.com/lg_nexus_4_e960-5048.php, pp. 4.
2013 Samsung Galaxy S4 https://www.gsmarena.com/samsung_i9500_galaxy_s4-5125.php, pp. 4.
2013 LG G2 https://www.gsmarena.com/lg_g2-5543.php, pp. 4.
2013 LG G Flex https://www.gsmarena.com/lg_g_flex-5806.php, pp. 4.
Apr. 2017 Samsung Galaxy S8, https://www.gsmarena.com/samsung_galaxy_s8-8161.php, pp. 3.
Android Device List Page https://www.androidheadlines.com/android-device-list-p. Sep. 13, 2023, pp. 8.
2014 LG G Watch W100 https://www.gsmarena.com/lg_g_watch_w100-7718.php, pp. 2.
2013 Adidas MiCoach Smart Run, https://www.cnet.com/reviews/adidas-micoach-smart-run-preview/, pp. 7.
Feb. 2017 LG Watch Style, https://www.gsmarena.com/lg_watch_style-8551.php, pp. 2.
Motorola, LG announce upcoming Android Wear smartwatches (Mar. 18, 2014), available at https://www.theverge.com/2014/3/18/5522340/motorola-lg-announce-upcoming-android-wear-smartwatches, pp. 3.
Oranger Watch 2.0 from Oranger (Cheng Yi Family) Technology Co. Ltd.; May 31, 2015, pp. 5.
Y. Mendelson, "Wearable Wireless Pulse Oximetry for Physiological Monitoring," PPL Workshop (2008), PPT Presentation, pp. 18.
Berbari, Edward J., Principles of Electrocardiogram medical Engineering Fundamentals, The Biomedical Engineering Handbook, 4th Ed., 2015, pp. 5.
Meziane et al., Dry Electrodes for Electrocardiogram, IOP Publishing, Physiological Measurement, 34 (2013) R47-R69.
Canfield, Douglas, "Drying and Curing Inks and Coatings on Glass", Mar. 26, 2013, pp. 5. https://www.glassmagazine.com/article/drying-and-curing-inks-and-coatings-glass.
Jung, Scott, "Medgadget Joins the Verily Baseline Project Study, Part 2: The Tech," archived on Oct. 27, 2017 by the Internet Organization's "Wayback Machine" at https://web.archive.org/web/20171027221742/https://www.medgadget.com/2017/10/medgadget-joins-verily-baseline-project-study-part-2-tech.html, pp. 7.
"Apple Watch Series 4: Beautifully redesigned with breakthrough communication, fitness and health capabilities," archived on Sep. 12, 2018 by the Internet Organization's Wayback Machine at https://web.archive.org/web/20180912191250/https://www.apple.com/newsroom/2018/09/redesigned-apple-watch-series-4-revolutionizescommunication-fitness-and-health/, pp. 15.
"Your heart rate. What it means, and where on Apple Watch you'll find it," archived on Jan. 23, 2019 by the Internet Organization's "Wayback Machine" at https://web.archive.org/web/20190123031906/https://support.apple.com/en-us/HT204666, pp. 4.
"Apple Watch Series 4—Health," archived on Sep. 20, 2018 by the Internet Organization's "Wayback Machine" at https://web.archive.org/web/20180920103403/https:/www.apple.com/apple-watch-series-4/health/, pp. 18.
"Charge Apple Watch," https://support.apple.com/guide/watch/chargeapple-watch-apd2b717523a/watchos (last visited Mar. 6, 2023), pp. 6.
"Apple Watch Magnetic Charging Cable (1 m)," https://www.apple.com/shop/product/MX2E2AM/A/apple-watchmagnetic-charging-cable-1m (last visited Mar. 6, 2023), pp. 4.
"Apple Watch Series 4 Teardown," https://www.ifixit.com/Teardown/Apple+Watch+Series+4+Teardown/113044 (last visited Mar. 6, 2023), pp. 14.
Letter from Jennifer Shih to Verily Life Sciences LLC re 510(k) No. K192415, U.S. Food & Drug Administration, dated Jan. 17, 2020 in 7 pages. https://www.accessdata.fda.gov/cdrh_docs/pdf19/K192415.pdf.

"AGENT: The World's Smartest Watch", https://www.kickstarter.com/projects/secretlabs/agent-the-worlds-smartest-watch/faqs, Last updated Apr. 30, 2016, pp. 8.
"Introducing Verily Study Watch", Verily, https://verily.com/blog/Introducing-Verily-Study-Watch/, Apr. 14, 2017, pp. 6.
CMS50K Wearable SpO2/ECG Monitor from Contec Medical Systems Co., Ltd. ("CMS50K Watch"), Per Apple: Date of Public Knowledge, Use, and/or Sale is No later than Apr. 2016, 1 page.
"Care for your pillow partner with all your heart, Oranger Snoring Monitor 2.0", https://mp.weixin.qq.com/s/EkQ_fNfotpCMaoDt3xan9Q, Jul. 27, 2015, pp. 10 (21 total pages with Translation).
"An entry-level all-round watch that makes sports unique I Aiwei P1 energy sports watch", https://mp.weixin.qq.com/s/d6ACPZqrRpvqdLHmb7UOsQ, Jun. 10, 2018, pp. 36.
"Monitor heart rate and record sports, experience of Avery energy sports watch P1", https://www.sohu.com/a/234524743_115300, Jun. 8, 2018, pp. 9 (26 total pages with Translation).
"Comprehensive functions and excellent cost-effectiveness, Aiwei energy sports watch P1 trial experience", https://mp.weixin.qq.com/s/XvRdKBCYQWqZwBP-Cesz7g, Jun. 27, 2018, pp. 11 (20 total pages with Translation).
Hanselman, Scott, "Exclusive Sneak Peek: The AGENT Smart Watch Emulator and managed .NET code on my wrist!", https://www.hanselman.com/blog/exclusive-sneak-peek-the-agent-smart-watch-emulator-and-managed-net-code-on-my-wrist, Jun. 18, 2013, pp. 2.
Luke, Jack, "Garmin VivoActive 3 brings new design, interface and features", https://www.bikeradar.com/news/garmin-vivoactive-3-brings-new-design-interface-and-features, Sep. 1, 2017, pp. 6.
Bennett, Brian, "LG's WCP-300 easily charges sans wires (hands-on)", https://www.cnet.com/reviews/lg-wcp-300-wireless-charger-preview/, Feb. 26, 2013, pp. 3.
Chang-Wook, Kim, "Mobile 11th Street, Mobile Phone Wireless Charger Unlimited Sale", etnews, Mar. 11, 2013, pp. 2.
DC Rainmaker, "Garmin Vivoactive 3 In-Depth Review", https://www.dcrainmaker.com/2017/10/garmin-vivoactive-3-in-depth-review.html, Oct. 18, 2017, pp. 119.
DC Rainmaker, "Garmin's Vivomove HR: Everything you need to know", https://www.dcrainmaker.com/2017/09/garmins-vivomove-hr-everything.html, Sep. 6, 2017, pp. 27.
YouTube, "Magconn, Wireless Charger", https://www.youtube.com/watch?v=qxEXCOChLNA, Aug. 22, 2012, 1 page.
YouTube, "VivoActive 3 Review—Final Verdict after 30 days of use (EP4)", https://www.youtube.com/watch?v=IDcakqddUCU, Oct. 15, 2017, pp. 5.
Stein, Scott, "Garmin Vivomove HR review: The best fitness tracker in disguise", https://www.cnet.com/reviews/garmin-vivomove-hr-review/, Nov. 22, 2017, pp. 5.
Sumra, Husain, "Garmin Vivomove HR: Essential guide to the stylish hybrid fitness watch", https://www.wareable.com/garmin/garmin-vivomove-hr-release-date-price-specs-4983, Sep. 5, 2017, pp. 5.
Mendelson, Yitzhak, "Invasive and Noninvasive Blood Gas Monitoring", Bioinstrumentation and Biosensors, 1991, pp. 249-279.
Leslie Cromwell et al., Biomedical Instrumentation and Measurements (1973), pp. 31-32.
Adecro Plastics, ABS Plastic Properties, (last visited Mar. 13, 2023), www.adrecoplastics.co.uk/abs-plasticproperties/#:~:text=Finally%2C%20ABS%20has%20low%20heat, absorb%20shock%20effectively%20and%20reliably, pp. 7.
Carl R. Nave, Conductors and Insulators, Hyperphysics (last visited Mar. 13, 2023), http://hyperphysics.phyastr.gsu.edu/hbase/electric/conins.html#c1, pp. 3.
Merriam-Webster's Collegiate Dictionary, 11th ed. 2004, Definition of "embedded" and "Pad", pp. 406 & 890 (5 pgs. Total).
Random House Unabridged Dictionary (2nd ed. 1993), Definition of "embedded" pp. 635.
The American Heritage Dictionary of the English Language (4th ed. 2000) Definition of "embedded" pp. 583.
Steven M. Kaplan, Wiley Electrical and Electronics Engineering Dictionary (2004) Definition of "lead", pp. 414-415 [Total pages 4].
Stedman's Medical Dictionary (28th ed. 2006) Definition of "lead" pp. 1062.

(56)                    References Cited

OTHER PUBLICATIONS gov.uk Designs Journal Entry for Lee-616, https://www.registereddesign.
service.gov.uk/view/2013/11/215 (last visited Mar. 28, 2023), pp.
12.
YouTube, "GMYLE(R) Qi Wireless Charger Review (Nexus 5)",
https://www.youtube.com/watch?v=EvJ4Jkvj_R8, Nov. 28, 2013,
pp. 10.
"Apple Watch Teardown—iFixit," https://www.ifixit.com/Teardown/
Apple+Watch+Teardown/40655 (last visited Apr. 3, 2023), pp. 18.
"Apple Unveils Apple Watch—Apple's Most Personal Device Ever,"
https://www.apple.com/newsroom/2014/09/09Apple-Unveils-Apple-
Watch-Apples-Most-Personal-Device-Ever/ (last visited Mar. 31,
2023), pp. 4.
"Apple Watch—Technology," archived on Sep. 11, 2014 by the
Internet Organization's "Wayback Machine" at https://web.archive.
org/web/20140911003437/http://www.apple.com/watch/technol-
ogy/, pp. 8.
Patancheru, Govardhan Reddy, "Wearable Heart Rate Measuring
Unit", Master's Thesis in Electronics Design, 30HP, Mid Sweden
University, Nov. 5, 2014, pp. 75.
"Pulse Sensor, Easy to Use Heart Rate Sensor & Kit", PulseSensor.
com, World Famous Electronics LLC. NY, USA, pp. 2.
Oct. 20, 2022 Complaint for Patent Infringement and Demand for
Jury Trial, *Apple Inc.* v. *Masimo Corporation and Sound United,
LLC,* Case No. 1:22-cv-01377-UNA, 32 pages.
Oct. 20, 2022 Complaint for Patent Infringement and Demand for
Jury Trial, *Apple Inc.* v. *Masimo Corporation and Sound United,
LLC,* Case No. 1:22-cv-01378-UNA, 77 pages.
Dec. 12, 2022 Defendant Masimo Corporation's Answer to Com-
plaint and Counterclaims, *Apple Inc.* v. *Masimo Corporation and
Sound United, LLC,* Case No. 1:22-cv-01378-MN, 162 pages.
Jun. 8, 2023 Counter-Defendant Apple Inc.'s Initial Invalidity
Contentions, *Apple Inc.* v. *Masimo Corporation and Sound United,
LLC, Masimo Corporation* v. *Apple Inc.,* Case No. 1:22-cv-01378-
MN, 47 pages.
Exhibits A-1 to A-4 and Exhibits A-6 to A-17 submitted with
2023-06-08 Counter-Defendant Apple Inc.'s Initial Invalidity Con-
tentions, *Apple Inc.* v. *Masimo Corporation and Sound United, LLC,
Masimo Corporation* v. *Apple Inc.,* Case No. 1:22-cv-01378-MN,
3005 pages. [Uploaded in 9 parts].
Exhibits B-1 to B-4 and Exhibits B-6 to B-17 submitted with Jun.
8, 2023 Counter-Defendant Apple Inc.'s Initial Invalidity Conten-
tions, *Apple Inc.* v. *Masimo Corporation and Sound United, LLC,
Masimo Corporation* v. *Apple Inc.,* Case No. 1:22-cv-01378-MN,
3194 pages. [Uploaded in 10 parts].
Jun. 23, 2023 Defendant Masimo Corporation's Answer to Com-
plaint and First Amended Counterclaims, *Apple Inc.* v. *Masimo
Corporation and Sound United, LLC, Masimo Corporation* v. *Apple
Inc.,* Case No. 1:22-cv-01378-MN, 170 pages.
Jul. 13, 2023 Joint Claim Construction Chart for Asserted Masimo
Patents, *Apple Inc.* v. *Masimo Corporation and Sound United, LLC,
Masimo Corporation* v. *Apple Inc.,* Case No. 1:22-cv-01378-MN,
169 pages.
Jul. 13, 2023 Exhibits B & C of Joint Claim Construction Chart for
Asserted Masimo Patents, *Apple Inc.* v. *Masimo Corporation and
Sound United, LLC, Masimo Corporation* v. *Apple Inc.,* Case No.
1:22-cv-01378- MN, 1131 pages.
Humphreys, An Investigation of Remote Non-Contact
Photoplethysmography and Pulse Oximetry, National University of
Ireland: Department of Electronic Engineering, Aug. 2007, pp. 205.
Anliker et al., "AMON: a wearable multiparameter medical moni-
toring and alert system," in IEEE Transactions on Information
Technology in Biomedicine, vol. 8, No. 4, Dec. 2004.
Asada, et al. "Mobile Monitoring with Wearable Photoplethysmographic
Biosensors", IEEE Engineering in Medicine and Biology Magazine,
2003.
Bagha, et al. "A Real Time Analysis of PPG Signal for Measurement
of SpO2 and Pulse Rate", International Journal of Computer Appli-
cations (0975-8887), vol. 36—No. 11, 2011.

Branche et al., "Measurement Reproducibility and Sensor Place-
ment Considerations in Designing a Wearable Pulse Oximeter for
Military Applications," Proceedings of the IEEE 30th Annual North-
east Bioengineering Conference, 2004, pp. 216-217.
Branche et al., "Signal Quality and Power Consumption of a New
Prototype Reflectance Pulse Oximeter Sensor," Proceedings of the
IEEE 31st Annual Northeast Bioengineering Conference, 2005, pp.
1-2.
Celka, et al. "Motion resistant earphone located infrared based heart
rate measurement device", Research Gate, 2004.
Comtois, et al. "A Comparative Evaluation of Adaptive Noise
Cancellation Algorithms for Minimizing Motion Artifacts in a
Forehead-Mounted Wearable Pulse Oximeter", IEEE, 2007.
Comtois, et al. "A Noise Reference Input to an Adaptive Filter
Algorithm for Signal Processing in a Wearable Pulse Oximeter",
IEEE, 2007.
Conway, et al. "Wearable computer as a multi-parametric monitor
for physiological signals," Proceedings IEEE International Sympo-
sium on Bio-Informatics and Biomedical Engineering, pp. 236-242,
2000.
Crilly, et al. "An Integrated Pulse Oximeter System for Telemedicine
Applications", IEEE Instrumentation and Measurement Technology
Conference, 1997.
Dassel, et al. "Reflective Pulse Oximetry at the Forehead Improves
by Pressure on the Probe", J. Clin. Monit, 11:237-244, 1995.
DC Rainmaker, Mio Alpha Optical Heart Rate Monitor In-Depth
Review, https://www.dcrainmaker.com/2013/02/monitorbluetooth-
smartant.html (Feb. 12, 2013).
Dresher et al., "A New Reflectance Pulse Oximeter Housing to
Reduce Contact Pressure Effects," Proceedings of the IEEE 32nd
Annual Northeast Bioengineering Conference, 2006, pp. 49-50.
Dresher, et al. "Reflectance Forehead Pulse Oximetry: Effects of
Contact Pressure During Walking", IEEE, 2006.
Faulkner, "Apple Watch Heart Rate Sensor: Everything You Need
to Know." TechRadar India, TechRadar, 2015.
"Galaxy S5 Explained: The Heart Rate Sensor and S Health 3.0."
Samsung Global Newsroom, 2014.
Gibbs, et al. "Active motion artifact cancellation for wearable health
monitoring sensors using collocated MEMS accelerometers", SPIE,
vol. 5765, 2005.
Hayes, "How the Sensors inside Fitness Tracker Work." Digital
Trends, 2014.
"Heart Rate Measurement Technology" EPSON, 2019.
Heerlein, et al. "LED-Based Sensor for Wearable Fitness Tracking
Products", EDN, 2014.
International Preliminary Report on Patentability and Written Opin-
ion in PCT Patent Application No. PCT/US2016/040190, as mailed
Jan. 2, 2018.
"Introducing Easy Pulse: A DIY Photoplethysmographic Sensor for
Measuring Heart Rate", Embedded Lab, 2012.
W. S. Johnston et al., "Extracting Breathing Rate Information from
a Wearable Reflectance Pulse Oximeter|Sensor," Proceedings of the
26th Annual International Conference of the IEEE EMBS, Sep.
2004, pp. 5388-5391.
W. Johnston et al., "Extracting Heart Rate Variability from a
Wearable Reflectance Pulse Oximeter," Proceedings of the IEEE
31st Annual Northeast Bioengineering Conference, 2005, pp. 1-2.
Keikhosravi, et al. "Effect of deep breath on the correlation between
the wrist and finger photoplethysmograms", pp. 135-138, 2012.
Kilbane, et al. "Design Considerations for Wrist-Wearable Heart
Rate Monitors," Arrow Intelligent Systems, 2015.
Konig, V. et al., "Reflectance Pulse Oximetry—Principles and
Obstetric Application in the Zurich System," J Clin Monit 1998; 14:
403-412.
Konstantas, et al. "Mobile Patient Monitoring: The MobiHealth
System", Research Gate, 2004.
Kuboyama, "Motion Artifact Cancellation for Wearable
Photoplethysmographic Sensor", Massachusetts Institute of Tech-
nology, pp. 1-66, 2010.
Kviesis-Kipge, et al., "Miniature Wireless Photoplethysmography
Devices: Integration in Garments and Test Measurements", SPIE
vol. 8427 84273H-6, 2012.

(56)           References Cited

OTHER PUBLICATIONS

Lee, et al. "Development of a Wristwatch-Type PPG Array Sensor Module", IEEE, 2011.

Lin, et al. "RTWPMS: A Real-Time Wireless Physiological Monitoring System", IEEE Transactions on Information Technology in Biomedicine, vol. 10, No. 4, 2006.

Lingaiah, et al. "Measurement of Pulse rate and SPo2 using Pulse Oximeter developed using LabVIEW", IOSR Journal of Electrical and Electronics Engineering (IOSR-JEEE), e-ISSN: 2278-1676, p. ISSN: 2320-3331, vol. 8, Issue 1, pp. 22-26, 2013.

Lukowicz, et al. "AMON: a wearable medical computer for high risk patients," Proceedings. Sixth International Symposium on Wearable Computers, 2002.

Lukowicz, et al. "The Weararm Modular, Low-Power Computing Core", IEEE Micro, 2001.

Mapar "Wearable Sensor for Continuously Cigilant Blood Perfusion and Oxygenation", UCLA, 2012.

Y. Mendelson et al., "Noninvasive Pulse Oximetry Utilizing Skin Reflectance Photoplethysmography," IEEE Transactions on Biomedical Engineering, vol. 35, No. 10, Oct. 1988, pp. 798-805.

Mendelson et al., "A Mobile PDA-Based Wireless Pulse Oximeter," Proceedings of the IASTED International Conference Telehealth, Jul. 19-21, 2005, pp. 1-6.

Mendelson et al., "A Wearable Reflectance Pulse Oximeter for Remote Physiological Monitoring,"Proceedings of the 28th IEEE EMBS Annual International Conference, Aug. 30-Sep. 3, 2006, pp. 912-915.

Mendelson et al., "Accelerometery-Based Adaptive Noise Cancellation for Remote Physiological Monitoring by a Wearable Pulse Oximeter," Proceedings of the 3rd IASTED International Conference Telehealth, May 31-Jun. 1, 2007, pp. 28-33.

Mendelson et al., "Measurement Site and Photodetector Size Considerations in Optimizing Power Consumption of a Wearable Reflectance Pulse Oximeter," Proceedings of the 25th Annual International Conference of the IEEE EMBS, Sep. 17-21, 2003, pp. 3016-3019.

Mendelson et al., "Minimization of LED Power Consumption in the Design of a Wearable Pulse Oximeter, "Proceedings of the IASTED International Conference Biomedical Engineering, Jun. 25-27, 2003, 6 pages.

Mendelson et al., Skin Reflectance Pulse Oximetry: In Vivo Measurements from the Forearm and Calf, Journal of Clinical Monitoring vol. 7 No. 1, pp. 7-12, dated Jan. 1991.

Mio ALPHA Complete User Guide, https://www.medisana.com/out/pictures/media/manual/mio_alpha_user_guide_en.pdf (2014).

Oliver et al., "HealthGear: A Real-time Wearable System for Monitoring and Analyzing Physiological Signals," Proceedings of the International Workshop on Wearable and Implantable Body Sensor Networks, IEEE Computer Society, 2006, pp. 1-4.

Pandian et al., "Smart Vest: Wearable Multi-Parameter Remote Physiological Monitoring System," Medical Engineering & Physics 30, 2008. pp. 466-477.

"PerformTek Precision Biometrics", ValenCell, 2013.

Phattraprayoon, et al. "Accuracy of Pulse Oximeter Readings from Probe Placement on Newborn Wrist And Ankle", Journal of Perinatology, vol. 32, pp. 276-280, 2012.

Poh et al. "Motion-Tolerant Magnetic Earring Sensor and Wireless Earpiece for Wearable Photoplethysmography", IEEE Transactions on Information Technology in Biomedicine, vol. 14, No. 3, 2010.

Pujary, "Investigation of Photodetector Optimization In Reducing Power Consumption By a Noninvasive Pulse Oximeter Sensor", Worcester Polytechnic Institute, pp. 1-133, 2004.

Purjary et al., "Photodetector Size Considerations in the Design of a Noninvasive Reflectance Pulse Oximeter for Telemedicine Applications", IEEE, 2003.

QuickSpecs; HP iPAQ Pocket PC h4150 Series, dated Nov. 20, 2003, in 8 pages.

Renevey et al., "Wrist-Located Pulse Detection Using IR Signals, Activity and Nonlinear Artifact Cancellation," Proceedings of the 23rd Annual EMBS International Conference, Oct. 25-28, 2001, pp. 3030-3033.

Rhee et al. "Artifact-Resistant Power-Efficient Design of Finger-Ring Plethysmographic Sensors," IEEE Transactions on Biomedical Engineering, vol. 48, No. 7, Jul. 2001, pp. 795-805.

Rhee et al. "Artifact-Resistant, Power Efficient Design of Finger-Ring Plethysmographic Sensors, Part I: Design and Analysis," 22nd Annual International Conference IEEE Engineering in Medicine and Biology Society, Jul. 23-28, 2000, pp. 2792-2795.

Rhee et al., "Design of a Artifact-Free Wearable Plethysmographic Sensor," 21st Annual International Conference IEEE Engineering in Medicine and Biology Society, Oct. 13-16, 1999, p. 786.

Rhee et al., "The Ring Sensor: a New Ambulatory Wearable Sensor for Twenty-Four Hour Patient Monitoring," Proceedings of the 20th Annual International Conference of the IEEE Engineering in Medicine and Biology Society, Oct. 29-Nov. 1, 1998, 4 pages.

Savage et al., "Optimizing Power Consumption in the Design of a Wearable Wireless Telesensor:Comparison of Pulse Oximeter Modes," Proceedings of IEEE 29th Annual Nonheust Bioengineering Conference, 2003, pp. 150-151.

Scully, et al. "Physiological Parameter Monitoring from Optical Recordings with a Mobile Phone", IEEE Trans Biomed Eng. ; 59(2): 303-306, 2012.

Shaltis et al., "Novel Design for a Wearable, Rapidly Depolyable, Wireless Noninvasive Triage Sensor," Proceedings of the 2005 IEEE, Engineering in Medicine and Biology 27th Annual Conference, Sep. 1-4, 2005, pp. 3567-3570.

Shin et al., "A Novel Headset with a Transmissive PPG Sensor for Heart Rate Measurement", ICBME 2008, Proceedings 23, pp. 519-522, 2009.

Shyamkumar, et al. "Wearable Wireless Cardiovascular Monitoring Using Textile-Based Nanosensor and Nanomaterial Systems", Electronics 3, pp. 504-520, 2014.

Stojanovic, et al. "Design of an Oximeter Based on LED-LED Configuration and FPGA Technology", Sensors, 13, 574-586, 2013.

Stuban, et al. "Optimal filter bandwidth for pulse oximetry", Rev. Sci. Instrum. 83, 104708, 2012.

Tamannagari, "Power Efficient Design of Finder-Ring Sensor for Patient Monitoring," Master of Science in Electrical Engineering, The University of Texas at San Antonio, College of Engineering, Department of Electrical Engineering, Dec. 2008, 74 pages.

Tamura et al. "Wearable Photoplethysmographic Sensors—Past and Present", Electronics, 3, 282-302, 2014.

Tofs, et al. "Body-Heat Powered Autonomous Pulse Oximeter", IEEE Sensors, 2006.

Townsend, et al. "Pulse Oximetry", Medical Electronics, 2001.

Tura, et al., "A Medical Wearable Device with Wireless Bluetooth-based Data Transmission", Measurement Science Review, vol. 3, Section 2, 2003.

Vogel, et al. "In-Ear Vital Signs Monitoring Using a Novel Microoptic Reflective Sensor", IEEE Transactions on Information Technology in Biomedicine, vol. 13, No. 6, 2009.

Warren, et al. "Designing Smart Health Care Technology into the Home of the Future", United States: N. p., 1999.

"Withings Pulse: Activity Tracker—Sleep Analyzer Hear Rate Analyzer; Installation and Operating Instructions", Withings, 2015.

Yamashita et al., "Development of a Ring-Type Vital Sign Telemeter," Biotelemetry XIII, Mar. 26-31, 1995, pp. 145-150.

Yan, et al. "An Efficient Motion-Resistant Method for Wearable Pulse Oximeter", IEEE Transactions on Information Technology in Biomedicine, vol. 12, No. 3, 2008.

Yang, et al. "A Twenty-Four Hour Tele-Nursing System Using a Ring Sensor", Proc. of 1998 Int. Conf. on Robotics and Automation, 1998.

Yang, et al. "Development Of The Ring Sensor For Healthcare Automation", Robotics and Autonomous Systems, 30, pp. 273-281, 2000.

Yang, et al. "SpO2 and Heart Rate Measurement with Wearable Watch Based on PPG", IEEE, 2015.

Zhai, et al. "A Wireless Sensor Network for Hospital Patient Monitoring", University of Calgary, 2007.

(56)         References Cited

OTHER PUBLICATIONS

Geun, et al. "Measurement site and applied pressure consideration in wrist photoplethysmography," The 23rd International Technical Conference on Circuits/Systems, Computers and Communications (ITC-CSCC 2008).

Lee, et al. "Reflectance pulse oximetry: Practical issues and limitations," ICT Express 2 (2016) 195-198.

Netter, Frank H., "Atlas of Human Anatomy", Third Edition, 2003.

Perry, T., "Should You Trust Apple's New Blood Oxygen Sensor," IEEE Spectrum, Sep. 2020.

Thompson, et al., "A small, high-fidelity reflectance pulse oximeter", ASEE Annual Conference and Exposition, Conference Proceedings, 2007.

Jan. 9, 2020 Complaint for (1) Patent Infringement (2) Trade Secret Misappropriation and (3) Ownership of Patents and Demand for Jury Trial, *Masimo Corporation and Cercacor Laboratories, Inc.* v. *Apple Inc.*, Case No. 8:20-cv-00048, 64 pages.

Mar. 25, 2020 First Amended Complaint for (1) Patent Infringement (2) Trade Secret Misappropriation (3) Correction of Inventorship and (4) Ownership of Patents and Demand for Jury Trial, and including Exhibits 13-24 (Exhibits 1-12 and 25-31 comprise copies of publicly available U.S. patents and U.S. patent application publications, and are not included herein for ease of transmission), *Masimo Corporation and Cercacor Laboratories, Inc.* v. *Apple Inc.*, Case No. 8:20-cv-00048, pp. 1-94, 983-1043 (total of 156 pages).

Y. Mendelson, et al., "Design and Evaluation of a New Reflectance Pulse Oximeter Sensor", Worcester Polytechnic Institute, Biomedical Engineering Program, Worcester, MA 01609, Association for the Advancement of Medical Instrumentation, vol. 22, No. 4, 1988, pp. 167-173, Abstract, 1 page.

Excerpts of Design of Pulse Oximeters, J.G. Webster, Institution of Physics Publishing, IOP Publishing Ltd, 1997, 150 pages. [uploaded in 3 parts].

Lam et al., "A Smartphone-Centric Platform for Personal Health Monitoring using Wireless Wearable Biosensors", IEEE, ICICS 2009, 7 pages.

Vashist et al., "Commercial Smartphone-Based Devices and Smart Applications for Personalized Healthcare Monitoring and Management", Diagnostics, 2014, vol. 4, pp. 104-128.

Mendelson, "Invasive and Noninvasive Blood Gas Monitoring," Bioinstrumentation and biosensors, 1991, pp. 249-279.

Severinghaus, "Pulse Oximetry," Computing and Monitoring in Anesthesia and Intensive Care, 1992, pp. 391-403.

Takatani et al., "Optical Oximetry Sensors for Whole Blood and Tissue," IEEE Engineering in Medicine and Biology, 1994, pp. 347-357.

Jun. 29, 2021 Complaint under Section 337 of the Tariff Act of 1930, as Amended, and including Exhibits 11-40 (Exhibits 1-10 comprise copies of publicly available U.S. patents, and are not included herein for ease of transmission), *Masimo Corporation and Cercacor Laboratories, Inc.* v. *Apple Inc.*, United States International Trade Commission, Investigation No. 337-TA-1276, 736 pages. [uploaded in 13 parts].

Jul. 7, 2021 First Amended Complaint under Section 337 of the Tariff Act of 1930, as Amended, *Masimo Corporation and Cercacor Laboratories, Inc.* v. *Apple Inc.*, United States International Trade Commission, Investigation No. 337-TA-1276, 44 pages.

Sep. 23, 2021 Response of Apple Inc. to First Amended Complaint and Notice of Investigation, and including Exhibit A and Appendix A, *Masimo Corporation and Cercacor Laboratories, Inc.* v. *Apple Inc.*, United States International Trade Commission, Investigation No. 337-TA-1276, 664 pages.

Dec. 3, 2021 Respondent Apple Inc.'s Preliminary Invalidity Contentions for U.S. Pat. No. 10,912,501, U.S. Pat. No. 10,912,502, U.S. Pat. No. 10,945,648, U.S. Pat. No. 10,687,745, and U.S. Pat. No. 7,761,127, and including Exhibits A1-A6, B1-B6, and C1-C6 related to U.S. Pat. No. 10,912,501, U.S. Pat. No. 10,912,502, U.S. Pat. No. 10,945,648 (Exhibits D1-D16 and E1-E13 relate to U.S. Pat. No. 10,687,745, and U.S. Pat. No. 7,761,127, and are not included herein but are available upon request), *Masimo Corpora-*

*tion and Cercacor Laboratories, Inc.* v. *Apple Inc.*, United States International Trade Commission, Investigation No. 337-TA-1276, 443 pages.

Dec. 3, 2021 Respondent Apple Inc.'s Preliminary Invalidity Contentions for U.S. Pat. No. 10,912,501, U.S. Pat. No. 10,912,502, U.S. Pat. No. 10,945,648, U.S. Pat. No. 10,687,745, and U.S. Pat. No. 7,761,127, and including Exhibits D1-D16 related to U.S. Pat. No. 10,687,745 (Exhibits A1-A6, B1-B6, C1-C6, and E1-E13 relate to U.S. Pat. No. 10,912,501, U.S. Pat. No. 10,912,502, U.S. Pat. No. 10,945,648, and U.S. Pat. No. 7,761,127, and are not included herein but are available upon request), *Masimo Corporation and Cercacor Laboratories, Inc.* v. *Apple Inc.*, United States International Trade Commission, Investigation No. 337-TA-1276, 443 pages.

Dec. 3, 2021 Respondent Apple Inc.'s Preliminary Invalidity Contentions for U.S. Pat. No. 10,912,501, U.S. Pat. No. 10,912,502, U.S. Pat. No. 10,945,648, U.S. Pat. No. 10,687,745, and U.S. Pat. No. 7,761,127, Exhibits A-1 to A-6, *Masimo Corporation and Cercacor Laboratories, Inc.* v. *Apple Inc.*, United States International Trade Commission, Investigation No. 337-TA-1276, 1230 pages. [uploaded in 2 parts].

Dec. 3, 2021 Respondent Apple Inc.'s Preliminary Invalidity Contentions for U.S. Pat. No. 10,912,501, U.S. Pat. No. 10,912,502, U.S. Pat. No. 10,945,648, U.S. Pat. No. 10,687,745, and U.S. Pat. No. 7,761,127, Exhibits B-1 to B-6, *Masimo Corporation and Cercacor Laboratories, Inc.* v. *Apple Inc.*, United States International Trade Commission, Investigation No. 337-TA-1276, 1343 pages. [uploaded in 2 parts].

Dec. 3, 2021 Respondent Apple Inc.'s Preliminary Invalidity Contentions for U.S. Pat. No. 10,912,501, U.S. Pat. No. 10,912,502, U.S. Pat. No. 10,945,648, U.S. Pat. No. 10,687,745, and U.S. Pat. No. 7,761,127, Exhibits C-1 to C-6, *Masimo Corporation and Cercacor Laboratories, Inc.* v. *Apple Inc.*, United States International Trade Commission, Investigation No. 337-TA-1276, 1222 pages. [uploaded in 2 parts].

Dec. 3, 2021 Respondent Apple Inc.'s Preliminary Invalidity Contentions for U.S. Patent Nos. 10,912,501, 10,912,502, 10,945,648, 10,687,745, and 7,761,127, Exhibits D-1 to D-16, *Masimo Corporation and Cercacor Laboratories, Inc.* v. *Apple Inc.*, United States International Trade Commission, Investigation No. 337-TA-1276, 2123 pages. [uploaded in 2 parts].

Dec. 3, 2021 Respondent Apple Inc.'s Preliminary Invalidity Contentions for U.S. Pat. No. U.S. Pat. No. 10,912,501, U.S. Pat. No. 10,912,502, U.S. Pat. No. 10,945,648, U.S. Pat. No. 10,687,745, and U.S. Pat. No. 7,761,127, Exhibits E-1 to E-16, *Masimo Corporation and Cercacor Laboratories, Inc.* v. *Apple Inc.*, United States International Trade Commission, Investigation No. 337-TA-1276, 1004 pages.

Jan. 13, 2022 Joint Proposed Claim Construction Chart, *Masimo Corporation and Cercacor Laboratories, Inc.* v. *Apple Inc.*, United States International Trade Commission, Investigation No. 337-TA-1276, 8 pages.

Jan. 27, 2022 Respondent Apple Inc.'s Opening Markman Brief, and including Exhibits 1-7, *Masimo Corporation and Cercacor Laboratories, Inc.* v. *Apple Inc.*, United States International Trade Commission, Investigation No. 337-TA-1276,144 pages.

Jan. 27, 2022 Complainant's Opening Claim Construction Brief, and including Exhibits 1-16, *Masimo Corporation and Cercacor Laboratories, Inc.* v. *Apple Inc.*, United States International Trade Commission, Investigation No. 337-TA-1276, 1019 pages. [uploaded in 9 parts].

Feb. 9, 2022 Respondent Apple Inc.'s Motion for Leave to File Amended Response to the First Amended Complaint, *Masimo Corporation and Cercacor Laboratories, Inc.* v. *Apple Inc.*, United States International Trade Commission, Investigation No. 337-TA-1276, 4 pages.

Feb. 9, 2022 Memorandum in support of Respondent Apple Inc.'s Motion for Leave to File Amended Response to the First Amended Complaint, and including Exhibits 1 (with Exhibits A-J) and 2, *Masimo Corporation and Cercacor Laboratories, Inc.* v. *Apple Inc.*, United States International Trade Commission, Investigation No. 337-TA-1276, 1477 pages. [uploaded in 2 parts].

(56)            References Cited

OTHER PUBLICATIONS

Feb. 10, 2022 Complainants' Rebuttal Claim Construction Brief, and including Exhibits 17-21, *Masimo Corporation and Cercacor Laboratories, Inc. v. Apple Inc.,* United States International Trade Commission, Investigation No. 337-TA-1276, 59 pages.
Feb. 10, 2022 Respondent Apple Inc.'s Rebuttal Markman Brief, and including Exhibit 8, *Masimo Corporation and Cercacor Laboratories, Inc. v. Apple Inc.,* United States International Trade Commission, Investigation No. 337-TA-1276, 21 pages.
Feb. 15, 2022 Respondent Apple Inc.'s Notice of Prior Art, *Masimo Corporation and Cercacor Laboratories, Inc. v. Apple Inc.,* United States International Trade Commission, Investigation No. 337-TA-1276, 15 pages.
Feb. 17, 2022 Hearing Transcript, *Masimo Corporation and Cercacor Laboratories, Inc. v. Apple Inc.,* United States International Trade Commission, Investigation No. 337-TA-1276, 106 pages.
Feb. 18, 2022 Complainants' Opposition to Respondent's Motion for Leave to File Amended Response to the First Amended Complaint, and including Exhibits A-J, *Masimo Corporation and Cercacor Laboratories, Inc. v. Apple Inc.,* United States International Trade Commission, Investigation No. 337-TA-1276, 691 pages. [uploaded in 5 parts].
Feb. 18, 2022 Respondent Apple Inc.'s Rebuttal Claim Construction Evidence, and including Exhibit 9, *Masimo Corporation and Cercacor Laboratories, Inc. v. Apple Inc.,* United States International Trade Commission, Investigation No. 337-TA-1276, 12 pages.
Feb. 23, 2022 Respondent Apple Inc.'s Reply in support of its Motion for Leave to File Amended Response to First Amended Complaint (Motion No. 1276-018), and including Exhibit 3, *Masimo Corporation and Cercacor Laboratories, Inc. v. Apple Inc.,* United States International Trade Commission, Investigation No. 337-TA-1276, 65 pages.
Feb. 23, 2022 Updated Joint Proposed Claim Construction Chart, *Masimo Corporation and Cercacor Laboratories, Inc. v. Apple Inc.,* United States International Trade Commission, Investigation No. 337-TA-1276, 6 pages.
Apr. 11, 2022 Order No. 24 Granting-in-Part and Denying-in-Part Respondent's Motion for Leave to File Amended Response to the Complaint to Add Affirmative Defenses, *Masimo Corporation and Cercacor Laboratories, Inc. v. Apple Inc.,* United States International Trade Commission, Investigation No. 337-TA-1276, 10 pages.
May 13, 2022 Complainants' Pre-Hearing Brief, *Masimo Corporation and Cercacor Laboratories, Inc. v. Apple Inc.,* United States International Trade Commission, Investigation No. 337-TA-1276, 274 pages.
May 16, 2022 Respondent Apple Inc.'s Corrected Pre-Hearing Brief, *Masimo Corporation and Cercacor Laboratories, Inc. v. Apple Inc.,* United States International Trade Commission, Investigation No. 337-TA-1276, 264 pages.
Jun. 27, 2022 Complainants' Initial Post-Hearing Brief and including Complainants' Final Exhibit Lists, *Masimo Corporation and Cercacor Laboratories, Inc. v. Apple Inc.,* United States International Trade Commission, Investigation No. 337-TA-1276, 434 pages. [uploaded in 3 parts].
Jun. 27, 2022 Respondent Apple Inc.'s Post-Hearing Brief and including Respondent's Final Exhibit Lists and Respondent's Corrected Final Exhibit Lists, *Masimo Corporation and Cercacor Laboratories, Inc. v. Apple Inc.,* United States International Trade Commission, Investigation No. 337-TA-1276, 338 pages.
Jul. 11, 2022 Respondent Apple Inc.'s Reply Post-Hearing Brief, *Masimo Corporation and Cercacor Laboratories, Inc. v. Apple Inc.,* United States International Trade Commission, Investigation No. 337-TA-1276, 191 pages.
Jul. 11, 2022 Complainants' Reply Post-Hearing Brief, *Masimo Corporation and Cercacor Laboratories, Inc. v. Apple Inc.,* United States International Trade Commission, Investigation No. 337-TA-1276, 217 pages. [uploaded in 2 parts].
Aug. 19, 2022 Complainant's Corrected Initial Post-Hearing Brief, *Masimo Corporation and Cercacor Laboratories, Inc. v. Apple Inc.,*

United States International Trade Commission, Investigation No. 337-TA-1276, 380 pages. [uploaded in 9 parts].
Sep. 2, 2022 Respondent's Corrected Reply Post-Hearing Brief, *Masimo Corporation and Cercacor Laboratories, Inc. v. Apple Inc.,* United States International Trade Commission, Investigation No. 337-TA-1276, 191 pages.
Sep. 14, 2022 Respondent's Second Corrected Reply Post-Hearing Brief, *Masimo Corporation and Cercacor Laboratories, Inc. v. Apple Inc.,* United States International Trade Commission, Investigation No. 337-TA-1276, 312 pages.
Feb. 22, 2022 Deposition Transcript of Robert Rowe, Ph.D., *Masimo Corp et al. v. Apple Inc.,* ITC Inv. No 337-TA-1276, pp. 213.
Jun. 6, 2022 through Jun. 10, 2022 *Masimo Corp et al. v. Apple Inc.,* Public Hearing Transcript, ITC Inv. No 337-TA-1276, pp. 670.
Jan. 10, 2023 Notice of Final Initial Determination on Violation of Section 337, Inv. No 337-TA-1276, pp. 2.
Jan. 10, 2023 Final Initial Determination on Violation of Section 337, Inv. No 337-TA-1276, pp. 342. [Submitted in 10 parts].
Jan. 23, 2023 Respondent Apple Inc.'s Summary of Petition for Review of the Initial Determination of Violation of Section 337, Inv. No 337-TA-1276, pp. 25.
Jan. 24, 2023 Recommended Determination in Remedy and Bonding, Inv. No 337-TA-1276, pp. 7.
Jan. 31, 2023 Respondent Apple Inc.'s Response to Complainants' Petition for Review, Inv. No 337-TA-1276, pp. 105.
Jan. 31, 2023 Respondent Apple Inc.'s Summary of its Response to Complainants' Petition for Review, Inv. No 337-TA-1276, pp. 25.
Feb. 2, 2023 Complainants' Petition for Review of the Final Initial Determination on Violation of Section 337, Inv. No 337-TA-1276, pp. 104.
Feb. 2, 2023 Complainants' Summary of Petition for Review of the Final Initial Determination on Violation of Section 337, Inv. No 337-TA-1276, pp. 13.
Feb. 2, 2023 Respondent Apple Inc.'s Petition for Review of the Initial Determination of Violation of Section 337, Inv. No 337-TA-1276, pp. 120.
Feb. 10, 2023 Complainants' Response to Apple Inc.'s Petition for Review of the Final Initial Determination on Violation of Section 337, Inv. No 337-TA-1276, pp. 297.
Feb. 10, 2023 Complainants' Summary of Response to Apple's Petition for Review of the Final Initial Determination on Violation of Section 337, Inv. No 337-TA-1276, pp. 13.
May 15, 2023 Notice of a Commission Determination to Review in Part a Final Initial Determination; Request for Written Submissions on the Issues Under Review and on Remedy, The Public Interest, and Bonding, Inv. No 337-TA-1276, pp. 7.
International Trade Commission, Determination to Review, Federal Register, vol. 88, No. 97, May 19, 2023, Investigation No. 337-TA-1276, pp. 32243-32246.
Jun. 12, 2023 Complainants' Reply to Apple Inc.'s Response to the Commission's Notice to Review in Part a Final Initial Determination and Request for Written Submissions, Inv. No 337-TA-1276, pp. 65.
Jun. 12, 2023 Exhibits 54-93 for Complainants' Reply to Apple Inc.'s Response to the Commission's Notice to Review in Part a Final Initial Determination and Request for Written Submissions, Inv. No 337-TA-1276, pp. 590.
Jun. 15, 2023 Complainants' Submission in Response to the Commission's May 15, 2023 Notice of Commission Determination to Review in Part, Inv. No 337-TA-1276, pp. 130.
Jun. 15, 2023 Exhibits 1-53 of Complainants' Submission in Response to the Commission's May 15, 2023 Notice of Commission Determination to Review in Part, Inv. No 337-TA-1276, pp. 781. [uploaded in 2 parts].
Jun. 15, 2023 Respondent Apple Inc.'s Response to the Commissions' Notice to Review in Part a Final Initial Determination and Request for Written Submissions, Inv. No 337-TA-1276, pp. 263.
Jun. 22, 2023 Respondent Apple Inc.'s Reply to Complainants' Response to the Commission's Notice to|Review in Part a Final Initial Determination and Request for Written Submissions, Inv. No 337-TA-1276, pp. 60.

(56) References Cited

OTHER PUBLICATIONS

Jun. 23, 2023 Notice of Denial of Respondent Apple Inc.'s Request for Rehearing of Decisions Denying Institution of Inter Partes Review for U.S. Pat. No. 10,945,648, Inv. No 337-TA-1276, pp. 5.
Jun. 23, 2023 Exhibits A & B for Notice of Denial of Respondent Apple Inc.'s Request for Rehearing of Decisions Denying Institution of Inter Partes Review for U.S. Pat. No. 10,945,648, Inv. No 337-TA-1276, pp. 19.
Oct. 26, 2023 Limited Exclusion Order, Inv. No 337-TA-1276, pp. 4.
Oct. 30, 2023 Respondent Apple Inc.'s Motion to Stay Exclusion and Cease and Desist Orders Pending Appeal and/or in light of the Potential Government Shutdown, Inv. No 337-TA-1276, pp. 36.
International Trade Commission, Determination to Review, Federal Register, vol. 88, No. 210, Nov. 1, 2023, Investigation No. 337-TA-1276, pp. 75032-75033.
Nov. 9, 2023 Complainants' Opposition to Respondent Apple Inc.'s Motion to Stay Exclusion and Cease and Desist Orders Pending Appeal and/or in light of the Potential Government Shutdown, Inv. No 337-TA-1276, pp. 124.
Nov. 14, 2023 Commission Opinion [Public Version], Inv. No 337-TA-1276, pp. 124.
Dec. 26, 2023 Appellant Apple Inc.'s Non-Confidential Emergency Motion for an Immediate Interim Stay Pending Disposition of Motion for Stay Pending Appeal, Inv. No 337-TA-1276, pp. 15.
Dec. 26, 2023 Appellant Apple Inc.'s Non-Confidential Emergency Motion to Stay Enforcement of ITC's Orders Pending Review in Inter Partes Review, Inv. No 337-TA-1276, pp. 939. [Uploaded in 4 parts].
Dec. 26, 2023 Apple Inc.'s Petition for Review and Notice of Appeal Regarding U.S. Pat. No. 10,912,502 and U.S. Pat. No. 10,945,648, Inv. No 337-TA-1276, pp. 492. [Uploaded in 3 parts].
Jan. 3, 2024 Commission Opinion Denying Respondent's Motion to Stay the Remedial Orders [Public Version], Inv. No 337-TA-1276, pp. 14.
Jan. 10, 2024 Appellee International Trade Commission's Nonconfidential Response in Opposition to Appellant's Motion for a Stay Pending Appeal, Inv. No 337-TA-1276, pp. 137.
Jan. 10, 2024 Masimo Corporation and Cercacor Laboratories, Inc.'s Nonconfidential Opposition to AppleInc.'s Emergency Motion to Stay Enforcement of ITC's Orders Pending Review, Inv. No 337-TA-1276, pp. 34.
Jan. 10, 2024 Addendum, Declaration of Joe Kiani in Support of Masimo Corporation and Cercacor Laboratories, Inc.'s Opposition to Apple's Emergency Motion to Stay Enforcement Of ITC's Order Pending Review, Inv. No 337-TA-1276, pp. 67.
Jan. 10, 2024 Masimo Exhibits: Part 1 in Support of Opposition, Inv. No 337-TA-1276, pp. 468.
Jan. 10, 2024 Masimo Exhibits: Part 2 in Support of Opposition, Inv. No 337-TA-1276, pp. 138.
Jan. 12, 2024 Ruling; U.S. Customs and Border Protection; U.S. International Trade Commission; Limited Exclusion Order; HQ H335304, Inv. No. 337-TA-1276; pp. 31.
Jan. 15, 2024 Non-Confidential Reply in Support of Appellant Apple Inc.'s Emergency Motion to Stay Enforcement of ITC's Orders Pending Review, Inv. No 337-TA-1276, pp. 123.
Pulse Oximetry Sensor, U.S. Appl. No. 16/871,874.
Physiological Monitoring Devices, Systems, and Methods, U.S. Appl. No. 90/019,457.
Tilley, Aaron, "The Entrepreneur Who Bet His Company on a Fight with Apple", Wall Street Journal, Dec. 30, 2023, pp. 6.
File History of U.S. Pat. No. 10,448,871 issued Oct. 22, 2019 (U.S. Appl. No. 15/195,199, filed Jun. 28, 2016) in 530 pages. [Uploaded in 2 parts].
File History of U.S. Pat. No. 10,646,146 issued May 12, 2020 (U.S. Appl. No. 16/532,065, filed Aug. 5, 2019) in 163 pages.
Dec. 15, 2023 Excerpt of Expert Report of Majid Sarrafzadeh, Ph.D. Regarding Invalidity of U.S. Pat. No. 10,687,743 & U.S. Pat. No. 10,722,159, Apple Inc. v. Masimo Corporation and Sound United, LLC, Masimo Corporation v. Apple Inc., Case No. 1:22-cv-01377-

MN & Apple Inc. v. Masimo Corporation and Sound United, LLC, Masimo Corporation and Cercacor Laboratories, Inc. v. Apple Inc., Case No. 1:22-cv-01378-MN, 17 pages.
Various emails from Daniel Kiang & Nicholas Stephens re: Petition Correction, IPR2022-01291 as dated Aug. 31, 2022-Sep. 27, 2022, in 12 pages.
Email from Jamie Kringstein re: Prior Art Grounds, Apple v. Masimo Case Nos. 1:22-cv-01377-MN & 1:22-cv-01378-MN as dated Nov. 16, 2023, in 3 pages.
Various emails from Daniel Kiang, Andrew Patrick & Rick Bisenius re: IPR2024-00243/00244 as dated Mar. 6, 2024-Mar. 13, 2024, in 7 pages.
Sotera Stipulation by Apple Inc., Exhibit 1078, Apple Inc. v. Masimo Corporation, Inter Partes Review No. IPR2024-00241, dated May 20, 2024, in 6 pages.
Letter from Jennifer Shih to Masimo Corporation re 510(k) No. K232512, U.S. Food & Drug Administration, dated Nov. 17, 2023, in 14 pages.
Nonconfidential Brief of Appellant Masimo Corporation, Appeal from the United States Patent Office, Patent Trial and Appeal Board Case Nos. IPR2022-01291 and IPR2022-01465, Federal Circuit Case Nos. 2024-1635, -1636, Masimo Corporation v. Apple Inc., Sep. 10, 2024, in 418 pages.
Order, Conduct of the Proceedings for Inter Partes Review of U.S. Pat. No. 10,687,745, Ex. 2040, Apple Inc. v. Masimo Corporation, Inter Partes Review Nos. IPR2022-01291, IPR2022-01465, dated Sep. 5, 2023 in 6 pages.
Judgment, Final Written Decision, Apple Inc. v. Masimo Corporation, Inter Partes Review No. IPR2022-01465, dated Feb. 2, 2024, in 162 pages.
Petitioner's Updated Mandatory Notices, Apple Inc. v. Masimo Corporation, Inter Partes Review No. IPR2024-00241, dated Mar. 11, 2024, in 3 pages.
Email form PTAB Board Denying Request for Leave to File Motions to Correct and Corrected Petitions re: IPR2024-00241, 00242, 00243, 00244, dated Mar. 18, 2024 in 5 pages.
Patent Owner's Response to Petitioner's Notice Ranking Petitions, Apple Inc. v. Masimo Corporation, Inter Partes Review No. IPR2024-00241, dated Apr. 10, 2024, in 8 pages.
Patent Owner's Updated Mandatory Notices, Apple Inc. v. Masimo Corporation, Inter Partes Review No. IPR2024-00241, dated Apr. 10, 2024, in 5 pages.
Patent Owner's Preliminary Response, Apple Inc. v. Masimo Corporation, Inter Partes Review No. IPR2024-00241, dated Apr. 10, 2024, in 68 pages.
Petitioner's Reply to Patent Owner's Preliminary Response, Apple Inc. v. Masimo Corporation, Inter Partes Review No. IPR2024-00241, dated May 20, 2024, in 12 pages.
Patent Owner Masimo Corporation's Preliminary Sur-Reply, Apple Inc. v. Masimo Corporation, Inter Partes Review No. IPR2024-00241, dated May 28, 2024, in 14 pages.
Decision Granting Institution of Inter Partes Review 35 U.S.C. § 314, Apple Inc. v. Masimo Corporation, Inter Partes Review No. IPR2024-00241, dated Jul. 9, 2024, in 39 pages.
Curriculum Vitae of Vijay K. Madisetti, Ph.D. in Inter Partes Review of U.S. Pat. No. 10,687,743, Ex. 2001, Apple Inc. v. Masimo Corporation, Inter Partes Review No. IPR2024-00241, in 32 pages.
Declaration of Vijay K. Madisetti, Ph.D. in Inter Partes Review of U.S. Pat. No. 10,687,743, Ex. 2001, Apple Inc. v. Masimo Corporation, Inter Partes Review No. IPR2024-00241, in 56 pages.
Notice of Filing Date Accorded to Petition and Time for Filing Patent Owner Preliminary Response, Apple Inc. v. Masimo Corporation, Inter Partes Review No. IPR2024-00242, dated Jan. 10, 2024, in 6 pages.
Petitioner's Updated Mandatory Notices, Apple Inc. v. Masimo Corporation, Inter Partes Review No. IPR2024-00242, dated Mar. 11, 2024, in 3 pages.
Patent Owner's Preliminary Response, Apple Inc. v. Masimo Corporation, Inter Partes Review No. IPR2024-00242, dated Apr. 10, 2024, in 55 pages.
Patent Owners Response to Petitioner's Notice Ranking Petitions, Apple Inc. v. Masimo Corporation, Inter Partes Review No. IPR2024-00242, dated Apr. 10, 2024, in 8 pages.

(56) References Cited

OTHER PUBLICATIONS

Patent Owners Updated Mandatory Notices, *Apple Inc.* v. *Masimo Corporation,* Inter Partes Review No. IPR2024-00242, dated Apr. 10, 2024, in 5 pages.

Petitioner's Reply to Patent Owner's Preliminary Response, *Apple Inc.* v. *Masimo Corporation,* Inter Partes Review No. IPR2024-00242, dated May 20, 2024, in 9 pages.

Patent Owner Masimo Corporation's Preliminary Sur-Reply, *Apple Inc.* v. *Masimo Corporation,* Inter Partes Review No. IPR2024-00242, dated May 28, 2024, in 10 pages.

Decision Denying Institution of Inter Partes Review 35 U.S.C. § 314, *Apple Inc.* v. *Masimo Corporation,* Inter Partes Review No. IPR2024-00242, dated Jul. 9, 2024, in 16 pages.

Patent Owner's Preliminary Response, *Apple Inc.* v. *Masimo Corporation,* Inter Partes Review No. IPR2024-00243, dated Apr. 11, 2024, in 69 pages.

Patent Owners Response to Petitioner's Notice Ranking Petitions, *Apple Inc.* v. *Masimo Corporation,* Inter Partes Review No. IPR2024-00243, dated Apr. 11, 2024, in 8 pages.

Patent Owners Updated Mandatory Notices, *Apple Inc.* v. *Masimo Corporation,* Inter Partes Review No. IPR2024-00243, dated Apr. 11, 2024, in 5 pages.

Petitioner's Reply to Patent Owner's Preliminary Response, *Apple Inc.* v. *Masimo Corporation,* Inter Partes Review No. IPR2024-00243, dated May 20, 2024, in 14 pages.

Patent Owner Masimo Corporation's Preliminary Sur-Reply, *Apple Inc.* v. *Masimo Corporation,* Inter Partes Review No. IPR2024-00243, dated May 28, 2024, in 14 pages.

Decision Granting Institution of Inter Partes Review 35 U.S.C. § 314, *Apple Inc.* v. *Masimo Corporation,* Inter Partes Review No. IPR2024-00243, dated Jul. 9, 2024, in 41 pages.

Patent Owner's Preliminary Response, *Apple Inc.* v. *Masimo Corporation,* Inter Partes Review No. IPR2024-00244, dated Apr. 11, 2024, in 65 pages.

Patent Owners Response to Petitioner's Notice Ranking Petitions, *Apple Inc.* v. *Masimo Corporation,* Inter Partes Review No. IPR2024-00244, dated Apr. 11, 2024, in 8 pages.

Patent Owners Updated Mandatory Notices, *Apple Inc.* v. *Masimo Corporation,* Inter Partes Review No. IPR2024-00244, dated Apr. 11, 2024, in 5 pages.

Petitioner's Reply to Patent Owner's Preliminary Response, *Apple Inc.* v. *Masimo Corporation,* Inter Partes Review No. IPR2024-00244, dated May 20, 2024, in 11 pages.

Patent Owner Masimo Corporation's Preliminary Sur-Reply, *Apple Inc.* v. *Masimo Corporation,* Inter Partes Review No. IPR2024-00244, dated May 28, 2024, in 10 pages.

Decision Granting Institution of Inter Partes Review 35 U.S.C. § 314, *Apple Inc.* v. *Masimo Corporation,* Inter Partes Review No. IPR2024-00244, dated Jul. 9, 2024, in 37 pages.

Decision Denying Institution of Inter Partes Review of U.S. Pat. No. 10,912,501, *Apple Inc.* v. *Masimo Corporation,* Inter Partes Review No. IPR2022-01271, dated Jan. 24, 2023, in 21 pages.

Decision Denying Institution of Inter Partes Review of U.S. Pat. No. 10,912,501, *Apple Inc.* v. *Masimo Corporation,* Inter Partes Review No. IPR2022-01272, dated Jan. 24, 2023, in 21 pages.

Decision Denying Institution of Inter Partes Review of U.S. Pat. No. 10,912,502, *Apple Inc.* v. *Masimo Corporation,* Inter Partes Review No. IPR2022-01273, dated Jan. 24, 2023, in 24 pages.

Decision Denying Institution of Inter Partes Review of U.S. Pat. No. 10,912,502, *Apple Inc.* v. *Masimo Corporation,* Inter Partes Review No. IPR2022-01274, dated Jan. 24, 2023, in 21 pages.

Decision Denying Institution of Inter Partes Review of U.S. Pat. No. 10,945,648, *Apple Inc.* v. *Masimo Corporation,* Inter Partes Review No. IPR2022-01275, dated Jan. 30, 2023, in 34 pages.

Decision Denying Institution of Inter Partes Review of U.S. Pat. No. 10,945,648, *Apple Inc.* v. *Masimo Corporation,* Inter Partes Review No. IPR2022-01276, dated Jan. 30, 2023, in 27 pages.

Non-Confidential Brief for Appellee Apple Inc., Inter Partes Review Nos. IPR2022-01291 and IPR2022-01465, filed Nov. 4, 2024, in 77 pages.

Sep. 24, 2024 Declaration of Edward M. Cannon in Support of Masimo's Motion to Supplement the Claim Construction Record, Including Exhibits 52-55 and 57-62, *Apple Inc.* v. *Masimo Corporation and Sound United, LLC,* Case Nos. 1:22-cv-01377-JLH and 1:22-cv-01378-JLH, 681 pages.

Sep. 26, 2024 [Proposed] Final Jury Instructions, *Apple Inc.* v. *Masimo Corporation and Sound United, LLC,* Case Nos. 1:22-cv-01377-JLH and 1:22-cv-01378-JLH, 97 pages.

Oct. 17, 2024 Masimo's Notice of Masimo Defenses no Longer Asserted, *Apple Inc.* v. *Masimo Corporation and Sound United, LLC,* Case Nos. 1:22-cv-01377-JLH and 1:22-cv-01378-JLH, 2 pages.

Oct. 22, 2024 Letter to the Honorable Jennifer L. Hall from David E. Moore, *Apple Inc.* v. *Masimo Corporation and Sound United, LLC,* Case Nos. 1:22-cv-01377-JLH and 1:22-cv-01378-JLH, 5 pages.

Oct. 22, 2024 Letter to the Honorable Jennifer L. Hall from John C. Phillips, Jr., *Apple Inc.* v. *Masimo Corporation and Sound United, LLC,* Case Nos. 1:22-cv-01377-JLH and 1:22-cv-B60801378-JLH, 3 pages.

Sep. 24, 2024 Masimo's Brief in Support of Motion to Supplement the Claim Construction Record, *Apple Inc.* v. *Masimo Corporation and Sound United, LLC,* Case Nos. 1:22-cv-01377-JLH and 1:22-cv-01378-JLH, 8 pages.

Oct. 7, 2024 Memorandum Order, *Apple Inc.* v. *Masimo Corporation and Sound United, LLC,* Case Nos. 1:22-cv-01377-JLH and 1:22-cv-01378-JLH, 16 pages.

Oct. 8, 2024 Apple Inc.'s Opposition to Masimo's Motion to Supplement the Claim Construction Record, *Apple Inc.* v. *Masimo Corporation and Sound United, LLC,* Case Nos. 1:22-cv-01377-JLH and 1:22-cv-01378-JLH, 3 pages.

Oct. 8, 2024 Markman Opinion, *Apple Inc.* v. *Masimo Corporation and Sound United, LLC,* LLC, Case Nos. 1:22-cv-01377-JLH and 1:22-cv-01378-JLH, 15 pages.

Oct. 8, 2024 Memorandum Order, *Apple Inc.* v. *Masimo Corporation and Sound United, LLC,* Case Nos. 1:22-cv-01377-JLH and 1:22-cv-01378-JLH, 4 pages.

Oct. 9, 2024 Masimo's Reply Brief in Support of Motion to Supplement the Claim Construction Record, *Apple Inc.* v. *Masimo Corporation and Sound United, LLC,* LLC, Case Nos. 1:22-cv-01377-JLH and 1:22-cv-01378-JLH, 6 pages.

Oct. 9, 2024 Memorandum Order, *Apple Inc.* v. *Masimo Corporation and Sound United, LLC,* LLC, Case Nos. 1:22-cv-01377-JLH and 1:22-cv-01378-JLH, 7 pages.

Oct. 10, 2024 Markman Opinion and Order, *Apple Inc.* v. *Masimo Corporation and Sound United, LLC,* Case Nos. 1:22-cv-01377-JLH and 1:22-cv-01378-JLH, 11 pages.

Oct. 10, 2024 Memorandum Order, *Apple Inc.* v. *Masimo Corporation and Sound United, LLC,* Case Nos. 1:22-cv-01377-JLH and 1:22-cv-01378-JLH, 4 pages.

Oct. 25, 2024 Final Jury Instructions, *Apple Inc.* v. *Masimo Corporation and Sound United, LLC,* Case Nos. 1:22-cv-01377-JLH and 1:22-cv-01378-JLH, 54 pages.

Oct. 25, 2024 Verdict Form, *Apple Inc.* v. *Masimo Corporation and Sound United, LLC,* Case Nos. 1:22-cv-01377-JLH and 1:22-cv-01378-JLH, 7 pages.

Nov. 13, 2024 Judgement Following Jury Verdict, *Apple Inc.* v. *Masimo Corporation and Sound United, LLC, Masimo Corporation and Sound United. LLC.* v. *Apple Inc.,* Case No. 1:22-cv-01378-JLH, 4 pages.

Letter to Chief Terrill from Secretary to the Commission, Lisa R. Barton Re: Certain Light-Based Physiological Measurement Devices and Components Thereof, Investigation No. 337-TA-1276, Dated Oct. 2, 2024, 3 pages.

Jun. 3, 2024 Corrected Non-Confidential Brief for Appellant Apple Inc., vol. 1, Federal Circuit appeal of ITC Inv. No 337-TA-1276, pp. 576. [Uploaded in 11 parts].

Jun. 3, 2024 Corrected Non-Confidential Brief for Appellant Apple Inc., vol. 2, Federal Circuit appeal of ITC Inv. No 337-TA-1276, pp. 338. [Uploaded in 4 parts].

Jun. 28, 2024 Nonconfidential Brief of Appellee International Trade Commission, Federal Circuit appeal of ITC Inv. No 337-TA-1276, pp. 84.

(56) References Cited

OTHER PUBLICATIONS

Jun. 28, 2024 Nonconfidential Brief of Intervenors Masimo Corporation and Cercacor Laboratories, Inc., Federal Circuit appeal of ITC Inv. No 337-TA-1276, pp. 87.

Jul. 10, 2024 Corrected Nonconfidential Brief of Intervenors Masimo Corporation and Cercacor Laboratories, Inc., Federal Circuit appeal of ITC Inv. No 337-TA-1276, pp. 87.

Jul. 8, 2024 Non-Confidential Joint Appendix vols. 1-9, Federal Circuit appeal of ITC Inv. No 337-TA-1276, pp. 5349. [Uploaded in 15 parts].

Fontaine, et al. "Reflectance-Based Pulse Oximetry for the Chest and Wrist," Apr. 2013, pp. 131, https://digital.wpi.edu/pdfviewer/70795903r.

"COVID-19 Clinical management", apps.who.int (Jan. 25, 2021), available at https://apps.who.int/iris/bitstream/handle/10665/338882/WHO-2019-nCoV-clinical-2021.1-eng.pdf?sequence=1&isAllowed=y, Ex. 2006 in Inter Partes Review of U.S. Pat. No. 10,470,695, Apple Inc. v. Masimo Corporation, Inter Partes Review No. IPR2020-01722, in 81 pages.

Cohen et al., "A plan to save coronavirus patients from dying at home," cnn.com (Apr. 12, 2020), available at https://www.cnn.com/2020/04/11/health/monitoring-covid19-athome/index.html, Ex. 2007 in Inter Partes Review of U.S. Pat. No. 10,470,695, Apple Inc. v. Masimo Corporation, Inter Partes Review No. IPR2020-01722, in 5 pages.

Morey et al., "Feasibility and accuracy of nasal alar pulse oximetry," British Journal of Anaesthesia, vol. 112, Issue 6, 1109-04 (Jun. 2014), Ex. 2008 in Inter Partes Review of U.S. Pat. No. 10,470,695, Apple Inc. v. Masimo Corporation, Inter Partes Review No. IPR2020-01722, in 6 pages.

Geun et al., "Measurement Site and Applied Pressure Consideration in Wrist Photoplethysmography," The 23rd International Technical Conference on Circuits/Systems, Computers and Communications, 1129-1132 (Jan. 2008), Ex. 2009 in Inter Partes Review of U.S. Pat. No. 10,470,695, Apple Inc. v. Masimo Corporation, Inter Partes Review No. IPR2020-01722, in 4 pages.

R.J. Duckworth et al., "Field Testing of a Wireless Wearable Reflectance Pulse Oximeter," American Telemedicine Association Annual Conference, 2006, in Inter Partes Review of U.S. Pat. No. 10,687,745, Ex. 2005, Apple Inc. v. Masimo Corporation, Inter Partes Review Nos. IPR2020-01291, IPR2022-01292, in 1 pages.

Y. Mendelson, "Wearable Wireless Pulse Oximetry for Physiological Monitoring," Worcester Polytechnic Institute Precise Personnel Location Workshop, 2008, in Inter Partes Review of U.S. Pat. No. 10,687,745, Ex. 2006, Apple Inc. v. Masimo Corporation, Inter Partes Review Nos. IPR2020-01291, IPR2022-01292, dated Aug. 4, 2008, in 34 pages.

Griffin, "Apple Watch Series 6: Why Apple Added a Sensor toTell How Much Oxygen Is in Your Blood as Its Big New Feature—And What It Means,"Independent, Oct. 7, 2020 (https://www.independent.co.uk/tech/apple-watch-series-6-bloodoxygen-pulse-oximetry-red-light-heart-rate-vo2-max-b513807.html).

Chen, "The New Apple Watch Measures Your Blood Oxygen. Now What?," New York Times, Sep. 17, 2020 (https://www.nytimes.com/2020/09/17/technology/personaltech/newapple-watch-blood-oxygen-level-review.html).

Polymers and Plastic Resins Information, Engineering360, printed from https://www.globalspec.com/learnmore/materials_chemicals_adhesives/plastics_elastomers_polymers/plastics_polymers on Aug. 15, 2022.

Methods and Approaches of Futures Studies, printed from http://crab.rutgers.edu/~goertzel/futuristmethods.html on Aug. 15, 2022.

Findings of Fact & Conclusions of Law, Masimo Corp. v. True Wearables, Inc., No. 8:18-cv-02001-JVS-JDE, Dkt. 600 (C.D. Cal. Nov. 7, 2022).

Eric W. Weisstein, Annulus, Wolfram MathWorld (Dec. 1, 2022, 3:20 PM), https://mathworld.wolfram.com/Annulus.html.

Sep. 15, 2020 Apple Press Release Regarding Apple Watch Series 6.

Apple Webpage Titled "Apple Watch Series 6".

"Track Your SpO2 to Uncover Changes in Your Wellbeing," Fitbit, Sept. 7, 2020, Ex. 2092 in Inter Partes Review of U.S. Pat. No. 10,687,745, Apple Inc. v. Masimo Corporation, Inter Partes Review Nos. IPR2022-01291, IPR2022-01465, in 3 pages.

Decision Denying Institution of Inter Partes Review of U.S. Pat. No. 10,687,745, Apple Inc. v. Masimo Corporation, Inter Partes Review No. IPR2022-01466, dated Feb. 23, 2023, in 13 pages.

Encyclopedia Britannica, Light, the visible spectrum, https://www.britannica.com/science/light (last visited May 19, 2023), Ex. 2073 in Inter Partes Review of U.S. Pat. No. 10,687,745, Apple Inc. v. Masimo Corporation, Inter Partes Review Nos. IPR2022-01291, IPR2022-01465, in 1 page.

Excerpts of Webster's II New Collegiate Dictionary (2001), Ex. 2072 in Inter Partes Review of U.S. Pat. No. 10,687,745, Apple Inc. v. Masimo Corporation, Inter Partes Review Nos. IPR2022-01291, IPR2022-01465, in 3 pages.

ITC Exhibit CX-1616—Fowler, Geoffrey, "The new Apple Watch says my lungs may be sick. Or perfect. It can't decide." Washington Post, Sep. 23, 2020, Ex. 2088 in Inter Partes Review of U.S. Pat. No. 10,687,745, Apple Inc. v. Masimo Corporation, Inter Partes Review Nos. IPR2022-01291, IPR2022-01465, in 6 pages.

Kim, Gina, "Masimo Wants $3B From Apple Over Smartwatch IP, Jury Told." Law360, Apr. 5, 2023, Ex. 2087 in Inter Partes Review of U.S. Pat. No. 10,687,745, Apple Inc. v. Masimo Corporation, Inter Partes Review Nos. IPR2020-01291, IPR2022-01465, in 4 pages.

Redacted Declaration of R. James Duckworth in Support of Patent Owner's Response of U.S. Pat. No. 10,687,745, Apple Inc. v. Masimo Corporation, Inter Partes Review No. IPR2022-01465, dated May 26, 2023, in 79 pages.

Redacted Patent Owner Response of U.S. Pat. No. 10,687,745, Apple Inc. v. Masimo Corporation, Inter Partes Review No. IPR2022-01291, dated May 26, 2023, in 82 pages.

Redacted Patent Owner Response of U.S. Pat. No. 10,687,745, Apple Inc. v. Masimo Corporation, Inter Partes Review No. IPR2022-01465, dated May 26, 2023, in 79 pages.

RX-0504: "Optimization of Reflectance-Mode Pulse Oximeter Sensors", Ex. 1039 in Inter Partes Review of U.S. Pat. No. 10,687,745, Apple Inc. v. Masimo Corporation, Inter Partes Review Nos. IPR2022-01291, IPR2022-01465, in 1 page.

RX-0508: Yao et al., "Stimulating Student Learning with a Novel 'In House' Pulse Oximeter Design", Ex. 1040 in Inter Partes Review of U.S. Pat. No. 10,687,745, Apple Inc. v. Masimo Corporation, Inter Partes Review Nos. IPR2022-01291, IPR2022-01465, IPR2024-00234, in 14 pages.

Rx-0632, Ex. 1041 in Inter Partes Review of U.S. Pat. No. 10,687,745, Apple Inc. v. Masimo Corporation, Inter Partes Review Nos. IPR2022-01291, IPR2022-01465, in 1 page.

Transcript of Mar. 24, 2023 Deposition of Dr. Brian W. Anthony and Exhibits 1-3 Thereto, Ex. 2071 in Inter Partes Review of U.S. Pat. No. 10,687,745, Apple Inc. v. Masimo Corporation, Inter Partes Review Nos. IPR2022-01291, IPR2022-01465, in 393 pages.

William, Andrews, "Fitbit Update Lets You Quickly Check Your Blood Oxygen Saturation." Forbes, Sept. 9, 2020, Ex. 2091 in Inter Partes Review of U.S. Pat. No. 10,687,745, Apple Inc. v. Masimo Corporation, Inter Partes Review Nos. IPR2022-01291, IPR2022-01465, in 6 pages.

"Beam Shaping with Cylindrical Lenses", [Retrieved on Aug. 19, 2023], URL: https://www.newport.com/n/beam-shaping-with-cylindrical-lenses, Ex. 1076 in Inter Partes Review of U.S. Pat. No. 10,687,745, Apple Inc. v. Masimo Corporation, Inter Partes Review Nos. IPR2022-01291, IPR2022-01465, IPR2024-00244, in 2 pages.

Bronzino, The Biomedical Engineering Handbook, CRC Press, Inc., dated 1995, Ex. 1046 in Inter Partes Review of U.S. Pat. No. 10,687,745, Apple Inc. v. Masimo Corporation, Inter Partes Review Nos. IPR2022-01291, IPR2022-01465, in 78 pages.

Cai, et al., "Implementation of a Wireless Pulse Oximeter Based on Wrist Band Sensor", IEEE, dated 2010, pp. 1897-1900, Ex. 1053 in Inter Partes Review of U.S. Pat. No. 10,687,745, Apple Inc. v. Masimo Corporation, Inter Partes Review Nos. IPR2022-01291, IPR2022-01465, in 4 pages.

(56) References Cited

OTHER PUBLICATIONS

Deposition of Dr. R. James Duckworth, Ph.D., , Ex. 1059, *Apple Inc. v. Masimo Corporation*, Inter Partes Review No. IPR2022-01291, dated Aug. 9, 2023, in 137 pages.

Dickey, Laser Beam Shaping: Theory and Techniques, Second Edition, CRC Press, dated 2014, Ex. 1077 in Inter Partes Review of U.S. Pat. No. 10,687,745, *Apple Inc. v. Masimo Corporation*, Inter Partes Review Nos. IPR2022-01291, IPR2022-01465, in 583 pages.

Duffy, "MIO Alpha BLE Review", PCmag.com, dated Jan. 28, 2013, Ex. 1049 in Inter Partes Review of U.S. Pat. No. 10,687,745, *Apple Inc. v. Masimo Corporation*, Inter Partes Review Nos. IPR2022-01291, IPR2022-01465, in 6 pages.

Excerpt of Collins Dictionary, Tenth Edition, HarperCollins Publishers, dated 2009, Ex. 1044 in Inter Partes Review of U.S. Pat. No. 10,687,745, *Apple Inc. v. Masimo Corporation*, Inter Partes Review Nos. IPR2022-01291, IPR2022-01465, in 3 pages.

Excerpt of Merriam-Webster's Collegiate Dictionary, Eleventh Edition, Merriam-Webster, Incorporated, dated 2014, Ex. 1045 in Inter Partes Review of U.S. Pat. No. 10,687,745, *Apple Inc. v. Masimo Corporation*, Inter Partes Review Nos. IPR2022-01291, IPR2022-01465, in 4 pages.

Excerpt of The American Heritage Dictionary, Fifth Edition, Houghton Mifflin Harcourt Publishing Company, dated 2011, Ex. 1043 in Inter Partes Review of U.S. Pat. No. 10,687,745, *Apple Inc. v. Masimo Corporation*, Inter Partes Review Nos. IPR2022-01291, IPR2022-01465, in 4 pages.

Lee, et al., "Micro-LED Technologies and Applications", Information Display 6/16, dated 2016, pp. 16-23, Ex. 1078 in Inter Partes Review of U.S. Pat. No. 10,687,745, *Apple Inc. v. Masimo Corporation*, Inter Partes Review Nos. IPR2022-01291, IPR2022-01465, in 8 pages.

Li, et al., "A Wireless Reflectance Pulse Oximeter With Digital Baseline Control for Unfiltered Photoplethysmograms", IEEE Transactions on Biomedical Circuits and Systems, vol. 6, No. 3, dated Jun. 2012, pp. 269-278, Ex. 1051 in Inter Partes Review of U.S. Pat. No. 10,687,745, *Apple Inc. v. Masimo Corporation*, Inter Partes Review Nos. IPR2022-01291, IPR2022-01465, in 10 pages.

Määttälä, et al., "Optimum Place for Measuring Pulse Oximeter Signal in Wireless Sensor-Belt or Wrist-Band", IEEE, dated 2007, pp. 1856-1861, Ex. 1055 in Inter Partes Review of U.S. Pat. No. 10,687,745, *Apple Inc. v. Masimo Corporation*, Inter Partes Review Nos. IPR2022-01291, IPR2022-01465, in 6 pages.

Pang, et al., "A Neo-Reflective Wrist Pulse Oximeter", IEEE Access, vol. 2, dated 2014, pp. 1562-1567, Ex. 1050 in Inter Partes Review of U.S. Pat. No. 10,687,745, *Apple Inc. v. Masimo Corporation*, Inter Partes Review Nos. IPR2022-01291, IPR2022-01465, in 6 pages.

Public Hearing Transcript of Dr. Saahil Mehra, Ph. D., Ex. 1037, *Apple Inc. v. Masimo Corporation*, Inter Partes Review No. IPR2022-01291, in 21 pages.

Public Hearing Transcript of Dr. Ueyn Block, Ph. D., Ex. 1036, *Apple Inc. v. Masimo Corporation*, Inter Partes Review No. IPR2022-01291, in 23 pages.

Severinghaus, et al., "Recent Developments in Pulse Oximetry", Anesthesiology, vol. 76, dated 1992, pp. 1018-1038, Ex. 1048 in Inter Partes Review of U.S. Pat. No. 10,687,745, *Apple Inc. v. Masimo Corporation*, Inter Partes Review Nos. IPR2022-01291, IPR2022-01465, in 21 pages.

Stein, "Withings Pulse O2 review: Fitness band plus heart rate monitor checks blood oxygen, too", CNET, dated 2023, Ex. 1057 in Inter Partes Review of U.S. Pat. No. 10,687,745, *Apple Inc. v. Masimo Corporation*, Inter Partes Review Nos. IPR2022-01291, IPR2022-01465 in 16 pages.

Supplemental Declaration of Dr. Brian W. Anthony, Ph. D., in support of Petition for Inter Partes Review of U.S. Pat. No. 10,687,745, Ex. 1042 , *Apple Inc. v. Masimo Corporation*, Inter Partes Review Nos. IPR2022-01291, IPR2022-01465, dated Aug. 21, 2023, in 96 pages.

Second Supplemental Declaration of Brian W. Anthony, Ph. D., *Apple Inc. v. Masimo Corporation*, Inter Partes Review Nos. IPR2022-01291, IPR2022-01465 dated Sep. 12, 2023, in 5 pages.

Takatani, et al., "Optical Oximetry Sensors for Whole Blood and Tissue", IEEE Engineering in Medicine and Biology, dated 1994, pp. 347-357, Ex. 1069 in Inter Partes Review of U.S. Pat. No. 10,687,745, *Apple Inc. v. Masimo Corporation*, Inter Partes Review Nos. IPR2022-01291, IPR2022-01465, in 11 pages.

Redacted Transcript of Deposition of Dr. Brian W. Anthony in Inter Partes Review of U.S. Pat. No. 10,687,745, *Apple Inc. v. Masimo Corporation*, Inter Partes Review Nos. IPR2022-01291, IPR2022-01465, dated Sep. 15, 2023, in 219 pages.

Webster, J.G., "Design of Pulse Oximeters", Institution of Physics Publishing, 1997, 262 pages.

File History of U.S. Pat. No. 10,687,743 issued Jun. 23, 2020 (U.S. Appl. No. 16/791,955, filed Feb. 14, 2020) in 425 pages.

File History of U.S. Pat. No. 10,722,159 issued Jul. 28, 2020 (U.S. Appl. No. 16/791,963, filed Feb. 14, 2020) in 272 pages.

Jun. 29, 2021 Redacted Complaint under Section 337 of the Tariff Act of 1930, as Amended, *Masimo Corporation and Cercacor Laboratories, Inc. v. Apple Inc.*, United States International Trade Commission, Investigation No. 337-TA-1276, 45 pages.

Excerpt of The Longman Dictionary of American English, Fifth Edition, Pearson Education Limited, dated 2014, Ex. 1026 in Inter Partes Review of U.S. Pat. No. 10,687,743, *Apple Inc. v. Masimo Corporation*, Inter Partes Review No. IPR2024-00241, in 3 pages.

Excerpt of The Dictionary of Science and Technology, Second Edition, A&C Black Publishers Ltd., dated 2007, Ex. 1027 in Inter Partes Review of U.S. Pat. No. 10,687,743, *Apple Inc. v. Masimo Corporation*, Inter Partes Review No. IPR2024-00241, in 3 pages.

Excerpt of Concise Encyclopedia of Science & Technology, Sixth Edition, McGraw-Hill, dated 1987, Ex. 1024 in Inter Partes Review of U.S. Pat. No. 10,687,743, *Apple Inc. v. Masimo Corporation*, Inter Partes Review No. IPR2024-00241, in 3 pages.

Excerpt of A Dictionary of Chemistry, Sixth Edition, Oxford University Press, dated 2008, Ex. 1025 in Inter Partes Review of U.S. Pat. No. 10,687,743, *Apple Inc. v. Masimo Corporation*, Inter Partes Review No. IPR2024-00241, in 3 pages.

Excerpt of Chambers Dictionary of Science and Technology, First Edition, Chambers Harrap Publishers Ltd., dated 2007, Ex. 1023 in Inter Partes Review of U.S. Pat. No. 10,687,743, *Apple Inc. v. Masimo Corporation*, Inter Partes Review No. IPR2024-00241, in 3 pages.

Nov. 22, 2023 Excerpt of Expert Report of Majid Sarrafzadeh, Ph.D. Regarding Invalidity of U.S. Pat. No. 10,687,743 & U.S. Pat. No. 10,722,159, *Apple Inc. v. Masimo Corporation and Sound United, LLC, Masimo Corporation v. Apple Inc.*, Case No. 1:22-cv-01377-MN & *Apple Inc. v. Masimo Corporation and Sound United, LLC, Masimo Corporation and Cercacor Laboratories, Inc. v. Apple Inc.*, Case No. 1:22-cv- 01378-MN, 7 pages.

Email from Nicholas Zovko re: Masimo's Prior Art Grounds, *Apple v. Masimo* Case Nos. 1:22-cv-01377-MN & 1:22-cv-01378-MN as dated Nov. 16, 2023, in 2 pages.

Fitbit Surge, User Manual, Version 1.3, 2014, in 47 pages.

Duffy, Jill, "Fitbit Surge Review", PC Magazine, available at https://www.pcmag.com/reviews/fitbitsurge, Jan. 29, 2015, in 18 pages.

Declaration of Brian W. Anthony, Ph.D., in support of Petition for Inter Partes Review of U.S. Pat. No. 10,470,695, Ex. 1003, *Apple Inc. v. Masimo Corporation*, Inter Partes Review No. IPR2020-01722, dated Oct. 1, 2020, in 134 pages.

Declaration of Jacob Robert Munford, in support of Petition for Inter Partes Review of U.S. Pat. No. 10,470,695, Ex. 1017, *Apple Inc. v. Masimo Corporation*, Inter Partes Review No. IPR2020-01722, dated Sep. 29, 2020, in 13 pages.

Petition for Inter Partes Review of U.S. Pat. No. 10,470,695, *Apple Inc. v. Masimo Corporation*, Inter Partes Review No. IPR2020-01722, dated Oct. 2, 2020, in 121 pages.

Decision Granting Institution of Inter Partes Review of U.S. Pat. No. 10,470,695, *Apple Inc. v. Masimo Corporation*, Inter Partes Review No. IPR2020-01722, dated May 12, 2021, in 26 pages.

(56)　　　　　References Cited

OTHER PUBLICATIONS

Masimo Response to Petition for Inter Partes Review of U.S. Pat. No. 10,470,695, *Apple Inc.* v. *Masimo Corporation,* Inter Partes Review No. IPR2020-01722, dated Aug. 9, 2021, in 51 pages.

Petitioner's Reply to Patent Owner Response for Inter Partes Review of U.S. Pat. No. 10,470,695, *Apple Inc.* v. *Masimo Corporation,* Inter Partes Review No. IPR2020-01722, dated Nov. 5, 2021, in 23 pages.

Declaration of Vijay K. Madisetti, Ph.D. in Inter Partes Review of U.S. Pat. No. 10,470,695, Ex. 2001, *Apple Inc.* v. *Masimo Corporation,* Inter Partes Review No. IPR2020-01722, dated Aug. 9, 2021, in 55 pages.

Curriculum Vitae of Vijay K. Madisetti, Ph.D. in Inter Partes Review of U.S. Pat. No. 10,470,695, Ex. 2002, *Apple Inc.* v. *Masimo Corporation,* Inter Partes Review No. IPR2020-01722, in 27 pages.

Transcript of Deposition of Dr. Brian W. Anthony in Inter Partes Review of U.S. Pat. No. 10,470,695, Ex. 2003, *Apple Inc.* v. *Masimo Corporation,* Inter Partes Review No. IPR2020-01722, dated Jul. 16, 2021, in 163 pages.

Statutory disclaimer filed for U.S. Pat. No. 10,470,695, dated Aug. 9, 2021, Ex. 2004 in Inter Partes Review of U.S. Pat. No. 10,470,695, *Apple Inc.* v. *Masimo Corporation,* Inter Partes Review No. IPR2020-01722, in 2 pages.

Transcript of Deposition of Dr. Vijay Madisetti in Inter Partes Review of U.S. Pat. No. 10,470,695, Ex. 1022, *Apple Inc.* v. *Masimo Corporation,* Inter Partes Review No. IPR2020-01722, dated Sep. 10, 2021, in 67 pages.

Masimo Sur-Reply to Petitioner Reply, Inter Partes Review No. IPR2020-01722, dated Dec. 17, 2021, in 21 pages.

Apple (Petitioner) Demonstratives for Oral Argument, Inter Partes Review No. IPR2020-01722, Feb. 2, 2022, in 44 pages.

Apple (Petitioner) Corrected Demonstratives for Oral Argument, Inter Partes Review No. IPR2020-01722, Feb. 2, 2022, in 44 pages.

Masimo Demonstratives for Oral Argument, Inter Partes Review No. IPR2020-01722, dated Feb. 9, 2022, in 33 pages.

Record of Oral Hearing held on Feb. 9, 2022, Inter Partes Review No. IPR2020-01722, in 37 pages.

Judgment, Final Written Decision Determining All Challenged Claims Unpatentable, Inter Partes Review No. IPR2020-01722, dated May 5, 2022, in 31 pages.

Masimo (Patent Owner's) Notice of Appeal to the U.S. Court of Appeals for the Federal Circuit, Inter Partes Review No. IPR2020-01722, dated Jun. 13, 2022, in 37 pages.

Masimo (Patent Owner's) Opening Brief to the U.S. Court of Appeals for the Federal Circuit, Inter Partes Review No. IPR2020-01722, dated Nov. 7, 2022, in 127 pages.

Apple Inc.'s Response Brief of U.S. Pat. No. 10,470,695, *Masimo Corporation* v. *Apple Inc.,* Appeal No. 22-1895, dated Feb. 1, 2023, in 67 pages.

Joint Appendix vol. 1 & vol. 2, Federal Circuit Appeal from the Patent Trial and Appeal Board Case No. IPR2020-01722, Case No. 22-1895, *Masimo Corporation* v. *Apple Inc.,* as filed Apr. 14, 2023 in 483 pages.

Reply Brief of Appellant Masimo Corporation, Federal Circuit Appeal from the Patent Trial and Appeal|Board Case No. IPR2020-01722, Case No. 22-1895, *Masimo Corporation* v. *Apple Inc.,* as filed Apr. 9, 2023 in 39 pages.

Declaration of Brian W. Anthony, Ph.D., in support of Petition for Inter Partes Review of U.S. Pat. No. 10,470,695, Ex. 1003, *Apple Inc.* v. *Masimo Corporation,* Inter Partes Review No. IPR2020-01723, dated Oct. 2, 2020, in 95 pages.

Declaration of Jacob Robert Munford, in support of Petition for Inter Partes Review of U.S. Pat. No. 10,470,695, Ex. 1017, *Apple Inc.* v. *Masimo Corporation,* Inter Partes Review No. IPR2020-01723, dated Sep. 29, 2020, in 81 pages.

Petition for Inter Partes Review of U.S. Pat. No. 10,470,695, *Apple Inc.* v. *Masimo Corporation,* Inter Partes Review No. IPR2020-01723, dated Oct. 2, 2020, in 87 pages.

Petitioner's Notice Ranking And Explaining Material Differences Between Petitions for Inter Partes Review of U.S. Pat. No. 10,470,695, Inter Partes Review Nos. IPR2020-01722, IPR2020-01723, dated Oct. 2, 2020, in 5 pages.

Decision Denying Institution of Inter Partes Review of U.S. Pat. No. 10,470,695, *Apple Inc.* v. *Masimo Corporation,* Inter Partes Review No. IPR2020-01723, dated May 12, 2021, in 15 pages.

Petition for Inter Partes Review of U.S. Pat. No. 10,687,745, *Apple Inc.* v. *Masimo Corporation,* Inter Partes Review No. IPR2022-01291, dated Jul. 22, 2022, in 57 pages.

Interim Procedure for Discretionary Denials in AIA Post-Grant Proceedings with Parallel District Court Litigation, issued Jun. 21, 2022 ("Interim Guidance").

Declaration of Brian W. Anthony, Ph.D., Ex. 1003, *Apple Inc.* v. *Masimo Corporation,* Inter Partes Review No. IPR2022-01291 and IPR2022-01292, dated Jul. 22, 2022, in 77 pages.

Petitioner's Notice of Ranking of Petitions of U.S. Pat. No. 10,687,745, *Apple Inc.* v. *Masimo Corporation,* Inter Partes Review No. IPR2022-01291, dated Jul. 22, 2022, in 7 pages.

Patent Owner Preliminary Response of U.S. Pat. No. 10,687,745, *Apple Inc.* v. *Masimo Corporation,* Inter Partes Review No. IPR2022-01291, dated Nov. 4, 2022, in 73 pages.

Patent Owner Response to Petitioner's Notices Ranking of Petition of U.S. Pat. No. 10,687,745, *Apple Inc.* v. *Masimo Corporation,* Inter Partes Review No. IPR2022-01291, dated Nov. 4, 2022, in 8 pages.

Corrected Petition for Inter Partes Review of U.S. Pat. No. 10,687,745, *Apple Inc.* v. *Masimo Corporation,* Inter Partes Review No. IPR2022-01291, dated Oct. 7, 2022, in 57 pages.

*Masimo Corp et al.* v. *Apple Inc.,* Jun. 6-10, 2022 Public Hearing Transcript, ITC Inv. No 337-TA-1276, in Inter Partes Review of U.S. Pat. No. 10,687,745, Ex. 2008, *Apple Inc.* v. *Masimo Corporation,* Inter Partes Review Nos. IPR2020-01291, IPR2022-01292, dated Jun. 6, 2022, in 670 pages. [uploaded in 2 parts].

Jan. 3, 2013 Masimo Press Release Regarding iSpO2, in Inter Partes Review of U.S. Pat. No. 10,687,745, Ex. 2020, *Apple Inc.* v. *Masimo Corporation,* Inter Partes Review Nos. IPR2020-01291, IPR2022-01292, in 3 pages.

Excerpts of Webster's New Collegiate Dictionary (1980), in Inter Partes Review of U.S. Pat. No. 10,687,745, Ex. 2065, *Apple Inc.* v. *Masimo Corporation,* Inter Partes Review Nos. IPR2020-01291, IPR2022-01292, in 5 pages.

Masimo 2014 Annual Report, in Inter Partes Review of U.S. Pat. No. 10,687,745, Ex. 2066, *Apple Inc.* v. *Masimo Corporation,* Inter Partes Review Nos. IPR2020-01291, IPR2022-01292, in 80 pages.

Petitioner Updated Mandatory Notice of U.S. Pat. No. 10,687,745, *Apple Inc.* v. *Masimo Corporation,* Inter Partes Review No. IPR2022-01291, dated Dec. 21, 2022, in 4 pages.

Masimo Updated Mandatory Notices of U.S. Pat. No. 10,687,745, *Apple Inc.* v. *Masimo Corporation,* Inter Partes Review No. IPR2022-01291, dated Dec. 29, 2022, in 5 pages.

Decision Granting Institution of Inter Partes Review of U.S. Pat. No. 10,687,745, *Apple Inc.* v. *Masimo Corporation,* Inter Partes Review No. IPR2022-01291, dated Feb. 1, 2023, in 27 pages.

Petitioners Updated Exhibit List of U.S. Pat. No. 10,687,745, *Apple Inc.* v. *Masimo Corporation,* Inter Partes Review No. IPR2022-01291, dated Feb. 16, 2023, in 5 pages.

Patent Owners Motion for Additional Discovery of U.S. Pat. No. 10,687,745, *Apple Inc.* v. *Masimo Corporation,* Inter Partes Review No. IPR2022-01291, dated Feb. 24, 2023, in 23 pages.

Petitioners Opposition to Patent Owners Motion for Additional Discovery of U.S. Pat. No. 10,687,745, *Apple Inc.* v. *Masimo Corporation,* Inter Partes Review No. IPR2022-01291, dated Mar. 3, 2023, in 21 pages.

Patent Owner Corrected Updated Exhibit List of U.S. Pat. No. 10,687,745, *Apple Inc.* v. *Masimo Corporation,* Inter Partes Review No. IPR2022-01291, dated Jun. 16, 2023, in 8 pages.

Patent Owner Updated Exhibit List of U.S. Pat. No. 10,687,745, *Apple Inc.* v. *Masimo Corporation,* Inter Partes Review No. IPR2022-01291, dated Jun. 16, 2023, in 8 pages.

Petitioner's Reply to Patent Owner's Response of U.S. Pat. No. 10,687,745, *Apple Inc.* v. *Masimo Corporation,* Inter Partes Review No. IPR2022-01291, dated Aug. 21, 2023, in 39 pages.

(56)                    References Cited

OTHER PUBLICATIONS

Telephonic Hearing Transcript before the Panel for Inter Partes Review of U.S. Pat. No. 10,687,745, Ex. 2096, *Apple Inc.* v. *Masimo Corporation,* Inter Partes Review Nos. IPR2022-01291, IPR2022-01465, dated Sep. 1, 2023 in 70 pages.

Declaration of Anne Koch Baland, *Apple Inc.* v. *Masimo Corporation,* Inter Partes Review No. IPR2022-01291, Sep. 12, 2023, in 492 pages. [Uploaded in 2 parts].

Patent Owner Updated Exhibit List of U.S. Pat. No. 10,687,745, *Apple Inc.* v. *Masimo Corporation,* Inter Partes Review No. IPR2022-01291, dated Sep. 13, 2023, in 9 pages.

Patent Owner Request for Oral Argument of U.S. Pat. No. 10,687,745, *Apple Inc.* v. *Masimo Corporation,* Inter Partes Review No. IPR2022-01291, dated Sep. 22, 2023, in 5 pages.

Petitioner's Request for Oral Argument of U.S. Pat. No. 10,687,745, *Apple Inc.* v. *Masimo Corporation,* Inter Partes Review No. IPR2022-01291, dated Sep. 22, 2023, in 4 pages.

Patent Owner Sur-Reply of U.S. Pat. No. 10,687,745, *Apple Inc.* v. *Masimo Corporation,* Inter Partes Review No. IPR2022-01291, filed Oct. 2, 2023, in 46 pages.

Redacted Declaration of R. James Duckworth in Support of Patent Owner's Sur-Reply, U.S. Pat. No. 10,687,745, *Apple Inc.* v. *Masimo Corporation,* Inter Partes Review Nos. IPR2022-01291, IPR2022-01465, dated Oct. 2, 2023, in 85 pages.

Second Corrected Petition for Inter Partes Review of U.S. Pat. No. 10,687,745, *Apple Inc.* v. *Masimo Corporation,* Inter Partes Review No. IPR2022-01291, dated Oct. 4, 2023, in 57 pages.

Transcript of Deposition of James Duckworth, Ph.D. in Inter Partes Review of U.S. Pat. No. 10,687,745, Ex. 1081, *Apple Inc.* v. *Masimo Corporation,* Inter Partes Review No. IPR2022-01291 and IPR2022-01465, dated Oct. 18, 2023, in 116 pages.

Oct. 26, 2023 Notice of the Commission's Final Determination Finding a Violation of Section 337; Issuance of a Limited Exclusion Order and a Cease and Desist Order; Termination Of The Investigation, Inv. No 337-TA-1276, pp. 4.

Petitioner's Response to Expert Testimony Proffered with Patent Owner's Sur-Reply, *Apple Inc.* v. *Masimo Corporation,* Inter Partes Review No. IPR2022-01291, dated Oct. 27, 2023, in 19 pages.

Patent Owner Updated Exhibit List, *Apple Inc.* v. *Masimo Corporation,* Inter Partes Review No. IPR2022-01291, dated Nov. 14, 2023, in 9 pages.

Patent Owner Updated Exhibit List, *Apple Inc.* v. *Masimo Corporation,* Inter Partes Review No. IPR2022-01291, dated Nov. 15, 2023, in 9 pages.

Petitioner's Updated List of Exhibits, *Apple Inc.* v. *Masimo Corporation,* Inter Partes Review No. IPR2022-01291, dated Nov. 15, 2023, in 9 pages.

Redacted Apple (Petitioner) Demonstratives for Oral Argument, Inter Partes Review No. IPR2022-01291 and IPR2022-01465, filed Nov. 15, 2023, in 106 pages.

Redacted Patent Owner Masimo's Trial Hearing Demonstratives, Inter Partes Review No. IPR2022-01291 and IPR2022-01465, filed Nov. 15, 2023, in 95 pages.

Hearing Transcript, *Apple Inc.* v. *Masimo Corporation,* Inter Partes Review No. IPR2022-01291 and IPR2022-01465, held Nov. 17, 2023, and entered Dec. 13, 2023, in 87 pages.

Judgment, Final Written Decision, *Apple Inc.* v. *Masimo Corporation,* Inter Partes Review No. IPR2022-01291, dated Jan. 30, 2024, in 145 pages.

Petition for Inter Partes Review of U.S. Pat. No. 10,687,745, *Apple Inc.* v. *Masimo Corporation,* Inter Partes Review No. IPR2022-01292, dated Jul. 22, 2022, in 88 pages.

Petitioner's Notice of Ranking of Petitions of U.S. Pat. No. 10,687,745, *Apple Inc.* v. *Masimo Corporation,* Inter Partes Review No. IPR2022-01292, dated Jul. 22, 2022, in 7 pages.

Patent Owner Preliminary Response of U.S. Pat. No. 10,687,745, *Apple Inc.* v. *Masimo Corporation,* Inter Partes Review No. IPR2022-01292, dated Nov. 4, 2022, in 67 pages.

Corrected Petition for Inter Partes Review of U.S. Pat. No. 10,687,745, *Apple Inc.* v. *Masimo Corporation,* Inter Partes Review No. IPR2022-01292, dated Oct. 7, 2022, in 88 pages.

Patent Owner Response to Petitioner's Notices Ranking Petition of U.S. Pat. No. 10,687,745, *Apple Inc.* v. *Masimo Corporation,* Inter Partes Review No. IPR2022-01292, dated Nov. 4, 2022, in 8 pages.

Declaration of R. James Duckworth, Ph.D, in Inter Partes Review of U.S. Pat. No. 10,687,745, Ex. 2002, *Apple Inc.* v. *Masimo Corporation,* Inter Partes Review Nos. IPR2020-01291, IPR2022-01292, dated Nov. 4, 2022, in 127 pages.

Curriculum Vitae of R. James Duckworth, Ph.D, in Inter Partes Review of U.S. Pat. No. 10,687,745, Ex. 2003, *Apple Inc.* v. *Masimo Corporation,* Inter Partes Review Nos. IPR2020-01291, IPR2022-01292, in 11 pages.

Petitioner Updated Mandatory Notice of U.S. Pat. No. 10,687,745, *Apple Inc.* v. *Masimo Corporation,* Inter Partes Review No. IPR2022-01292, dated Dec. 21, 2022, in 4 pages.

Masimo Updated Mandatory Notices of U.S. Pat. No. 10,687,745, *Apple Inc.* v. *Masimo Corporation,* Inter Partes Review No. IPR2022-01292, dated Dec. 29, 2022, in 5 pages.

Decision Denying Institution of Inter Partes Review of U.S. Pat. No. 10,687,745, *Apple Inc.* v. *Masimo Corporation,* Inter Partes Review No. IPR2022-01292, dated Feb. 1, 2023, in 12 pages.

Petition for Inter Partes Review of U.S. Pat. No. 10,687,745, *Apple Inc.* v. *Masimo Corporation,* Inter Partes Review No. IPR2022-01465, dated Aug. 26, 2022, in 93 pages.

Petitioner's Notice of Ranking of Petitions of U.S. Pat. No. 10,687,745, *Apple Inc.* v. *Masimo Corporation,* Inter Partes Review No. IPR2022-01465, dated Aug. 26, 2022, in 7 pages.

Corrected Petition for Inter Partes Review of U.S. Pat. No. 10,687,745, *Apple Inc.* v. *Masimo Corporation,* Inter Partes Review No. IPR2022-01465, dated Oct. 7, 2022, in 93 pages.

Masimo Preliminary Response of U.S. Pat. No. 10,687,745, *Apple Inc.* v. *Masimo Corporation,* Inter Partes Review No. IPR2022-01465, dated Dec. 13, 2022, in 77 pages.

Masimo Response to Apples Notice Ranking Petitions of U.S. Pat. No. 10,687,745, *Apple Inc.* v. *Masimo Corporation,* Inter Partes Review No. IPR2022-01465, dated Dec. 13, 2022, in 8 pages.

Petitioner Updated Mandatory Notice of U.S. Pat. No. 10,687,745, *Apple Inc.* v. *Masimo Corporation,* Inter Partes Review No. IPR2022-01465, dated Dec. 21, 2022, in 4 pages.

Masimo Updated Mandatory Notices of U.S. Pat. No. 10,687,745, *Apple Inc.* v. *Masimo Corporation,* Inter Partes Review No. IPR2022-01465, dated Dec. 29, 2022, in 5 pages.

Decision Granting Institution of Inter Partes Review of U.S. Pat. No. 10,687,745, *Apple Inc.* v. *Masimo Corporation,* Inter Partes Review No. IPR2022-01465, dated Feb. 6, 2023, in 32 pages.

Petitioners Updated Exhibit List of U.S. Pat. No. 10,687,745, *Apple Inc.* v. *Masimo Corporation,* Inter Partes Review No. IPR2022-01465, dated Feb. 16, 2023, in 5 pages.

Patent Owners Motion for Additional Discovery of U.S. Pat. No. 10,687,745, *Apple Inc.* v. *Masimo Corporation,* Inter Partes Review No. IPR2022-01465, dated Feb. 24, 2023, in 23 pages.

Petitioners Opposition to Patent Owners Motion for Additional Discovery of U.S. Pat. No. 10,687,745, *Apple Inc.* v. *Masimo Corporation,* Inter Partes Review No. IPR2022-01465, dated Mar. 3, 2023, in 21 pages.

Patent Owner Corrected Updated Exhibit List of U.S. Pat. No. 10,687,745, *Apple Inc.* v. *Masimo Corporation,* Inter Partes Review No. IPR2022-01465, dated Jun. 16, 2023, in 9 pages.

Patent Owner Request for Oral Argument of U.S. Pat. No. 10,687,745, *Apple Inc.* v. *Masimo Corporation,* Inter Partes Review No. IPR2022-01465, dated Sep. 22, 2023, in 5 pages.

Patent Owner Updated Exhibit List of U.S. Pat. No. 10,687,745, *Apple Inc.* v. *Masimo Corporation,* Inter Partes Review No. IPR2022-01465, dated Sep. 13, 2023, in 9 pages.

Patent Owner Updated Exhibit List of U.S. Pat. No. 10,687,745, *Apple Inc.* v. *Masimo Corporation,* Inter Partes Review No. IPR2022-01465, dated Jun. 16, 2023, in 9 pages.

Petitioner's Reply to Patent Owner's Response of U.S. Pat. No. 10,687,745, *Apple Inc.* v. *Masimo Corporation,* Inter Partes Review No. IPR2022-01465, dated Aug. 21, 2023, in 41 pages.

(56) References Cited

OTHER PUBLICATIONS

Petitioner's Request for Oral Argument of U.S. Pat. No. 10,687,745, *Apple Inc.* v. *Masimo Corporation*, Inter Partes Review No. IPR2022-01465, dated Sep. 22, 2023, in 4 pages.

Patent Owner Sur-Reply of U.S. Pat. No. 10,687,745, *Apple Inc.* v. *Masimo Corporation*, Inter Partes Review No. IPR2022-01465, filed Oct. 2, 2023, in 46 pages.

Petitioner's Response to Expert Testimony Proffered with Patent Owner's Sur-Reply, *Apple Inc.* v. *Masimo Corporation*, Inter Partes Review No. IPR2022-01465, dated Oct. 27, 2023, in 19 pages.

Patent Owner Updated Exhibit List, *Apple Inc.* v. *Masimo Corporation*, Inter Partes Review No. IPR2022-01465, dated Nov. 14, 2023, in 10 pages.

Patent Owner Updated Exhibit List, *Apple Inc.* v. *Masimo Corporation*, Inter Partes Review No. IPR2022-01465, dated Nov. 15, 2023, in 10 pages.

Petitioner's Updated List of Exhibits, *Apple Inc.* v. *Masimo Corporation*, Inter Partes Review No. IPR2022-01465, dated Nov. 15, 2023, in 9 pages.

Petition for Inter Partes Review of U.S. Pat. No. 10,687,745, *Apple Inc.* v. *Masimo Corporation*, Inter Partes Review No. IPR2022-01466, dated Aug. 26, 2022, in 79 pages.

Petitioner's Notice of Ranking of Petitions of U.S. Pat. No. 10,687,745, *Apple Inc.* v. *Masimo Corporation*, Inter Partes Review No. IPR2022-01466, dated Aug. 26, 2022, in 7 pages.

Corrected Petition for Inter Partes Review of U.S. Pat. No. 10,687,745, *Apple Inc.* v. *Masimo Corporation*, Inter Partes Review No. IPR2022-01466, dated Oct. 7, 2022, in 79 pages.

Petition for Inter Partes Review of U.S. Pat. No. 10,687,743, *Apple Inc.* v. *Masimo Corporation*, Inter Partes Review No. IPR2024-00241, dated Dec. 12, 2023, in 109 pages.

Stipulation by Apple dated Dec. 12, 2023, *Apple Inc.* v. *Masimo Corp., et al.*, Case. No. 1-22-cv-01378, signed by David Shaw in 4 pages.

Petitioner's Notice Ranking and Explaining Material Differences Between Petitions for Inter Partes Review of U.S. Pat. No. 10,687,743, *Apple Inc.* v. *Masimo Corporation*, Inter Partes Review No. IPR2024-00241, dated Dec. 12, 2023, in 8 pages.

Declaration of Brian W. Anthony, Ph.D., in support of Petition for Inter Partes Review of U.S. Pat. No. 10,687,743, Ex. 1003, *Apple Inc.* v. *Masimo Corporation*, Inter Partes Review No. IPR2024-00241, dated Dec. 9, 2023, in 108 pages.

Patent Owner Submission of Mandatory Notice of Information, *Apple Inc.* v. *Masimo Corporation*, Inter Partes Review No. IPR2024-00241, dated Jan. 2, 2024, in 6 pages.

Petition for Inter Partes Review of U.S. Pat. No. 10,687,743, *Apple Inc.* v. *Masimo Corporation*, Inter Partes Review No. IPR2024-00242, dated Dec. 12, 2023, in 99 pages.

Petitioner's Notice Ranking and Explaining Material Differences Between Petitions for Inter Partes Review of U.S. Pat. No. 10,687,743, *Apple Inc.* v. *Masimo Corporation*, Inter Partes Review No. IPR2024-00242, dated Dec. 12, 2023, in 8 pages.

Declaration of Brian W. Anthony, Ph.D., in support of Petition for Inter Partes Review of U.S. Pat. No. 10,687,743, Ex. 1003, *Apple Inc.* v. *Masimo Corporation*, Inter Partes Review No. IPR2024-00242, dated Dec. 9, 2023, in 103 pages.

Patent Owner Submission of Mandatory Notice of Information, *Apple Inc.* v. *Masimo Corporation*, Inter Partes Review No. IPR2024-00242, dated Jan. 2, 2024, in 6 pages.

Petition for Inter Partes Review of U.S. Pat. No. 10,722,159, *Apple Inc.* v. *Masimo Corporation*, Inter Partes Review No. IPR2024-00243, dated Dec. 12, 2023, in 105 pages.

Petitioner's Notice Ranking and Explaining Material Differences Between Petitions for Inter Partes Review of U.S. Pat. No. 10,722,159, *Apple Inc.* v. *Masimo Corporation*, Inter Partes Review No. IPR2024-00243, dated Dec. 12, 2023, in 8 pages.

Stipulation by Apple dated Dec. 12, 2023, *Apple Inc.* v. *Masimo Corp., et al.*, Case. No. 1-22-cv-01378, signed by David Shaw in 5 pages.

Declaration of Brian W. Anthony, Ph.D., in support of Petition for Inter Partes Review of U.S. Pat. No. 10,722,159, Ex. 1003, *Apple Inc.* v. *Masimo Corporation*, Inter Partes Review No. IPR2024-00243, dated Nov. 30, 2023, in 175 pages.

Patent Owner Submission of Mandatory Notice of Information, *Apple Inc.* v. *Masimo Corporation*, Inter Partes Review No. IPR2024-00243, dated Jan. 2, 2024, in 6 pages.

Petition for Inter Partes Review of U.S. Pat. No. 10,722,159, *Apple Inc.* v. *Masimo Corporation*, Inter Partes Review No. IPR2024-00244, dated Dec. 12, 2023, in 102 pages.

Petitioner's Notice Ranking and Explaining Material Differences Between Petitions for Inter Partes Review of U.S. Pat. No. 10,722,159, *Apple Inc.* v. *Masimo Corporation*, Inter Partes Review No. IPR2024-00244, dated Dec. 12, 2023, in 8 pages.

Declaration of Brian W. Anthony, Ph.D., in support of Petition for Inter Partes Review of U.S. Pat. No. 10,722,159, Ex. 1003, *Apple Inc.* v. *Masimo Corporation*, Inter Partes Review No. IPR2024-00244, dated Nov. 30, 2023, in 164 pages.

Patent Owner Submission of Mandatory Notice of Information, *Apple Inc.* v. *Masimo Corporation*, Inter Partes Review No. IPR2024-00244, dated Jan. 2, 2024, in 6 pages.

Corrected Non-Confidential Brief for Appellee Apple Inc., Appeals from the United States Patent Office, Patent Trial and Appeal Board Case Nos. IPR2022-01291 and IPR2022-01465, Federal Circuit Case Nos. 2024-1635, -1636, *Masimo Corporation* v. *Apple Inc.*, Jan. 10, 2025, in 77 pages.

Non-Confidential Joint Appendix, vol. I of V, Appeals from the United States Patent Office, Patent Trial and Appeal Board Case Nos. IPR2022-01291 and IPR2022-01465, Federal Circuit Case Nos. 2024-1635, -1636, *Masimo Corporation* v. *Apple Inc.*, Jan. 10, 2025, in 369 pages.

Non-Confidential Joint Appendix, vol. II of V, Appeals from the United States Patent Office, Patent Trial and Appeal Board Case Nos. IPR2022-01291 and IPR2022-01465, Federal Circuit Case Nos. 2024-1635, -1636, *Masimo Corporation* v. *Apple Inc.*, Jan. 10, 2025, in 371 pages.

Non-Confidential Joint Appendix, vol. III of V, Appeals from the United States Patent Office, Patent Trial and Appeal Board Case Nos. IPR2022-01291 and IPR2022-01465, Federal Circuit Case Nos. 2024-1635, -1636, *Masimo Corporation* v. *Apple Inc.*, Jan. 10, 2025, in 369 pages.

Non-Confidential Joint Appendix, vol. IV of V, Appeals from the United States Patent Office, Patent Trial and Appeal Board Case Nos. IPR2022-01291 and IPR2022-01465, Federal Circuit Case Nos. 2024-1635, -1636, *Masimo Corporation* v. *Apple Inc.*, Jan. 10, 2025, in 374 pages.

Non-Confidential Joint Appendix, vol. V of V, Appeals from the United States Patent Office, Patent Trial and Appeal Board Case Nos. IPR2022-01291 and IPR2022-01465, Federal Circuit Case Nos. 2024-1635, -1636, *Masimo Corporation* v. *Apple Inc.*, Jan. 10, 2025, in 275 pages.

Cleveland et al., "Resin" definition, Dictionary of Energy (Expanded Edition), Elsevier, Retrieved from https://app.knovel.com/hotlink/toc/id:kpDEEE0001/dictionary-energy-expanded/dictionary-energy-expanded, 2009, p. 433, 3 pages total.

Dec. 11, 2024 Plaintiff and Counterclaim-Defendant Apple Inc.'s Motion for Injunctive Relief, *Apple Inc.* v. *Masimo Corporation and Sound United, LLC*, Case No. 1:22-cv-01377-JLH, 2 pages.

Dec. 11, 2024 Plaintiff and Counterclaim-Defendant Apple Inc.'s Motion to Correct Clerical Mistakes or, in the Alternative, to Alter or Amend the Judgement, *Apple Inc.* v. *Masimo Corporation and Sound United, LLC*, Case No. 1:22-cv-01377-JLH, 3 pages.

Dec. 11, 2024 Corrected Judgement Following Jury Verdict, *Apple Inc.* v. *Masimo Corporation and Sound United, LLC*, Case No. 1:22-cv-01377-JLH, 4 pages.

Dec. 11, 2024 Masimo's Motion for Judgement as a Matter of Law, *Apple Inc.* v. *Masimo Corporation and Sound United, LLC*, Case No. 1:22-cv-01377-JLH, 7 pages.

Dec. 13, 2024 Defendants' Opening Brief in Support of Motion for Judgment as a Matter of Law, *Apple Inc.* v. *Masimo Corporation and Sound United, LLC*, Case No. 1:22-cv-01377-JLH, 21 pages.

Jan. 10, 2025 Apple's Opening Brief in Support of: (I) Its Motion for a Permanent Injunction (35 U.S.C. § 283) [-1377 Case], (II) Its

(56) References Cited

OTHER PUBLICATIONS

Motions to Amend and/or Correct the Judgments (Fed. R. Civ.P. 52(b), 59(e), 60) [-1377 Case], (III) Its Motion for Judgment as a Matter of Law (Fed. R. Civ. P. 50(b)) [-1378 Case], (IV) Its Motion in the Alternative for a New Trial (Fed. R Civ. P. 59(a)) [-1378 CASE], Public Version, *Apple Inc.* v. *Masimo Corporation and Sound United, LLC*, Case No. 1:22-cv-01377-JLH, 33 pages.

Jan. 10, 2025 Declaration of Lee J. Matalon in Support of Apple's Post-Trial Motions, Including Exhibits 76-94, Public Version, *Apple Inc.* v. *Masimo Corporation and Sound United, LLC*, Case No. 1:22-cv-01377-JLH, 147 pages.

Jan. 10, 2025 Letter to the Honorable Jennifer L. Hall from David E. Moore, Public Version, *Apple Inc.* v. *Masimo Corporation and Sound United, LLC*, Case No. 1:22-cv-01377-JLH, 11 pages.

Jan. 10, 2025 Letter to the Honorable Jennifer L. Hall from John C. Phillips, Jr., Redacted—Public Version, *Apple Inc.* v. *Masimo Corporation and Sound United, LLC*, Case No. 1:22-cv-01377-JLH, 90 pages.

Jan. 31, 2025 Apple's Brief Opposing Defendant's Motion for Judgment as a Matter of Law, Public Version, *Apple Inc.* v. *Masimo Corporation and Sound United, LLC*, Case No. 1:22-cv-01377-JLH, 32 pages.

Jan. 31, 2025 Declaration of Kendall M. Loebbaka in Support of Masimo's Answering Brief in Opposition to (I) Apple's Motion for a Permanent Injunction, and (II) Apple's Motion to Amend and/or Correct the Judgment, Including Exhibit A, Redacted—Public Version, *Apple Inc.* v. *Masimo Corporation and Sound United, LLC*, Case No. 1:22-cv-01377-JLH, 18 pages.

Jan. 31, 2025 Masimo's Answering Brief in Opposition to (I) Apple's Motion for a Permanent Injunction, and (II) Apple's Motion to Amend and/or Correct the Judgment, Redacted—Public Version, *Apple Inc.* v. *Masimo Corporation and Sound United, LLC*, Case No. 1:22-cv-01377-JLH, 18 pages.

Jan. 31, 2025 Declaration of Bilal Muhsin, Redacted—Public Version, *Apple Inc.* v. *Masimo Corporation and Sound United, LLC*, Case No. 1:22-cv-01377-JLH, 2 pages.

Feb. 21, 2025 Declaration of Kendall M. Loebbaka in Support of Defendants' Reply Brief in Support of Motion for Judgment as a Matter of Law, Including Exhibits O and P, *Apple Inc.* v. *Masimo Corporation and Sound United, LLC*, Case No. 1:22-cv-01377-JLH, 62 pages.

Feb. 21, 2025 Defendants' Reply Brief in Support of Motion for Judgment as a Matter of Law, *Apple Inc.* v. *Masimo Corporation and Sound United, LLC*, Case No. 1:22-cv-01377-JLH, 16 pages.

Dec. 2, 2024 Joint Notice Regarding Judgements Following Jury Verdict, Including Exhibits 1 & 2, *Apple Inc.* v. *Masimo Corporation and Sound United, LLC*, *Masimo Corporation and Sound United. LLC.* v. *Apple Inc.*, Case No. 1:22-cv-01378-JLH, 12 pages.

Dec. 11, 2024 Plaintiff and Counterclaim-Defendant Apple Inc.'s Motion for Judgment as a Matter of Law or, in the Alternative, for a New Trial, *Apple Inc.* v. *Masimo Corporation and Sound United, LLC*, *Masimo Corporation and Sound United. LLC.* v. *Apple Inc.*, Case No. 1:22-cv-01378-JLH, 2 pages.

Dec. 11, 2024 Corrected Judgement Following Jury Verdict, *Apple Inc.* v. *Masimo Corporation and Sound United, LLC*, *Masimo Corporation and Sound United. LLC.* v. *Apple Inc.*, Case No. 1:22-cv-01378-JLH, 4 pages.

Jan. 31, 2025 Declaration of Kendall M. Loebbaka in Support of Masimo's Answering Brief in Opposition to Apple Inc.'s Motion for Judgment as a Matter of Law or, in the Alternative, for a New Trial, Including Exhibit B & C, Redacted—Public Version, *Apple Inc.* v. *Masimo Corporation and Sound United, LLC*, Case No. 1:22-cv-01378-JLH, 20 pages.

Jan. 31, 2025 Masimo's Answering Brief in Opposition to (III) Apple's Motion for Judgment as a Matter of Law and (IV) Apple's Motion in the Alternative for a New Trial, Redacted—Public Version, *Apple Inc.* v. *Masimo Corporation and Sound United, LLC*, Case No. 1:22-cv-01378-JLH, 26 pages.

Feb. 28, 2025 Declaration of Lee J. Matalon in Support of Apple's Reply Brief in Support of its Post-Trial Motions, Including Exhibits 95-105, Public Version, *Apple Inc.* v. *Masimo Corporation and Sound United, LLC*, Case No. 1:22-cv-01378-JLH, 48 pages.

Feb. 28, 2025 Apple's Reply Brief In Support Of: (I) Its Motion for a Permanent Injunction (35 U.S.C. § 283) [-1377 Case], (II) Its Motions to Amend and/or Correct the Judgment (Fed. R. Civ. P. 52(b), 59(e), 60) [-1377 Case], (III) Its Motion for Judgment as a Matter Of Law (Fed. R. Civ. P. 50(b)) [-1378 Case], (IV) Its Motion in The Alternative for a New Trial (Fed. R. Civ. P. 59(a)) [-1378 Case], Public Version, *Apple Inc.* v. *Masimo Corporation and Sound United, LLC*, Case No. 1:22-cv-01378-JLH, 16 pages.

Ertin et al., "AutoSense: Unobtrusively Wearable Sensor Suite for Inferring the Onset, Causality, and Consequences of Stress in the Field", SenSys'11, Nov. 1-4, 2011, pp. 14.

U.S. Appl. No. 61/886,930 ("Lee Provisional"), filed Oct. 4, 2013 in 22 pages.

Chiu et al., "Discrete Wavelet Transform Applied on Personal Identity Verification with ECG Signal", Research Gate, Conference Paper, May 2008, pp. 20.

Dictionary.com, Definition of "enclosure", printed Jun. 14, 2024, https://www.dictionary.com/browse/enclosure, pp. 5.

Kyoso et al., "Development of an ECG Identification System", 2001 Proceedings of the 23rd Annual EMBS Internation Conference, Oct. 25-28, 2001, Istanbul, Turkey, pp. 3721-3723.

Merriam-Webster, Definition of "enclosure", printed Jun. 14, 2024, https://www.merriam-webster.com/dictionary/enclosure#:~:text=1,%3A%20something%20that%20encloses, pp. 10.

Singh et al., "ECG to Individual Identification", Research Gate, Conference Paper, Nov. 2008, pp. 9.

The American Heritage Dictionary of the English Language, Definition of "enclosure", printed Jun. 14, 2024, https://ahdictionary.com/word/search.html?q=enclosure, pp. 3.

Wübbeler et al., "Verification of humans using the electrocardiogram", Science Direct, Pattern Recognition Letters, vol. 28, 2007, pp. 1172-1175.

Dec. 12, 2022 Defendant Masimo Corporation's Answer to Complaint and Counterclaims, *Apple Inc.* v. *Masimo Corporation and Sound United, LLC*, Case No. 1:22-cv-01377-MN, 39 pages.

Jun. 8, 2023 Masimo Corporation and Sound United, LLC. Initial Design Patent Invalidity Contentions, *Apple Inc.* v. *Masimo Corporation and Sound United, LLC*, *Masimo Corporation* v. *Apple Inc.*, Case No. 1:22-cv-01377-MN, 211 pages.

Jun. 22, 2023 Plaintiff Apple Inc.'s Initial Response to Design Patent Invalidity Contentions, *Apple Inc.* v. *Masimo Corporation and Sound United, LLC*, *Masimo Corporation* v. *Apple Inc.*, Case No. 1:22-cv-01377-MN, 225 pages.

Jun. 23, 2023 Defendant Masimo Corporation's Answer to Complaint and First Amended Counterclaims, *Apple Inc.* v. *Masimo Corporation and Sound United, LLC*, *Masimo Corporation* v. *Apple Inc.*, Case No. 1:22-cv-01377-MN, 48 pages.

Jul. 5, 2023 Defendant Sound United, LLC's Answer to Complaint and Counterclaims, *Apple Inc.* v. *Masimo Corporation and Sound United, LLC*, *Masimo Corporation* v. *Apple Inc.*, Case No. 1:22-cv-01377-MN, 45 pages.

Jul. 17, 2023 Masimo Corporation and Sound United, LLC's First Supplemental Design Patent Invalidity Contentions, *Apple Inc.* v. *Masimo Corporation and Sound United, LLC*, *Masimo Corporation* v. *Apple Inc.*, Case No. 1:22-cv-01377-MN, 160 pages.

Aug. 17, 2023 Masimo Corporation and Sound United, LLC's Final Identification of Invalidity References, *Apple Inc.* v. *Masimo Corporation and Sound United, LLC*, *Masimo Corporation* v. *Apple Inc.*, Case No. 1:22-cv-01377-MN, 8 pages.

Exhibits A-F (Final Identification of Invalidity References) submitted with Aug. 17, 2023 Masimo Corporation and Sound United, LLC's Final Identification of Invalidity References, *Apple Inc.* v. *Masimo Corporation and Sound United, LLC*, *Masimo Corporation* v. *Apple Inc.*, Case No. 1:22-cv-01377-MN, 41 pages.

Aug. 31, 2023 Joint Claim Construction Brief for Apple Asserted Patents, *Apple Inc.* v. *Masimo Corporation and Sound United, LLC*, *Masimo Corporation and Cercacor Laboratories, Inc.* v. *Apple Inc.*, Case No. 1:22-cv-01377-MN, 104 pages.

Feb. 10, 2023 Plaintiff Apple Inc.'s Opening Brief in Support of its Motion for an Expedited Trial, *Apple Inc.* v. *Masimo Corporation*

(56)                    References Cited

OTHER PUBLICATIONS

*and Sound United, LLC, Masimo Corporation and Cercacor Laboratories, Inc.* v. *Apple Inc.,* Case No. 1:22-cv-01377-MN, 29 pages.
Feb. 20, 2024 Apple's Motion to Strike Invalidity Opinions, Exhibits 1-31 ONLY, *Apple Inc.* v. *Masimo Corporation and Sound United, LLC, Masimo Corporation and Cercacor Laboratories, Inc.* v. *Apple Inc.,* Case No. 1:22-cv-01377-JLH, 688 pages.
Feb. 23, 2024 Letter to the Honorable Jennifer L. Hall from John C. Phillips, Jr., *Apple Inc.* v. *Masimo Corporation and Sound United, LLC, Masimo Corporation and Cercacor Laboratories, Inc.* v. *Apple Inc.,* Case No. 1:22-cv-01377-JLH, 297 pages.
Feb. 26, 2024 Milici Declaration in Support of Apple's Motions for Summary Judgement, Including Exhibits 1-50, *Apple Inc.* v. *Masimo Corporation and Sound United, LLC, Masimo Corporation and Cercacor Laboratories, Inc.* v. *Apple Inc.,* Case No. 1:22-cv-01377-JLH, 379 pages.
Mar. 11, 2024 Declaration of Kyle Curry in Support of Apple's Opposition to Masimo's Motion for Summary Judgment of Non-Infringement of Apple's Design Patents (Motion Rank No. 2), Including Exhibits A31-A33, A35-A37, A42-A43, A45-A46, A51, *Apple Inc.* v. *Masimo Corporation and Sound United, LLC, Masimo Corporation and Cercacor Laboratories, Inc.* v. *Apple Inc.,* Case No. 1:22-cv-01377-JLH, 406 pages.
Mar. 11, 2024 Declaration of Kyle Curry in Support of Apple's Opposition to Masimo's Motion for Summary Judgment that Certain Apple Design Patents are Invalid for Indefiniteness Under 35 U.S.C. § 112 (Motion Rank No. 3), Including Exhibits C17-26 & C28, *Apple Inc.* v. *Masimo Corporation and Sound United, LLC, Masimo Corporation and Cercacor Laboratories, Inc.* v. *Apple Inc.,* Case No. 1:22-cv-01377-JLH, 1091 pages. [Uploaded in 2 parts].
Mar. 11, 2024 Declaration of Lee Matalon in Support of Apple's Opposition to Masimo's Daubert Motions, Including Exhibits E34-E38, E44-48 & E52, *Apple Inc.* v. *Masimo Corporation and Sound United, LLC, Masimo Corporation and Cercacor Laboratories, Inc.* v. *Apple Inc.,* Case No. 1:22-cv-01377-JLH, 443 pages.
Mar. 11, 2024 Plaintiff and Counterclaim-Defendant Apple Inc.'s Brief in Opposition to Masimo's Motion for Summary Judgment of Non-Infringement of Apple's Design Patents (Motion Rank No. 2), *Apple Inc.* v. *Masimo Corporation and Sound United, LLC, Masimo Corporation and Cercacor Laboratories, Inc.* v. *Apple Inc.,* Case No. 1:22-cv-01377-JLH, 19 pages.
Mar. 11, 2024 Plaintiff and Counterclaim-Defendant Apple Inc.'s Brief in Opposition to Masimo's Motion for Summary Judgment that Certain Apple Design Patents are Invalid for Indefiniteness under 35 U.S.C. § 112 (Motion Rank No. 3), *Apple Inc.* v. *Masimo Corporation and Sound United, LLC, Masimo Corporation and Cercacor Laboratories, Inc.* v. *Apple Inc.,* Case No. 1:22-cv-01377-JLH, 16 pages.
Mar. 11, 2024 Plaintiff and Counterclaim-Defendant Apple Inc.'s Brief in Opposition to Masimo's Daubert Motions to Preclude Certain Testimony from Apple's Experts Malackowski, Matal, Ball, And Simonson, *Apple Inc.* v. *Masimo Corporation and Sound United, LLC, Masimo Corporation and Cercacor Laboratories, Inc.* v. *Apple Inc.,* Case No. 1:22-cv-01377-JLH, 24 pages.
Mar. 11, 2024 Plaintiff and Counterclaim-Defendant Apple Inc.'s Separate Concise Statement of Facts as to Which There is a Genuine Issue to be Tried in Opposition to Masimo's Motion for Summary Judgment of Non-Infringement of Apple's Design Patents (Motion Rank No. 2), *Apple Inc.* v. *Masimo Corporation and Sound United, LLC, Masimo Corporation and Cercacor Laboratories, Inc.* v. *Apple Inc.,* Case No. 1:22-cv-01377-JLH, 7 pages.
Mar. 11, 2024 Plaintiff and Counterclaim-Defendant Apple Inc.'s Separate Concise Statement of Facts as to Which There is a Genuine Issue to be Tried in Opposition to Masimo's Motion for Summary Judgment that Certain Apple Design Patents are Invalid for Indefiniteness under 35 U.S.C. § 112 (Motion Rank No. 3), *Apple Inc.* v. *Masimo Corporation and Sound United, LLC, Masimo Corporation and Cercacor Laboratories, Inc.* v. *Apple Inc.,* Case No. 1:22-cv-01377-JLH, 7 pages.

Mar. 12, 2024 Masimo's Reply Brief in Support of its Daubert Motion to Exclude Certain Testimony of Apple's Experts, *Apple Inc.* v. *Masimo Corporation and Sound United, LLC, Masimo Corporation and Cercacor Laboratories, Inc.* v. *Apple Inc.,* Case No. 1:22-cv-01377-JLH, 19 pages.
Mar. 12, 2024 Masimo's Reply Brief in Support of Masimo's Motion for Summary Judgment that it does not Infringe the Apple Design Patents (Motion Rank No. 2), *Apple Inc.* v. *Masimo Corporation and Sound United, LLC, Masimo Corporation and Cercacor Laboratories, Inc.* v. *Apple Inc.,* Case No. 1:22-cv-01377-JLH, 15 pages.
Mar. 12, 2024 Masimo's Reply Brief in Support of Masimo's Motion for Summary Judgment that Certain Apple Design Patents are Invalid for Indefiniteness Under 35 U.S.C. § 112 (Motion Rank No. 3), *Apple Inc.* v. *Masimo Corporation and Sound United, LLC, Masimo Corporation and Cercacor Laboratories, Inc.* v. *Apple Inc.,* Case No. 1:22-cv-01377-JLH, 14 pages.
Mar. 12, 2024 Masimo's Response to Apple's Concise Statement of Facts Regarding Masimo's Motion for Summary Judgment of Non-Infringement of Apple's Design Patents (Motion Rank No. 2), *Apple Inc.* v. *Masimo Corporation and Sound United, LLC, Masimo Corporation and Cercacor Laboratories, Inc.* v. *Apple Inc.,* Case No. 1:22-cv-01377-JLH, 10 pages.
Mar. 12, 2024 Masimo's Response to Apple's Concise Statement of Facts in Support of Apple's Opposition to Masimo's Motion for Summary Judgment that Certain Apple Design Patents are Invalid for Indefiniteness Under 35 U.S.C. § 112 (Motion Rank No. 3), *Apple Inc.* v. *Masimo Corporation and Sound United, LLC, Masimo Corporation and Cercacor Laboratories, Inc.* v. *Apple Inc.,* Case No. 1:22-cv-01377-JLH, 10 pages.
Mar. 12, 2024 Reply Declaration of Nicholas M. Zovko in Support of Masimo's Motion for Summary Judgment that Masimo Does Not Infringe the Apple Design Patents (Motion Rank No. 2), Including Exhibit A56, *Apple Inc.* v. *Masimo Corporation and Sound United, LLC, Masimo Corporation and Cercacor Laboratories, Inc.* v. *Apple Inc.,* Case No. 1:22-cv-01377-JLH, 9 pages.
Mar. 12, 2024 Reply Declaration of Nicholas M. Zovko in Support of Masimo's Motion for Summary Judgment that Certain Apple Design Patents are Invalid for Indefiniteness Under 35 U.S.C. § 112 (Motion Rank No. 3), *Apple Inc.* v. *Masimo Corporation and Sound United, LLC, Masimo Corporation and Cercacor Laboratories, Inc.* v. *Apple Inc.,* Case No. 1:22-cv-01377-JLH, 76 pages.
Mar. 13, 2024 Declaration of Daniel P. Hughes in Support of Masimo's Opposition to Apple's Motions for Summary Judgment, Motion to Exclude Dr. Steven Schwartz's Opinion, and Motion to Exclude Daniel McGavock's Lost Profits and Reasonable Royalty Opinions, Including Exhibits I-J, P-R, T, Ab-Ad, Cq-Cs, Cu, Cz, Da-Dg, Dr-Ds, *Apple Inc.* v. *Masimo Corporation and Sound United, LLC, Masimo Corporation and Cercacor Laboratories, Inc.* v. *Apple Inc.,* Case No. 1:22-cv-01377-JLH, 1266 pages. [Uploaded in 4 parts].
Mar. 13, 2024 Letter to the Honorable Jennifer L. Hall from John C. Phillips, Jr., Including Exhibits 7-9, 11 & 13, *Apple Inc.* v. *Masimo Corporation and Sound United, LLC, Masimo Corporation and Cercacor Laboratories, Inc.* v. *Apple Inc.,* Case No. 1:22-cv-01377-JLH, 97 pages.
Mar. 13, 2024 Masimo's Opposition to Apple's Omnibus Motion for Summary Judgment and Motion to Exclude Dr. Steven Schwartz's Opinion, *Apple Inc.* v. *Masimo Corporation and Sound United, LLC, Masimo Corporation and Cercacor Laboratories, Inc.* v. *Apple Inc.,* Case No. 1:22-cv-01377-JLH, 60 pages.
Mar. 13, 2024 Masimo's Response to Apple Inc.'s Concise Statement of Facts in Support of Motion for Summary Judgment of No Inequitable Conduct: Summary Judgment Motion No. 1, *Apple Inc.* v. *Masimo Corporation and Sound United, LLC, Masimo Corporation and Cercacor Laboratories, Inc.* v. *Apple Inc.,* Case No. 1:22-cv-01377-JLH, 15 pages.
Mar. 14, 2024 Ford Declaration in Support of Apple's Reply Brief in Support of its Motions for Summary Judgment, Including Exhibits 215-221, *Apple Inc.* v. *Masimo Corporation and Sound United, LLC, Masimo Corporation and Cercacor Laboratories, Inc.* v. *Apple Inc.,* Case No. 1:22-cv-01377-JLH, 114 pages.

(56) References Cited

OTHER PUBLICATIONS

Mar. 14, 2024 Plaintiff and Counterclaim-Defendant Apple Inc.'s Omnibus Reply Brief in Support of its Motions for Summary Judgment and to Exclude Dr. Steven Schwartz's Opinion, *Apple Inc. v. Masimo Corporation and Sound United, LLC, Masimo Corporation and Cercacor Laboratories, Inc. v. Apple Inc.*, Case No. 1:22-cv-01377-JLH, 32 pages.

Mar. 14, 2024 Plaintiff and Counterclaim-Defendant Apple Inc.'s Response to Masimo's Concise Statement of Facts in Support of its opposition to Apple's Motion for Summary Judgment Motion No. 1, *Apple Inc. v. Masimo Corporation and Sound United, LLC, Masimo Corporation and Cercacor Laboratories, Inc. v. Apple Inc.*, Case No. 1:22-cv-01377-JLH, 7 pages.

Mar. 14, 2024 Plaintiff and Counterclaim-Defendant Apple Inc.'s Response to Masimo's Concise Statement of Facts in Support of its Motion for Summary Judgment that Certain Apple Design Patents are Invalid for Indefiniteness Under 35 U.S.C. § 112 (Motion Rank No. 3), *Apple Inc. v. Masimo Corporation and Sound United, LLC, Masimo Corporation and Cercacor Laboratories, Inc. v. Apple Inc.*, Case No. 1:22-cv-01377-JLH, 4 pages.

Mar. 18, 2024 Letter to the Honorable Jennifer L. Hall from David E. Moore, Including Exhibits 16-51, *Apple Inc. v. Masimo Corporation and Sound United, LLC, Masimo Corporation and Cercacor Laboratories, Inc. v. Apple Inc.*, Case No. 1:22-cv-01377-JLH, 173 pages.

Jun. 26, 2024 Defendants Masimo Corporation and Sound United, LLC's Notice of Supplemental Authority Regarding (I) Non-Infringement and (II) Claim Construction, *Apple Inc. v. Masimo Corporation and Sound United, LLC*, Case No. 1:22-cv-01377-JLH, 14 pages.

Jul. 3, 2024 Apple Inc.'s Response to Masimo's Notice of Subsequent Authority, *Apple Inc. v. Masimo Corporation and Sound United, LLC, Masimo Corporation v. Apple Inc.*, Case No. 1:22-cv-01377-JLH, 4 pages.

Jun. 8, 2023 Defendant Masimo Corporation and Sound United, LLC. Initial Invalidity Contentions, *Apple Inc. v. Masimo Corporation and Sound United, LLC, Masimo Corporation and Cercacor Laboratories, Inc. v. Apple Inc.*, Case No. 1:22-cv-01378-MN, 1398 pages. [Uploaded in 3 parts].

Jun. 22, 2023 Plaintiff Apple Inc.'s Initial Response to Utility Patent Invalidity Contentions, *Apple Inc. v. Masimo Corporation and Sound United, LLC, Masimo Corporation and Cercacor Laboratories, Inc. v. Apple Inc.*, Case No. 1:22-cv-01378-MN, 280 pages.

Aug. 17, 2023 Masimo Corporation and Sound United, LLC's Final Identification of Invalidity References & Exhibits A-F, *Apple Inc. v. Masimo Corporation and Sound United, LLC, Masimo Corporation and Cercacor Laboratories, Inc. v. Apple Inc.*, Case No. 1:22-cv-01378-MN, 49 pages.

Aug. 31, 2023 Joint Claim Construction Brief for Apple Asserted Patents, *Apple Inc. v. Masimo Corporation and Sound United, LLC, Masimo Corporation and Cercacor Laboratories, Inc. v. Apple Inc.*, Case No. 1:22-cv-01378-MN, 104 pages.

Aug. 31, 2023 Joint Claim Construction Brief Regarding Masimo Asserted Patents, *Apple Inc. v. Masimo Corporation and Sound United, LLC, Masimo Corporation and Cercacor Laboratories, Inc. v. Apple Inc.*, Case No. 1:22-cv-01378-MN, 98 pages.

Sep. 14, 2023 Transcript of Markman Hearing, *Apple Inc. v. Masimo Corporation and Sound United, LLC, Masimo Corporation v. Apple Inc.*, Case No. 1:22-cv-01377-MN & Apple Inc. v. Masimo Corporation and Sound United, LLC, Masimo Corporation and Cercacor Laboratories, Inc. v. Apple Inc., Case No. 1:22-cv-01378-MN, 64 pages.

Jan. 10, 2024 Plaintiff Apple Inc.'s Opposition to Defendants' Motion for Stay Pending Inter Partes Review, *Apple Inc. v. Masimo Corporation and Sound United, LLC, Masimo Corporation and Cercacor Laboratories, Inc. v. Apple Inc.*, Case No. 1:22-cv-01378-MN, 20 pages.

Feb. 28, 2024 Masimo's Reply Brief in Support of Masimo's Motion for Summary Judgment that U.S. Pat. No. 11,106,352 is Invalid for Claiming Unpatentable Subject Matter Under 35 U.S.C. § 101 (Motion Rank No. 4), *Apple Inc. v. Masimo Corporation and Sound United, LLC, Masimo Corporation and Cercacor Laboratories, Inc. v. Apple Inc.*, Case No. 1:22-cv-01378-MN, 9 pages.

Feb. 28, 2024 Masimo's Reply Brief in Support of Masimo's Motion for Summary Judgment that U.S. Pat. No. 11,474,483 is Invalid for Obviousness Under 35 U.S.C. § 103 (Motion Rank No. 1), *Apple Inc. v. Masimo Corporation and Sound United, LLC, Masimo Corporation and Cercacor Laboratories, Inc. v. Apple Inc.*, Case No. 1:22-cv-01378-MN, 15 pages.

Feb. 28, 2024 Masimo's Response to Apple Inc.'s Concise Statement of Facts in Support of Masimo's Motion for Summary Judgment that U.S. Patent No. 11, 106,352 is Invalid for Claiming Unpatentable Subject Matter Under 35 U.S.C. § 101 (Motion Rank No. 4), *Apple Inc. v. Masimo Corporation and Sound United, LLC, Masimo Corporation and Cercacor Laboratories, Inc. v. Apple Inc.*, Case No. 1:22-cv-01378-MN, 4 pages.

Feb. 28, 2024 Masimo's Response to Apple Inc.'s Separate Concise Statement of Facts in Opposition to Masimo's Motion for Summary Judgment that U.S. Pat. No. 11,474,483 is Invalid for Obviousness Under 35 U.S.C. § 103 (Motion Rank No. 1), *Apple Inc. v. Masimo Corporation and Sound United, LLC, Masimo Corporation and Cercacor Laboratories, Inc. v. Apple Inc.*, Case No. 1:22-cv-01378-MN, 6 pages.

Mar. 11, 2024 Plaintiff and Counterclaim-Defendant Apple Inc.'s Brief in Opposition to Masimo's Motion for Summary Judgment that U.S. Patent No. 11, 106,352 is Invalid for Claiming Unpatentable Subject Matter Under 35 U.S.C. § 101 (Motion Rank No. 4), *Apple Inc. v. Masimo Corporation and Sound United, LLC, Masimo Corporation and Cercacor Laboratories, Inc. v. Apple Inc.*, Case No. 1:22-cv-01378-MN, 15 pages.

Mar. 11, 2024 Plaintiff and Counterclaim-Defendant Apple Inc.'s Brief in Opposition to Masimo's Motion for Summary Judgment that U.S. Pat. No. 11,474,483 is Invalid for Obviousness Under 35 U.S.C. § 103, *Apple Inc. v. Masimo Corporation and Sound United, LLC, Masimo Corporation and Cercacor Laboratories, Inc. v. Apple Inc.*, Case No. 1:22-cv-01378-MN, 21 pages.

Mar. 11, 2024 Plaintiff and Counterclaim-Defendant Apple Inc.'s Separate Concise Statement of Facts as to Which There is a Genuine Issue to be Tried in Opposition to Masimo's Motion for Summary Judgment that U.S. Pat. No. 11,106,352 is Invalid for Claiming Unpatentable Subject Matter Under 35 U.S.C. § 101 (Motion Rank No. 4), *Apple Inc. v. Masimo Corporation and Sound United, LLC, Masimo Corporation and Cercacor Laboratories, Inc. v. Apple Inc.*, Case No. 1:22-cv-01378-MN, 5 pages.

Mar. 11, 2024 Plaintiff and Counterclaim-Defendant Apple Inc.'s Separate Concise Statement of Facts as to Which There is a Genuine Issue to be Tried in Opposition to Masimo's Motion for Summary Judgment that U.S. Pat. No. 11,474,483 is Invalid for Obviousness Under 35 U.S.C. § 103 (Motion Rank No. 1), *Apple Inc. v. Masimo Corporation and Sound United, LLC, Masimo Corporation and Cercacor Laboratories, Inc. v. Apple Inc.*, Case No. 1:22-cv-01378-MN, 6 pages.

Mar. 11, 2024 Declaration of Carson Olsheski in Support of Apple's Opposition to Masimo's Motion for Summary Judgment that U.S. Pat. No. 11,106,352 is Invalid for Claiming Unpatentable Subject Matter, *Apple Inc. v. Masimo Corporation and Sound United, LLC, Masimo Corporation and Cercacor Laboratories, Inc. v. Apple Inc.*, Case No. 1:22-cv-01378-MN, 3 pages.

Mar. 11, 2024 Declaration of Carson Olsheski in Support of Apple's Opposition to Masimo's Motion or Summary Judgment that U.S. Pat. No. 11,474,483 is Invalid as Obvious (Motion Rank No. 1), *Apple Inc. v. Masimo Corporation and Sound United, LLC, Masimo Corporation and Cercacor Laboratories, Inc. v. Apple Inc.*, Case No. 1:22-cv-01378-MN, 534 pages. [Uploaded in 2 parts].

Mar. 13, 2024 Counter-Defendant Apple Inc.'s Final Invalidity Contentions, *Apple Inc. v. Masimo Corporation and Sound United, LLC, Masimo Corporation and Cercacor Laboratories, Inc. v. Apple Inc.*, Case No. 1:22-cv-01378-MN, 33 pages.

Mar. 14, 2024 Plaintiff and Counterclaim-Defendant Apple Inc.'s Response to Masimo's Concise Statement of Facts in Support of its Motion for Summary Judgment that U.S. Patent No. 11, 106,352 is Invalid for Claiming Unpatentable Subject Matter Under 35 U.S.C. § 101 (Motion Rank No. 4), *Apple Inc. v. Masimo Corporation and*

*(56)* References Cited

OTHER PUBLICATIONS

*Sound United, LLC, Masimo Corporation and Cercacor Laboratories, Inc.* v. *Apple Inc.*, Case No. 1:22-cv-01378-MN, 4 pages.
Mar. 14, 2024 Plaintiff and Counterclaim-Defendant Apple Inc.'s Response to Masimo's Concise Statement of Facts in Support of its motion for Summary Judgment that U.S. Pat. No. 11,474,483 is Invalid for Obviousness Under 35 U.S.C. § 103 (Motion Rank No. 1), *Apple Inc.* v. *Masimo Corporation and Sound United, LLC, Masimo Corporation and Cercacor Laboratories, Inc.* v. *Apple Inc.*, Case No. 1:22-cv-01378-MN, 7 pages.
Mar. 16, 2024 Joint Letter for Mar. 20, 2024 Case Management Conference, *Apple Inc.* v. *Masimo Corporation and Sound United, LLC, Masimo Corporation and Cercacor Laboratories, Inc.* v. *Apple Inc.*, Case No. 1:22-cv-01378-MN, 52 pages.
Jiang et al., "Microlenses, Properties, Fabrication and Liquid Lenses", Series in Optics and Optoelectronics, CRC Press, 2013, Ch. 1 & 4, pp. 1-9 and 71-105.
"Lens" Definition, The New Oxford American Dictionary, 2001, p. 976.
"Microlens Array—Part 1: Vocabulary", International Standard, ISO14880-1, Aug. 15, 2001, 1st Ed, pp. 22.
Stevens, R. et al., "Review of Standards for Microlenses and Microlens Arrays", The Imaging Science Journal, 2010, vol. 58, pp. 202-212.
Judgment, Appeal from the United States Patent Office, Patent Trial and Appeal Board Case No. IPR2020-01722, Federal Circuit Case Nos. 2022-1895, *Masimo Corporation* v. *Apple Inc.*, Jan. 10, 2024, in 2 pages.
Mandate, Appeal from the United States Patent Office, Patent Trial and Appeal Board Case No. IPR2020-01722, Federal Circuit Case Nos. 2022-1895, *Masimo Corporation* v. *Apple Inc.*, Feb. 16, 2024, in 1 page.
Bennett, C.A., "Principles of Physical Optics", John Wiley & Sons, Inc., Chapter 3, Reflection and Refraction, 2008, p. 8.
Li, Kejia, "Wireless Reflectance Pulse Oximeter Design and Photoplethysmographic Signal Processing", Thesis, 2010, p. 96.
Record of Oral Hearing Held Apr. 16, 2025 and Entered Jul. 8, 2025 in Inter Partes Review of U.S. Patent Nos. 10,687,743, 10,722,159 and 10,722,159 *Apple Inc.* v. *Masimo Corporation*, Inter Partes Review Nos. IPR2024-00241, IPR2024-00243 and IPR2024-00244 in 75 pages.
Patent Owner's Supplemental Brief field May 2, 2025 in Inter Partes Review of U.S. Pat. No. 10,687,743, *Apple Inc.* v. *Masimo Corporation*, Inter Partes Review No. IPR2024-00241, in 19 pages.
Declaration of Vijay K. Madisetti, Ph.D. filed Nov. 3, 2024 [Public Version] in Inter Partes Review of U.S. Pat. No. 10,722,159, *Apple Inc.* v. *Masimo Corporation*, Inter Partes Review No. IPR2024-00243, in 97 pages.
Declaration of R. James Duckworth, Ph.D, in Inter Partes Review of U.S. Pat. No. 10,687,745, *Apple Inc.* v. *Masimo Corporation*, Inter Partes Review Nos. IPR2022-01291, IPR2022-01465, dated May 20, 2023, in 89 pages.
Patent Owner Masimo Corporation's Sur-Reply, *Apple Inc.* v. *Masimo Corporation*, Inter Partes Review No. IPR2024-00241, dated Mar. 28, 2025, in 44 pages.
Masimo's Opposition to Apple's Motion to Exclude, Apple Inc. v. Masimo Corporation, Inter Partes Review No. IPR2024-00241, dated Mar. 25, 2025, in 18 pages.
Redacted Transcript of Deposition of Dr. Brian W. Anthony dated Mar. 21, 2025 in Inter Partes Review of U.S. Pat. Nos. 10,687,743, 10,722,159 and 10,722,159 *Apple Inc.* v. *Masimo Corporation*, Inter Partes Review Nos. IPR2024-00241, IPR2024-00243 and IPR2024-00244 in 211 pages.
Petitioner Demonstratives in Inter Partes Review of U.S. Patent Nos. 10,687,743, 10,722,159 and 10,722,159 *Apple Inc.* v. *Masimo Corporation*, Inter Partes Review Nos. IPR2024-00241, IPR2024-00243 and IPR2024-00244 in 146 pages.
Petitioner's Opposition to Patent Owner's Motion to Strike, *Apple Inc.* v. *Masimo Corporation*, Inter Partes Review No. IPR2024-00241, dated Mar. 17, 2025, in 13 pages.

Patent Owner Masimo's Trial Hearing Demonstratives [REDACTED Public Version], *Apple Inc.* v. *Masimo Corporation*, Inter Partes Review Nos. IPR2024-00241, IPR2024-00243 and IPR2024-00244 in 96 pages.
Petitioner's Reply in Support of Motion to Exclude, *Apple Inc.* v. *Masimo Corporation*, Inter Partes Review No. IPR2024-00241, dated Apr. 1, 2025, in 9 pages.
Patent Owner's Motion to Stike, *Apple Inc.* v. *Masimo Corporation*, Inter Partes Review No. IPR2024-00241, dated Mar. 10, 2025, in 13 pages.
Petitioner's Reply to Patent Owner's Response, *Apple Inc.* v. *Masimo Corporation*, Inter Partes Review No. IPR2024-00241, dated Feb. 14, 2025, in 46 pages.
Supplemental Declaration of R. James Duckworth, Ph.D, in Inter Partes Review of U.S. Pat. No. 10,687,743, *Apple Inc.* v. *Masimo Corporation*, Inter Partes Review Nos. IPR2024-00241+B2746, dated Feb. 13, 2025, in 77 pages.
Transcript of Deposition of Dr. Vijay Madisetti, vol. 1, *Apple Inc.* v. *Masimo Corporation*, Inter Partes Review Nos. IPR2024-00241, IPR2024-00243 and IPR2024-00244, dated Feb. 4, 2025 in 390 pages.
Transcript of Deposition of Dr. Vijay Madisetti, vol. 2, *Apple Inc.* v. *Masimo Corporation*, Inter Partes Review Nos. IPR2024-00241, IPR2024-00243 and IPR2024-00244, dated Feb. 7, 2025 in 184 pages.
Patent Owner's Response, *Apple Inc.* v. *Masimo Corporation*, Inter Partes Review No. IPR2024-00241, dated Nov. 5, 2024, in 84 pages.
Public Hearing Transcript of Brian Land, *Apple Inc.* v. *Masimo Corporation*, Inter Partes Review No. IPR2024-00241, IPR2024-00241, Filed Feb. 14, 2025 in 41 pages.
Public Hearing Transcript of Paul Mannheimer, *Apple Inc.* v. *Masimo Corporation*, Inter Partes Review No. IPR2024-00241, IPR2024-00243, IPR2024-00244, Filed Feb. 14, 2025, in 33 pages.
Public Hearing Transcript of Stepher Waydo, *Apple Inc.* v. *Masimo Corporation*, Inter Partes Review No. IPR2024-00241, IPR2024-00243, IPR2024-00244, Filed Feb. 14, 2025, in 34 pages.
Mannheimer Designations as of Jun. 5, 2022, *Apple Inc.* v. *Masimo Corporation*, Inter Partes Review No. IPR2024-00241, IPR2024-00243 in 53 pages.
Waydo Designations as of Jun. 5, 2022, *Apple Inc.* v. *Masimo Corporation*, Inter Partes Review No. IPR2024-00241, IPR2024-00243 in 44 pages.
Transcript of Deposition of Dr. Tao Shui, *Apple Inc.* v. *Masimo Corporation*, Inter Partes Review Nos. IPR2024-00241, IPR2024-00243, IPR2024-00244 dated Feb. 11, 2022 in 114 pages.
Expert Report of Majid Sarrafzadeh, Ph.D. Regarding Non-Infringement of U.S. Pat. Nos. 10,687,73 & 10,722,159, *Apple Inc.* v. *Masimo Corporation*, Inter Partes Review Nos. IPR2024-00241, dated Dec. 15, 2023 in 280 pages.
Patent Owner's Supplemental Brief field May 2, 2025 in Inter Partes Review of U.S. Pat. No. 10,722,159, *Apple Inc.* v. *Masimo Corporation*, Inter Partes Review No. IPR2024-00243, in 17 pages.
Patent Owner Masimo Corporation's Sur-Reply, *Apple Inc.* v. *Masimo Corporation*, Inter Partes Review No. IPR2024-00243, dated Mar. 28, 2025, in 43 pages.
Petitioner's Reply in Support of Motion to Exclude, *Apple Inc.* v. *Masimo Corporation*, Inter Partes Review No. IPR2024-00243, dated Apr. 1, 2025, in 9 pages.
Masimo's Opposition to Apple's Motion to Exclude, *Apple Inc.* v. *Masimo Corporation*, Inter Partes Review No. IPR2024-00243, dated Mar. 25, 2025, in 18 pages.
Petitioner's Motion to Exclude, *Apple Inc.* v. *Masimo Corporation*, Inter Partes Review No. IPR2024-00243, dated Mar. 18, 2025, in 17 pages.
Petitioner's Opposition to Patent Owner's Motion to Strike, *Apple Inc.* v. *Masimo Corporation*, Inter Partes Review No. IPR2024-00243, dated Mar. 17, 2025, in 12 pages.
Patent Owner's Motion to Stike, *Apple Inc.* v. *Masimo Corporation*, Inter Partes Review No. IPR2024-00243, dated Mar. 10, 2025, in 12 pages.
Petitioner's Reply to Patent Owner's Response, *Apple Inc.* v. *Masimo Corporation*, Inter Partes Review No. IPR2024-00243, dated Feb. 14, 2025, in 43 pages.

(56)　　　　　References Cited

OTHER PUBLICATIONS

Supplemental Declaration of Dr. Brian W. Anthony, Ph. D., in support of Petition for Inter Partes Review of U.S. Pat. No. 10,722,159, *Apple Inc.* v. *Masimo Corporation*, Inter Partes Review Nos. IPR2024-00243, IPR2024-00244 dated Feb. 13, 2025 in 96 pages.

Patent Owner's Response, *Apple Inc.* v. *Masimo Corporation*, Inter Partes Review No. IPR2024-00243, dated Nov. 5, 2024, in 83 pages.

Transcript of Deposition of Dr. Brian W. Anthony dated Oct. 28, 2024 in Inter Partes Review of U.S. Pa. Nos. 10,687,743, 10,722,159 and 10,722,159 *Apple Inc.* v. *Masimo Corporation*, Inter Partes Review Nos. IPR2024-00241, IPR2024-00243 and IPR2024-00244 in 162 pages.

Patent Owner's Supplemental Brief field May 2, 2025 in Inter Partes Review of U.S. Pat. No. 10,722,159, *Apple Inc.* v. *Masimo Corporation*, Inter Partes Review No. IPR2024-00244, in 15 pages.

Patent Owner Masimo Corporation's Sur-Reply, *Apple Inc.* v. *Masimo Corporation*, Inter Partes Review No. IPR2024-00244, dated Mar. 28, 2025, in 42 pages.

Petitioner's Reply in Support of Motion to Exclude, *Apple Inc.* v. *Masimo Corporation*, Inter Partes Review No. IPR2024-00244, dated Apr. 1, 2025, in 9 pages.

Masimo's Opposition to Apple's Motion to Exclude, *Apple Inc.* v. *Masimo Corporation*, Inter Partes Review No. IPR2024-00244, dated Mar. 25, 2025, in 18 pages.

Petitioner's Motion to Exclude, *Apple Inc.* v. *Masimo Corporation*, Inter Partes Review No. IPR2024-00244, dated Mar. 18, 2025, in 17 pages.

Petitioner's Opposition to Patent Owner's Motion to Strike, *Apple Inc.* v. *Masimo Corporation*, Inter Partes Review No. IPR2024-00244, dated Mar. 17, 2025, in 11 pages.

Patent Owner's Motion to Stike, *Apple Inc.* v. *Masimo Corporation*, Inter Partes Review No. IPR2024-00244, dated Mar. 10, 2025, in 11 pages.

Petitioner's Reply to Patent Owner's Response, *Apple Inc.* v. *Masimo Corporation*, Inter Partes Review No. IPR2024-00244, dated Feb. 14, 2025, in 44 pages.

Patent Owner's Response, *Apple Inc.* v. *Masimo Corporation*, Inter Partes Review No. IPR2024-00244, dated Nov. 5, 2024, in 83 pages.

Declaration of Vijay K. Madisetti, Ph.D. filed Nov. 3, 2024 [Public Version] in Inter Partes Review of U.S. Pat. No. 10,722,159, *Apple Inc.* v. *Masimo Corporation*, Inter Partes Review No. IPR2024-00244, in 85 pages.

Judgment, Final Written Decision Determining No Challenged Claims Unpatentable, DismissingPetitioner's Motion to Exclude and Patent Owner's Motion to Strike, Granting Petitioner's Motions to Seal, *Apple Inc.* v. *Masimo Corporation*, Inter Partes Review No. IPR2024-00244, Jul. 8, 2025, in 46 pages.

Judgment, Final Written Decision Determining Some Challenged Claims Unpatentable, Dismissing Petitioner's Motion to Exclude and Patent Owner's Motion to Strike, Granting Petitioner's Motions to Seal, *Apple Inc.* v. *Masimo Corporation*, Inter Partes Review No. IPR2024-00241, Jul. 8, 2025, in 111 pages.

Judgment, Final Written Decision Determining Some Challenged Claims Unpatentable, DismissingPetitioner's Motion to Exclude and Patent Owner's Motion to Strike, Granting Petitioner's Motions to Seal, *Apple Inc.* v. *Masimo Corporation*, Inter Partes Review No. IPR2024-00243, Jul. 8, 2025, in 101 pages.

Patent Owner's Notice of Appeal to the United States Court of Appeals for the Federal Circuit, *Apple Inc.* v. *Masimo Corporation*, Inter Partes Review No. IPR2024-00241, Filed Sep. 9, 2025, in 4 pages.

Patent Owner's Notice of Appeal to the United States Court of Appeals for the Federal Circuit, *Apple Inc.* v. *Masimo Corporation*, Inter Partes Review No. IPR2024-00243, Filed Sep. 9, 2025, in 4 pages.

Record of Oral Hearing held Apr. 16, 2025, Inter Partes Review Nos. IPR2024-00241, IPR2024-00243, IPR2024-00244, in 38 pages.

FIG. I

PHYSIOLOGICAL MEASUREMENT DEVICES, SYSTEMS, AND METHODS

INCORPORATION BY REFERENCE TO ANY PRIORITY APPLICATIONS

The present application is a continuation of U.S. patent application Ser. No. 16/871,874, filed May 11, 2020, which is a continuation of U.S. patent application Ser. No. 16/835, 712, filed Mar. 31, 2020, which is a continuation of U.S. patent application Ser. No. 16/791,955, filed Feb. 14, 2020, which is a continuation of U.S. patent application Ser. No. 16/532,061 filed Aug. 5, 2019, which is a continuation of U.S. patent application Ser. No. 15/195,199 filed Jun. 28, 2016, which claims priority benefit under 35 U.S.C. § 119(e) from U.S. Provisional Application No. 62/188,430, filed Jul. 2, 2015, which is incorporated by reference herein. Any and all applications for which a foreign or domestic priority claim is identified in the Application Data Sheet as filed with the present application are hereby incorporated by reference under 37 CFR 1.57.

FIELD OF THE DISCLOSURE

The present disclosure relates to the field of non-invasive optical-based physiological monitoring sensors, and more particularly to systems, devices and methods for improving the non-invasive measurement accuracy of oxygen saturation, among other physiological parameters.

BACKGROUND

Spectroscopy is a common technique for measuring the concentration of organic and some inorganic constituents of a solution. The theoretical basis of this technique is the Beer-Lambert law, which states that the concentration $c_i$ of an absorbent in solution can be determined by the intensity of light transmitted through the solution, knowing the pathlength $d_\lambda$, the intensity of the incident light $I_{0,\lambda}$, and the extinction coefficient $\varepsilon_{i,\lambda}$, at a particular wavelength $\lambda$.

In generalized form, the Beer-Lambert law is expressed as:

$$I_\lambda = I_{0,\lambda} e^{-d_\lambda \cdot \mu_{a,\lambda}} \tag{1}$$

$$\mu_{a,\lambda} = \sum_{i=1}^{n} \varepsilon_{i,\lambda} \cdot c_i \tag{2}$$

where $\mu_{\alpha,\lambda}$ is the bulk absorption coefficient and represents the probability of absorption per unit length. The minimum number of discrete wavelengths that are required to solve equations 1 and 2 is the number of significant absorbers that are present in the solution.

A practical application of this technique is pulse oximetry, which utilizes a noninvasive sensor to measure oxygen saturation and pulse rate, among other physiological parameters. Pulse oximetry relies on a sensor attached externally to the patient to output signals indicative of various physiological parameters, such as a patient's blood constituents and/or analytes, including for example a percent value for arterial oxygen saturation, among other physiological parameters. The sensor has an emitter that transmits optical radiation of one or more wavelengths into a tissue site and a detector that responds to the intensity of the optical radiation after absorption by pulsatile arterial blood flowing within the tissue site. Based upon this response, a processor determines the relative concentrations of oxygenated hemoglobin ($HbO_2$) and deoxygenated hemoglobin (Hb) in the blood so as to derive oxygen saturation, which can provide early detection of potentially hazardous decreases in a patient's oxygen supply.

A pulse oximetry system generally includes a patient monitor, a communications medium such as a cable, and/or a physiological sensor having one or more light emitters and a detector, such as one or more light-emitting diodes (LEDs) and a photodetector. The sensor is attached to a tissue site, such as a finger, toe, earlobe, nose, hand, foot, or other site having pulsatile blood flow which can be penetrated by light from the one or more emitters. The detector is responsive to the emitted light after attenuation or reflection by pulsatile blood flowing in the tissue site. The detector outputs a detector signal to the monitor over the communication medium. The monitor processes the signal to provide a numerical readout of physiological parameters such as oxygen saturation (SpO2) and/or pulse rate. A pulse oximetry sensor is described in U.S. Pat. No. 6,088,607 entitled *Low Noise Optical Probe*; pulse oximetry signal processing is described in U.S. Pat. Nos. 6,650,917 and 6,699,194 entitled *Signal Processing Apparatus and Signal Processing Apparatus and Method*, respectively; a pulse oximeter monitor is described in U.S. Pat. No. 6,584,336 entitled *Universal/ Upgrading Pulse Oximeter*; all of which are assigned to Masimo Corporation, Irvine, CA, and each is incorporated by reference herein in its entirety.

There are many sources of measurement error introduced to pulse oximetry systems. Some such sources of error include the pulse oximetry system's electronic components, including emitters and detectors, as well as chemical and structural physiological differences between patients. Another source of measurement error is the effect of multiple scattering of photons as the photons pass through the patient's tissue (arterial blood) and arrive at the sensor's light detector.

SUMMARY

This disclosure describes embodiments of non-invasive methods, devices, and systems for measuring blood constituents, analytes, and/or substances such as, by way of non-limiting example, oxygen, carboxyhemoglobin, methemoglobin, total hemoglobin, glucose, proteins, lipids, a percentage thereof (e.g., saturation), pulse rate, perfusion index, oxygen content, total hemoglobin, Oxygen Reserve Index™ (ORI™) or for measuring many other physiologically relevant patient characteristics. These characteristics can relate to, for example, pulse rate, hydration, trending information and analysis, and the like.

In an embodiment, an optical physiological measurement system includes an emitter configured to emit light of one or more wavelengths. The system also includes a diffuser configured to receive the emitted light, to spread the received light, and to emit the spread light over a larger tissue area than would otherwise be penetrated by the emitter directly emitting light at a tissue measurement site. The tissue measurement site can include, such as, for example, a finger, a wrist, or the like. The system further includes a concentrator configured to receive the spread light after it has been attenuated by or reflected from the tissue measurement site. The concentrator is also configured to collect and concentrate the received light and to emit the concentrated light to a detector. The detector is configured to detect the concentrated light and to transmit a signal indicative of the detected light. The system also includes a processor configured to receive the transmitted signal indicative of the detected light and to determine, based on an amount of absorption, an analyte of interest, such as, for example, arterial oxygen saturation or other parameter, in the tissue measurement site.

In certain embodiments of the present disclosure, the diffuser comprises glass, ground glass, glass beads, opal glass, or a microlens-based, band-limited, engineered diffuser that can deliver efficient and uniform illumination. In some embodiments the diffuser is further configured to define a surface area shape by which the emitted spread light is distributed onto a surface of the tissue measurement site. The defined surface area shape can include, by way of non-limiting example, a shape that is substantially rectangular, square, circular, oval, or annular, among others.

According to some embodiments, the optical physiological measurement system includes an optical filter having a light-absorbing surface that faces the tissue measurement site. The optical filter also has an opening that is configured to allow the spread light, after being attenuated by the tissue measurement site, to be received by the concentrator. In an embodiment, the opening has dimensions, wherein the dimensions of the opening are similar to the defined surface area shape by which the emitted spread light is distributed onto the surface of the tissue measurement site. In an embodiment, the opening has dimensions that are larger than the defined surface area shape by which the emitted spread light is distributed onto the surface of the tissue measurement site. In other embodiments, the dimensions of the opening in the optical filter are not the same as the diffuser opening, but the dimensions are larger than the detector package.

In other embodiments of the present disclosure, the concentrator comprises glass, ground glass, glass beads, opal glass, or a compound parabolic concentrator. In some embodiments the concentrator comprises a cylindrical structure having a truncated circular conical structure on top. The truncated section is adjacent the detector. The light concentrator is structured to receive the emitted optical radiation, after reflection by the tissue measurement site, and to direct the reflected light to the detector.

In accordance with certain embodiments of the present disclosure, the processor is configured to determine an average level of the light detected by the detector. The average level of light is used to determine a physiological parameter in the tissue measurement site.

According to another embodiment, a method to determine a constituent or analyte in a patient's blood is disclosed. The method includes emitting, from an emitter, light of at least one wavelength; spreading, with a diffuser, the emitted light and emitting the spread light from the diffuser to a tissue measurement site; receiving, by a concentrator, the spread light after the spread light has been attenuated by the tissue measurement site; concentrating, by the concentrator, the received light and emitting the concentrated light from the concentrator to a detector; detecting, with the detector, the emitted concentrated light; transmitting, from the detector, a signal responsive to the detected light; receiving, by a processor, the transmitted signal responsive to the detected light; and processing, by the processor, the received signal responsive to the detected light to determine a physiological parameter.

In some embodiments, the method to determine a constituent or analyte in a patient's blood includes filtering, with a light-absorbing detector filter, scattered portions of the emitted spread light. According to an embodiment, the light-absorbing detector filter is substantially rectangular in shape and has outer dimensions in the range of approximately 1-5 cm in width and approximately 2-8 cm in length, and has an opening through which emitted light may pass, the opening having dimensions in the range of approximately 0.25-3 cm in width and approximately 1-7 cm in length. In another embodiment, the light-absorbing detector filter is substantially square in shape and has outer dimensions in the range of approximately 0.25-10 cm$^2$, and has an opening through which emitted light may pass, the opening having dimensions in the range of approximately 0.1-8 cm$^2$. In yet another embodiment, the light-absorbing detector filter is substantially rectangular in shape and has outer dimensions of approximately 3 cm in width and approximately 6 cm in length, and has an opening through which emitted light may pass, the opening having dimensions of approximately 1.5 cm in width and approximately 4 cm in length.

In still other embodiments of the method to determine a constituent or analyte in a patient's blood, spreading, with a diffuser, the emitted light and emitting the spread light from the diffuser to a tissue measurement site is performed by at least one of a glass diffuser, a ground glass diffuser, a glass bead diffuser, an opal glass diffuser, and an engineered diffuser. In some embodiments the emitted spread light is emitted with a substantially uniform intensity profile. And in some embodiments, emitting the spread light from the diffuser to the tissue measurement site includes spreading the emitted light so as to define a surface area shape by which the emitted spread light is distributed onto a surface of the tissue measurement site.

According to yet another embodiment, a pulse oximeter is disclosed. The pulse oximeter includes an emitter configured to emit light at one or more wavelengths. The pulse oximeter also includes a diffuser configured to receive the emitted light, to spread the received light, and to emit the spread light directed at a tissue measurement sight. The pulse oximeter also includes a detector configured to detect the emitted spread light after being attenuated by or reflected from the tissue measurement site and to transmit a signal indicative of the detected light. The pulse oximeter also includes a processor configured to receive the transmitted signal and to process the received signal to determine an average absorbance of a blood constituent or analyte in the tissue measurement site over a larger measurement site area than can be performed with a point light source or point detector. In some embodiments, the diffuser is further configured to define a surface area shape by which the emitted spread light is distributed onto a surface of the tissue measurement site, and the detector is further configured to have a detection area corresponding to the defined surface area shape by which the emitted spread light is distributed onto the surface of the tissue measurement site. According to some embodiments, the detector comprises an array of detectors configured to cover the detection area. In still other embodiments, the processor is further configured to determine an average of the detected light.

For purposes of summarizing, certain aspects, advantages and novel features of the disclosure have been described herein. It is to be understood that not necessarily all such advantages can be achieved in accordance with any particular embodiment of the systems, devices and/or methods disclosed herein. Thus, the subject matter of the disclosure herein can be embodied or carried out in a manner that achieves or optimizes one advantage or group of advantages as taught herein without necessarily achieving other advantages as can be taught or suggested herein.

BRIEF DESCRIPTION OF THE DRAWINGS

Throughout the drawings, reference numbers can be re-used to indicate correspondence between referenced elements. The drawings are provided to illustrate embodiments of the disclosure described herein and not to limit the scope thereof.

FIG. 1 illustrates a conventional approach to two-dimensional pulse oximetry in which the emitter is configured to emit optical radiation as a point optical source.

DETAILED DESCRIPTION

FIG. 1 illustrates schematically a conventional pulse oximetry sensor having a two-dimensional (2D) approach to pulse oximetry. As illustrated, the emitter 104 is configured to emit optical radiation as a point optical source, i.e., an optical radiation source that has negligible dimensions such that it may be considered as a point. This approach is referred to herein as "two-dimensional" pulse oximetry because it applies a two-dimensional analytical model to the three-dimensional space of the tissue measurement site 102 of the patient. Point optical sources feature a defined, freely selectable, and homogeneous light beam area. Light beams emitted from LED point sources often exhibit a strong focus which can produce a usually sharply-defined and evenly-lit illuminated spot often with high intensity dynamics. Illustratively, when looking at the surface of the tissue measurement site 102 (or "sample tissue"), which in this example is a finger, a small point-like surface area of tissue 204 is irradiated by a point optical source. In some embodiments, the irradiated circular area of the point optical source is in the range between 8 and 150 microns. Illustratively, the emitted point optical source of light enters the tissue measurement site 102 as a point of light. As the light penetrates the depth of the tissue 102, it does so as a line or vector, representing a two-dimensional construct within a three-dimensional structure, namely the patient's tissue 102.

Use of a point optical source is believed to reduce variability in light pathlength which would lead to more accurate oximetry measurements. However, in practice, photons do not travel in straight paths. Instead, the light particles scatter, bouncing around between various irregular objects (such as, for example, red blood cells) in the patient's blood. Accordingly, photon pathlengths vary depending on, among other things, their particular journeys through and around the tissue at the measurement site 102. This phenomenon is referred to as "multiple scattering." In a study, the effects of multiple scattering were examined by comparing the results of photon diffusion analysis with those obtained using an analysis based on the Beer-Lambert law, which neglects multiple scattering in the determination of light pathlength. The study found that that the difference between the average lengths of the paths traveled by red and infrared photons makes the oximeter's calibration curve (based on measurements obtained from normal subjects) sensitive to the total attenuation coefficients of the tissue in the two wavelength bands used for pulse oximetry, as well as to absorption by the pulsating arterial blood.

Figure 2:
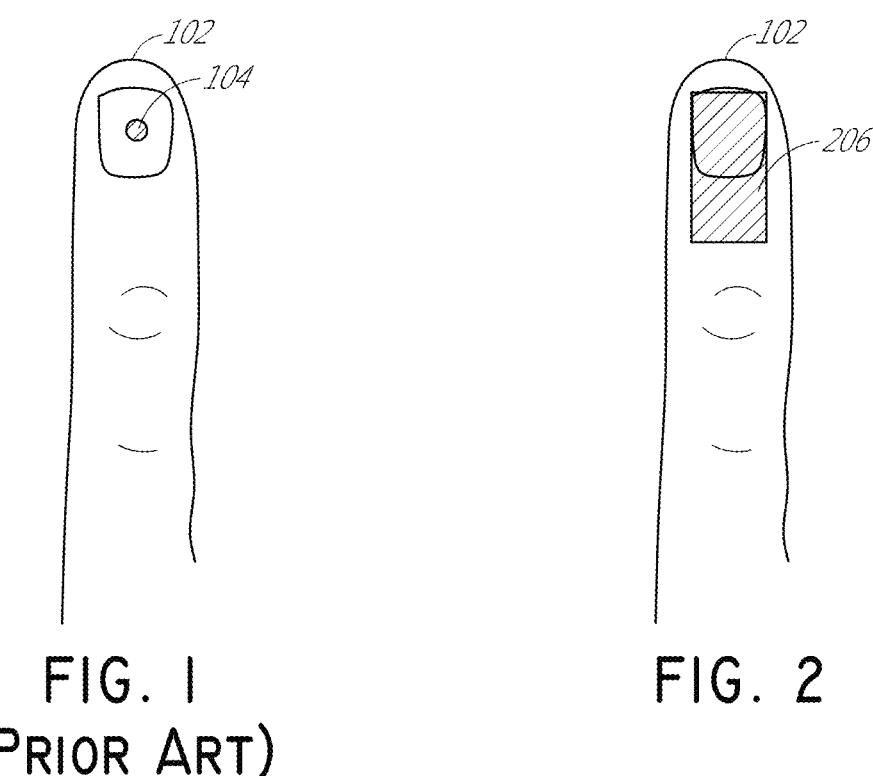
FIG. 2 illustrates the disclosed three-dimensional approach to pulse oximetry in which the emitted light irradiates a substantially larger volume of tissue as compared to the point source approach described with respect to FIG. 1.

FIG. 2 illustrates schematically the disclosed systems, devices, and methods to implement three-dimensional (3D) pulse oximetry in which the emitted light irradiates a larger volume of tissue at the measurement site 102 as compared to the 2D point optical source approach described with respect to FIG. 1. In an embodiment, again looking at the surface of the tissue measurement site 102, the irradiated surface area 206 of the measurement site 102 is substantially rectangular in shape with dimensions in the range of approximately 0.25-3 cm in width and approximately 1-6 cm in length. In another embodiment, the irradiated surface area 206 of the measurement site 102 is substantially rectangular in shape and has dimensions of approximately 1.5 cm in width and approximately 2 cm in length. In another embodiment, the irradiated surface area 206 of the measurement site 102 is substantially rectangular in shape and has dimensions of approximately 0.5 cm in width and approximately 1 cm in length. In another embodiment, the irradiated surface area 206 of the measurement site 102 is substantially rectangular in shape has dimensions of approximately 1 cm in width and approximately 1.5 cm in length. In yet another embodiment, the irradiated surface area 206 of the measurement site 102 is substantially square in shape and has dimensions in a range of approximately 0.25-9 cm$^2$. In certain embodiments, the irradiated surface area 206 of the measurement site 102 is within a range of approximately 0.5-2 cm in width, and approximately 1-4 cm in length. Of course a skilled artisan will appreciate that many other shapes and dimensions of irradiated surface area 206 can be used. Advantageously, by irradiating the tissue measurement site 102 with a surface area 206, the presently disclosed systems, devices, and methods apply a three-dimensional analytical model to the three-dimensional structure being measured, namely, the patient's sample tissue 102.

According to the Beer-Lambert law, the amount of light absorbed by a substance is proportional to the concentration of the light-absorbing substance in the irradiated solution (i.e., arterial blood). Advantageously, by irradiating a larger volume of tissue 102, a larger sample size of light attenuated (or reflected) by the tissue 102 is measured. The larger, 3D sample provides a data set that is more representative of the complete interaction of the emitted light as it passes through the patient's blood as compared to the 2D point source approach described above with respect to FIG. 1. By taking an average of the detected light, as detected over a surface area substantially larger than a single point, the disclosed pulse oximetry systems, devices, and methods will yield a more accurate measurement of the emitted light absorbed by the tissue, which will lead to a more accurate oxygen saturation measurement.

Figure 3:
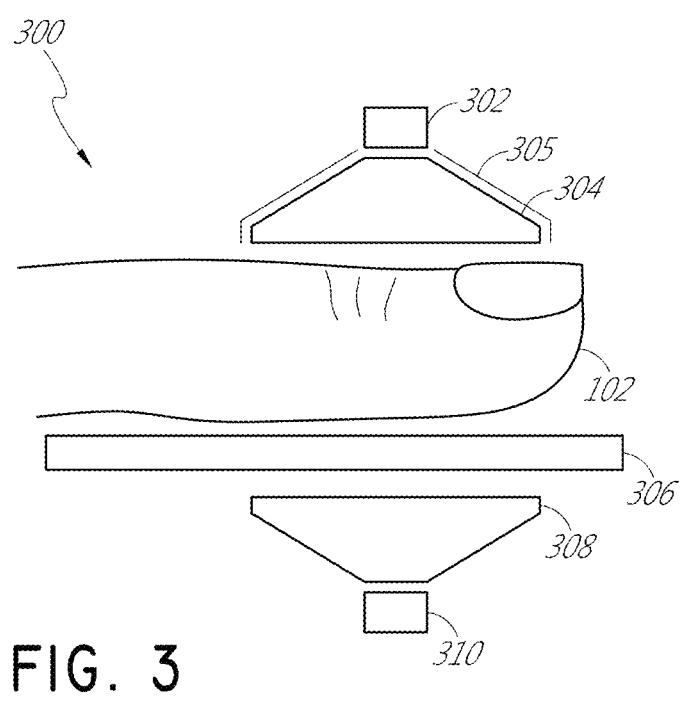
FIG. 3 illustrates schematically a side view of a three-dimensional pulse oximetry sensor according to an embodiment of the present disclosure.

FIG. 3 illustrates schematically a side view of a pulse oximetry 3D sensor 300 according to an embodiment of the present disclosure. In the illustrated embodiment, the 3D sensor 300 irradiates the tissue measurement site 102 and detects the emitted light, after being attenuated by the tissue measurement site 102. In other embodiments, for example, as describe below with respect to FIGS. 7A and 7B, the 3D sensor 300 can be arranged to detect light that is reflected by the tissue measurement site 102. The 3D sensor 300 includes an emitter 302, a light diffuser 304, a light-absorbing detector filter 306, a light concentrator 308, and a detector 310. In some optional embodiments, the 3D sensor 300 further includes a reflector 305. The reflector 305 can be a metallic reflector or other type of reflector. Reflector 305 can be a coating, film, layer or other type of reflector. The reflector 305 can serve as a reflector to prevent emitted light from emitting out of a top portion of the light diffuser 304 such that light from the emitter 302 is directed in the tissue rather than escaping out of a side or top of the light diffuser 304. Additionally, the reflector 305 can prevent ambient light from entering the diffuser 304 which might ultimately cause errors within the detected light. The reflector 305 also prevent light piping that might occur if light from the detector 302 is able to escape from the light diffuser 304 and be pipped around a sensor securement mechanism to detector 310 without passing through the patient's tissue 102.

The emitter 302 can serve as the source of optical radiation transmitted towards the tissue measurement site 102. The emitter 302 can include one or more sources of optical radiation, such as LEDs, laser diodes, incandescent bulbs with appropriate frequency-selective filters, combinations of the same, or the like. In an embodiment, the emitter 302 includes sets of optical sources that are capable of emitting visible and near-infrared optical radiation. In some embodiments, the emitter 302 transmits optical radiation of red and infrared wavelengths, at approximately 650 nm and approximately 940 nm, respectively. In some embodiments, the emitter 302 includes a single source optical radiation.

The light diffuser 304 receives the optical radiation emitted from the emitter 302 and spreads the optical radiation over an area, such as the area 206 depicted in FIG. 2. In some embodiments, the light diffuser 304 is a beam shaper that can homogenize the input light beam from the emitter 302, shape the output intensity profile of the received light, and define the way (e.g., the shape or pattern) the emitted light is distributed to the tissue measurement site 102. Examples of materials that can be used to realize the light diffuser 304 include, without limitation, a white surface, glass, ground glass, glass beads, polytetrafluoroethylene also known as Teflon®, opal glass, and greyed glass, to name a few. Additionally, engineered diffusers can be used to realize the diffuser 304 by providing customized light shaping with respect to intensity and distribution. Such diffusers can, for example, deliver substantially uniform illumination over a specified target area (such as, for example, irradiated surface area 206) in an energy-efficient manner. Examples of engineered diffusers can include molded plastics with specific shapes, patterns or textures designed to diffuse the emitter light across the entirety of the patient's tissue surface.

Advantageously, the diffuser 304 can receive emitted light in the form of a point optical source and spread the light to fit a desired surface area on a plane defined by the surface of the tissue measurement site 102. In an embodiment, the diffuser 304 is made of ground glass which spreads the emitted light with a Gaussian intensity profile. In another embodiment the diffuser 304 includes glass beads. In some embodiments, the diffuser 304 is constructed so as to diffuse the emitted light in a Lambertian pattern. A Lambertian pattern is one in which the radiation intensity is substantially constant throughout the area of dispersion. One such diffuser 304 is made from opal glass. Opal glass is similar to ground glass, but has one surface coated with a milky white coating to diffuse light evenly. In an embodiment, the diffuser 304 is capable of distributing the emitted light on the surface of a plane (e.g., the surface of the tissue measurement site 102) in a predefined geometry (e.g., a rectangle, square, or circle), and with a substantially uniform intensity profile and energy distribution. In some embodiments, the efficiency, or the amount of light transmitted by the diffuser 304, is greater than 70% of the light emitted by the emitter 302. In some embodiments, the efficiency is greater than 90% of the emitted light. Other optical elements known in the art may be used for the diffuser 304.

In an embodiment, the diffuser 304 has a substantially rectangular shape having dimensions within a range of approximately 0.5-2 cm in width and approximately 1-4 centimeters in length. In another embodiment, the substantially rectangular shape of the diffuser 304 has dimensions of approximately 0.5 cm in width and approximately 1 cm in length. In another embodiment, the diffuser's 304 substantially rectangular shape has dimensions of approximately 1 cm in width and approximately 1.5 cm in length. In yet another embodiment, the diffuser 304 has a substantially square shape with dimensions in the range of approximately 0.25-10 cm².

Figure 4A:
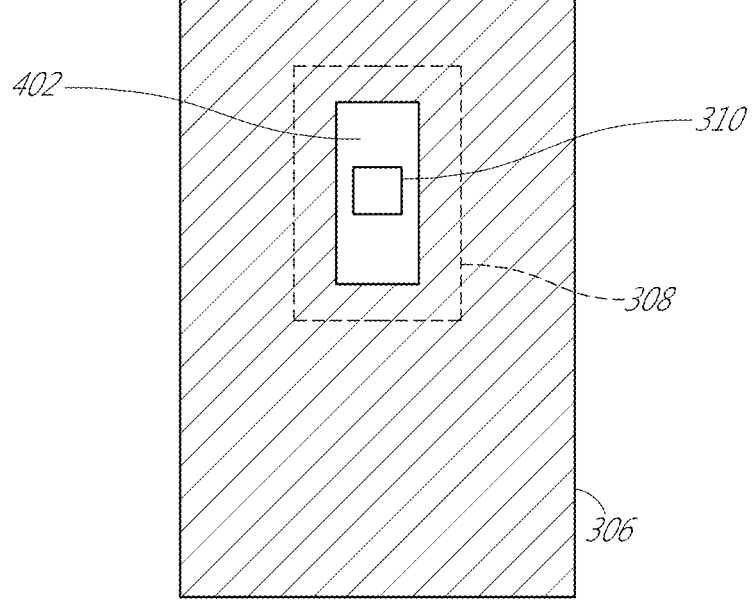
FIG. 4A is a top view of a portion of a three-dimensional pulse oximetry sensor according to an embodiment of the present disclosure.

The light-absorbing detector filter 306, which is also depicted in FIG. 4A in a top view, is a planar surface having an opening 402 through which the emitted light may pass after being attenuated by the tissue measurement site 102. In the depicted embodiment, the opening 402 is rectangular-shaped, with dimensions substantially similar to the irradiated surface area 206. According to an embodiment, the light-absorbing detector filter is substantially rectangular in shape and has outer dimensions of 4 cm in width and 8 cm in length, and has an opening through which emitted light may pass, the opening having dimensions of 2 cm in width and 5 cm in length. In another embodiment, the light-absorbing detector filter is substantially rectangular in shape and has outer dimensions in the range of 1-3 cm in width and 2-8 cm in length, and has an opening through which emitted light may pass, the opening having dimensions in the range of 0.25-2 cm in width and 1-4 cm in length. In yet another embodiment, the light-absorbing detector filter is substantially rectangular in shape and has outer dimensions of 3 cm in width and 6 cm in length, and has an opening through which emitted light may pass, the opening having dimensions of 1.5 cm in width and 4 cm in length.

The top surface of the light-absorbing filter 306 (facing the tissue measurement site 102 and the emitter 302) is coated with a material that absorbs light, such as, for example, black pigment. Many other types of light-absorbing materials are well known in the art and can be used with the detector filter 306. During operation, light emitted from the emitter 302 can reflect off of the tissue measurement site 102 (or other structures within the 3D sensor 300) to neighboring portions of the 3D sensor 300. If those neighboring portions of the 3D sensor 300 possess reflective surfaces, then the light can reflect back to the tissue measurement site 102, progress through the tissue and arrive at the detector 310. Such multiple scattering can result in detecting photons whose pathlengths are considerably longer than most of the light that is detected, thereby introducing variations in pathlength which will affect the accuracy of the measurements of the pulse oximetry 3D sensor 300. Advantageously, the light-absorbing filter 306 reduces or eliminates the amount of emitted light that is reflected in this manner because it absorbs such reflected light, thereby stopping the chain of scattering events. In certain embodiments, the sensor-facing surfaces of other portions of the 3D sensor 300 are covered in light-absorbing material to further decrease the effect of reflective multiple scattering.

The light concentrator 308 is a structure to receive the emitted optical radiation, after attenuation by the tissue measurement site 102, to collect and concentrate the dispersed optical radiation, and to direct the collected and concentrated optical radiation to the detector 310. In an embodiment, the light concentrator 308 is made of ground glass or glass beads. In some embodiments, the light concentrator 308 includes a compound parabolic concentrator.

As described above with respect to FIG. 1, the detector 310 captures and measures light from the tissue measurement site 102. For example, the detector 310 can capture and measure light transmitted from the emitter 302 that has been attenuated by the tissue in the measurement site 102. The detector 310 can output a detector signal responsive to the light captured or measured. The detector 310 can be implemented using one or more photodiodes, phototransistors, or the like. In addition, a plurality of detectors 310 can be arranged in an array with a spatial configuration corresponding to the irradiated surface area 206 to capture the attenuated or reflected light from the tissue measurement site.

Figure 4B:
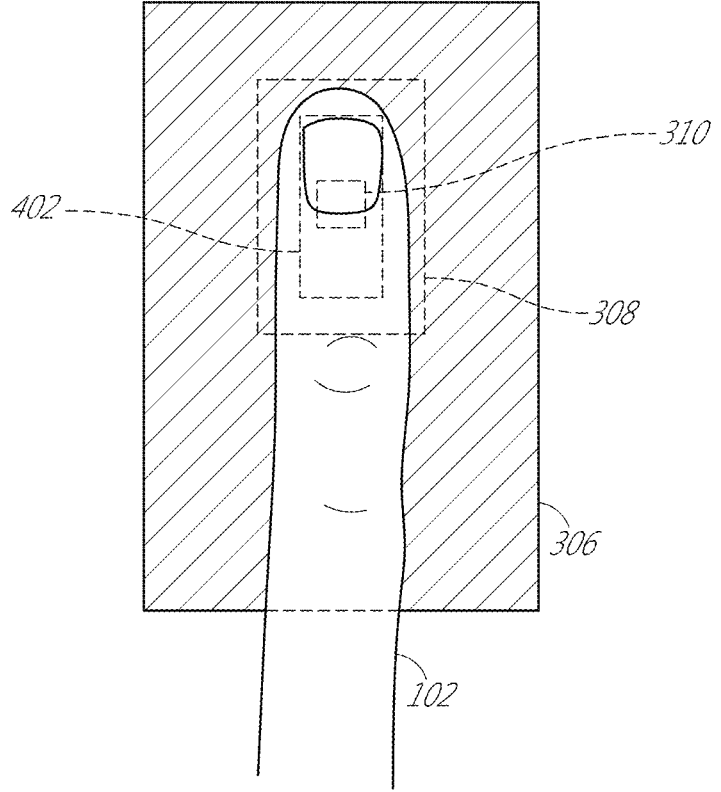
FIG. 4B illustrates the top view of a portion of the three-dimensional pulse oximetry sensor shown in FIG. 4A, with the addition of a tissue measurement site in operational position.

Referring to FIG. 4A, a top view of a portion of the 3D sensor 300 is provided. The light-absorbing detector filter 306 is illustrated having a top surface coated with a light-absorbing material. The light-absorbing material can be a black opaque material or coating or any other dark color or coating configured to absorb light. Additionally, a rectangular opening 402 is positioned relative to the light concentrator 308 (shown in phantom) and the detector 310 such that light may pass through the rectangular opening 402, into the light concentrator 308, and to the detector 310. FIG. 4B illustrates the top view of a portion of the 3D sensor 300 as in FIG. 4A, with the addition of the tissue measurement site 102 in operational position. Accordingly, the rectangular opening 402, the light concentrator 308 and the detector 310 are shown in phantom as being under the tissue measurement site 102. In FIGS. 4A and 4B, the light concentrator 308 is shown to have dimensions significantly larger than the dimensions of the rectangular opening 402. In other embodiments, the dimensions of the light concentrator 308, the rectangular opening 402, and the irradiated surface area 206 are substantially similar.

Figure 5:
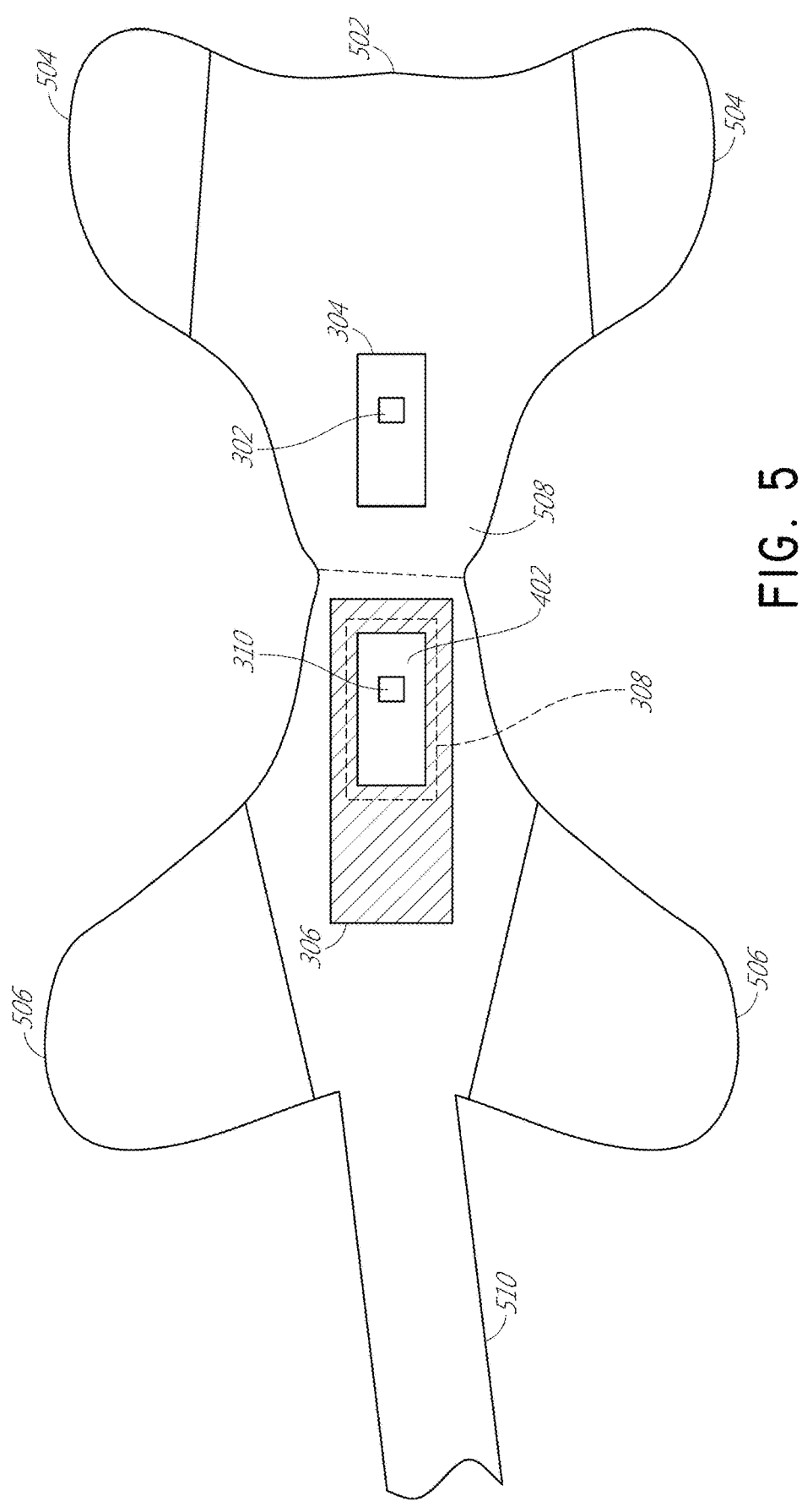
FIG. 5 illustrates a top view of a three-dimensional pulse oximetry sensor according to an embodiment of the present disclosure.

FIG. 5 illustrates a top view of a 3D pulse oximetry sensor 500 according to an embodiment of the present disclosure. The 3D sensor 500 is configured to be worn on a patient's finger 102. The 3D sensor 500 includes an adhesive substrate 502 having front flaps 504 and rear flaps 506 extending outward from a center portion 508 of the 3D sensor 500. The center portion 508 includes components of the 3D pulse oximetry sensor 300 described with respect to FIGS. 3, 4A and 4B. On the front side of the adhesive substrate 502 the emitter 302 and the light diffuser 304 are positioned. On the rear side of the adhesive substrate 502 the light-absorbent detector filter 306, the light concentrator 308 and the detector 310 are positioned. In use, the patient's finger serving as the tissue measurement site 102 is positioned over the rectangular opening 402 such that when the front portion of the adhesive substrate is folded over on top of the patient's finger 102, the emitter 302 and the light diffuser 304 are aligned with the measurement site 102, the filter 306, the light concentrator 308 and the detector 310. Once alignment is established, the front and rear flaps 504, 506 can be wrapped around the finger measurement site 102 such that the adhesive substrate 502 provides a secure contact between the patient's skin and the 3D sensor 500. FIG. 5 also illustrates an example of a sensor connector cable 510 which is used to connect the 3D sensor 500 to a monitor 809, as described with respect to FIG. 8.

Figures 6, 7A:
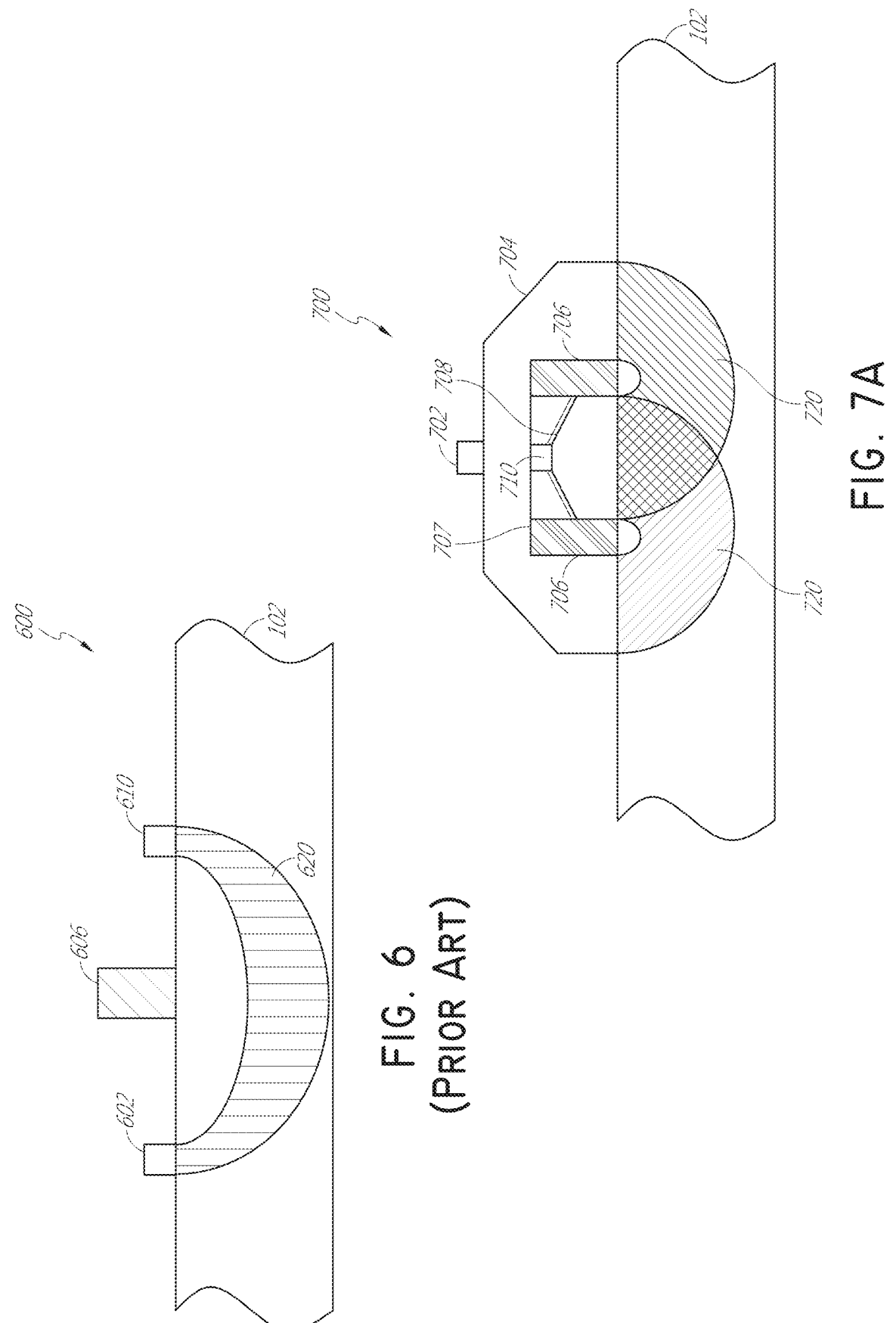
FIG. 6 illustrates a conventional two-dimensional approach to reflective pulse oximetry in which the emitter is configured to emit optical radiation as a point optical source.
FIG. 7A is a simplified schematic side view illustration of a reflective three-dimensional pulse oximetry sensor according to an embodiment of the present disclosure.

FIG. 6 is a simplified schematic illustration of a conventional, 2D approach to reflective pulse oximetry in which the emitter is configured to emit optical radiation as a point optical source. Reflective pulse oximetry is a method by which the emitter and detector are located on the same side of the tissue measurement site 102. Light is emitted into a tissue measurement site 102 and attenuated. The emitted light passes into the tissue 102 and is then reflected back to the same side of the tissue measurement site 102 as the emitter. As illustrated in FIG. 6, a depicted reflective 2D pulse oximetry sensor 600 includes an emitter 602, a light block 606, and a detector 610. The light block 606 is necessary because the emitter 602 and the detector 610 are located on the same side of the tissue measurement site 102. Accordingly, the light block 606 prevents incident emitter light, which did not enter the tissue measurement site 102, from arriving at the detector 610. The depicted 2D pulse oximetry sensor 600 is configured to emit light as a point source. As depicted in FIG. 6, a simplified illustration of the light path 620 of the emitted light from the emitter 602, through the tissue measurement site 102, and to the detector 610 is provided. Notably, a point source of light is emitted, and a point source of light is detected. As discussed above with respect to FIG. 1, use of a point optical source can result in substantial measurement error due to pathlength variability resulting from the multiple scatter phenomenon. The sample space provided by a 2D point optical emitter source is not large enough to account for pathlength variability, which will skew measurement results.

Figure 7B:
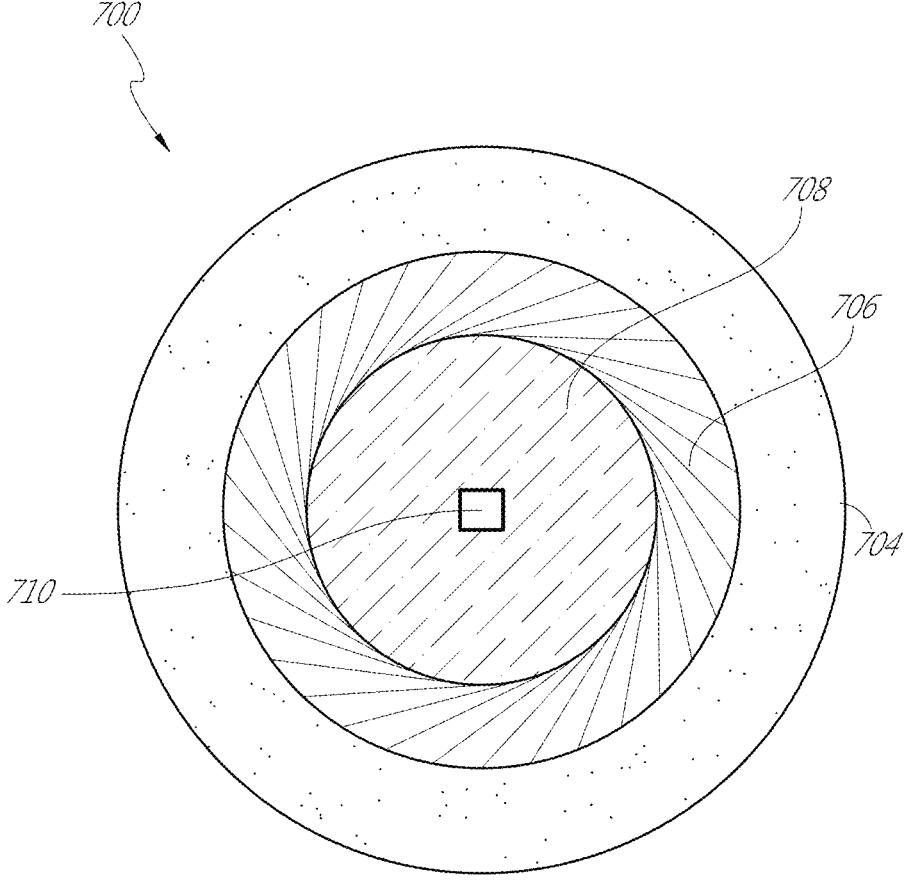
FIG. 7B is a simplified schematic top view illustration of the three-dimensional reflective pulse oximetry sensor of FIG. 7A.

FIGS. 7A and 7B are simplified schematic side and top views, respectively, of a 3D reflective pulse oximetry sensor 700 according to an embodiment of the present disclosure. In the illustrated embodiment, the 3D sensor 700 irradiates the tissue measurement site 102 and detects the emitted light that is reflected by the tissue measurement site 102. The 3D sensor 700 can be placed on a portion of the patient's body that has relatively flat surface, such as, for example a wrist, because the emitter 702 and detector 710 are on located the same side of the tissue measurement site 102. The 3D sensor 700 includes an emitter 702, a light diffuser 704, a light block 706, a light concentrator 708, and a detector 710.

As previously described, the emitter 702 can serve as the source of optical radiation transmitted towards the tissue measurement site 102. The emitter 702 can include one or more sources of optical radiation. Such sources of optical radiation can include LEDs, laser diodes, incandescent bulbs with appropriate frequency-selective filters, combinations of the same, or the like. In an embodiment, the emitter 702 includes sets of optical sources that are capable of emitting visible and near-infrared optical radiation. In some embodiments, the emitter 702 transmits optical radiation of red and infrared wavelengths, at approximately 650 nm and approximately 940 nm, respectively. In some embodiments, the emitter 702 includes a single source of optical radiation.

The light diffuser 704 receives the optical radiation emitted from the emitter 702 and homogenously spreads the optical radiation over a wide, donut-shaped area, such as the area outlined by the light diffuser 704 as depicted in FIG. 7B. Advantageously, the diffuser 704 can receive emitted light in the form of a 2D point optical source (or any other form) and spread the light to fit the desired surface area on a plane defined by the surface of the tissue measurement site 102. In an embodiment, the diffuser 704 is made of ground glass or glass beads. A skilled artisan will understand that may other materials can be used to make the light diffuser 704.

The light blocker 706 includes an annular ring having a cover portion 707 sized and shaped to form a light isolation chamber for the light concentrator 708 and the detector 710. (For purposes of illustration, the light block cover 707 is not illustrated in FIG. 7B.) The light blocker 706 and the cover 707 can be made of any material that optically isolates the light concentrator 708 and the detector 710. The light isolation chamber formed by the light blocker 706 and cover 707 ensures that the only light detected by the detector 710 is light that is reflected from the tissue measurement site.

The light concentrator 708 is a cylindrical structure with a truncated circular conical structure on top, the truncated section of which of which is adjacent the detector 710. The light concentrator 708 is structured to receive the emitted optical radiation, after reflection by the tissue measurement site 102, and to direct the reflected light to the detector 710. In an embodiment, the light concentrator 708 is made of ground glass or glass beads. In some embodiments, the light concentrator 708 includes a compound parabolic concentrator.

As previously described, the detector 710 captures and measures light from the tissue measurement site 102. For example, the detector 710 can capture and measure light transmitted from the emitter 702 that has been reflected from the tissue in the measurement site 102. The detector 710 can output a detector signal responsive to the light captured or measured. The detector 710 can be implemented using one or more photodiodes, phototransistors, or the like. In addition, a plurality of detectors 710 can be arranged in an array with a spatial configuration corresponding to the irradiated surface area depicted in FIG. 7B by the light concentrator 708 to capture the reflected light from the tissue measurement site.

Advantageously, the light path 720 illustrated in FIG. 7A depicts a substantial sample of reflected light that enter the light isolation chamber formed by the light blocker 706 and cover 707. As previously discussed, the large sample of reflected light (as compared to the reflected light collected using the 2D point optical source approach) provides the opportunity to take an average of the detected light, to derive a more accurate measurement of the emitted light absorbed by the tissue, which will lead to a more accurate oxygen saturation measurement.

Referring now to FIG. 7B, a top view of the 3D sensor 700 is illustrated with both the emitter 702 and the light blocker cover 707 removed for ease of illustration. The outer ring illustrates the footprint of the light diffuser 704. As light is emitted from the emitter 702 (not shown in FIG. 7B), it is diffused homogenously and directed to the tissue measurement site 102. The light blocker 706 forms the circular wall of a light isolation chamber to keep incident light from being sensed by the detector 710. The light blocker cover 707 blocks incidental light from entering the light isolation chamber from above. The light concentrator 710708 collects the reflected light from the tissue measurement site 102 and funnels it upward toward the detector 710 at the center of the 3D sensor 700.

Figure 8:
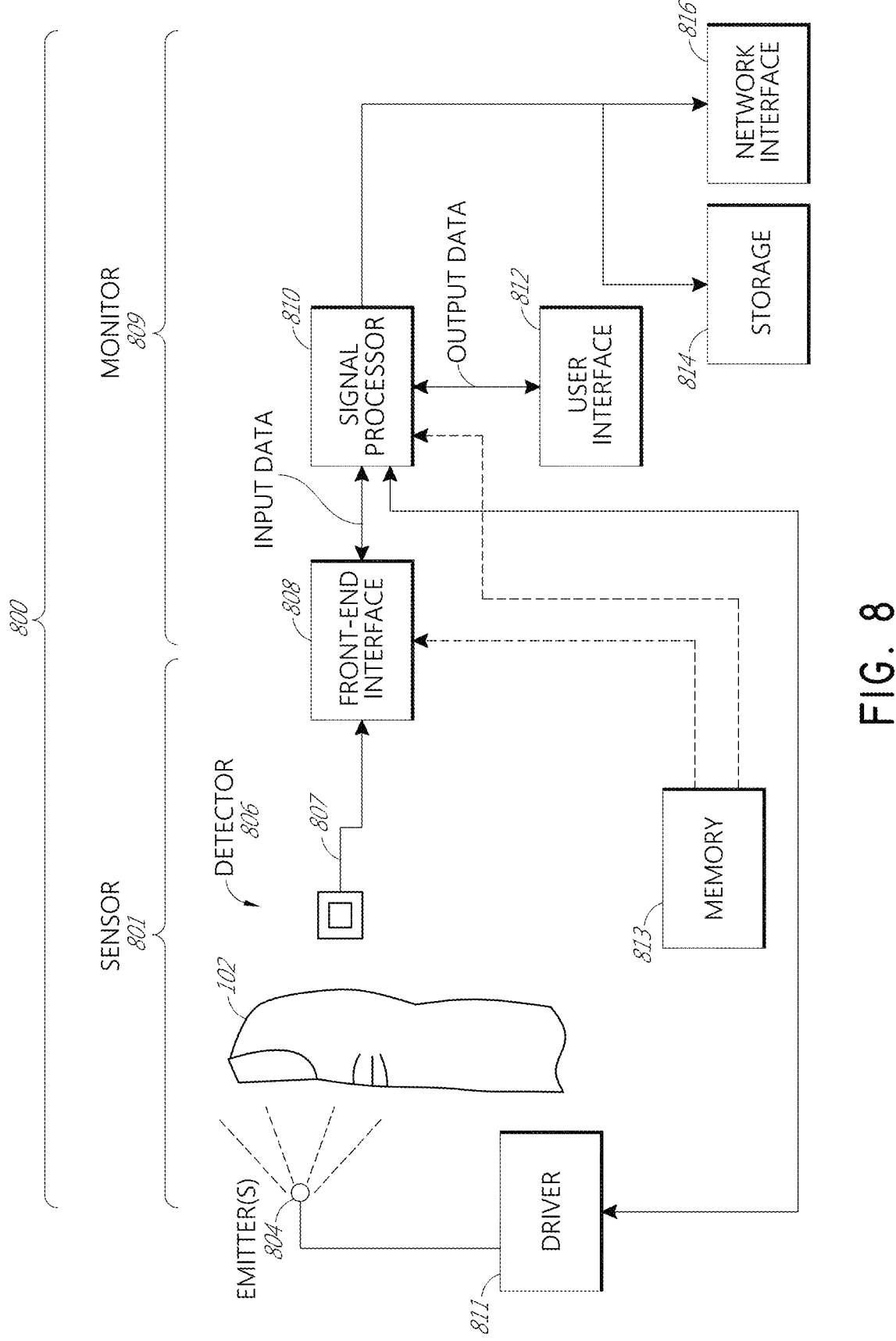
FIG. 8 illustrates a block diagram of an example pulse oximetry system capable of noninvasively measuring one or more blood analytes in a monitored patient, according to an embodiment of the disclosure.

FIG. 8 illustrates an example of an optical physiological measurement system 800, which may also be referred to herein as a pulse oximetry system 800. In certain embodiments, the pulse oximetry system 800 noninvasively measures a blood analyte, such as oxygen, carboxyhemoglobin, methemoglobin, total hemoglobin, glucose, proteins, lipids, a percentage thereof (e.g., saturation), pulse rate, perfusion index, oxygen content, total hemoglobin, Oxygen Reserve Index™ (ORI™) or many other physiologically relevant patient characteristics. These characteristics can relate to, for example, pulse rate, hydration, trending information and analysis, and the like. The system 800 can also measure additional blood analytes and/or other physiological parameters useful in determining a state or trend of wellness of a patient.

The pulse oximetry system 800 can measure analyte concentrations at least in part by detecting optical radiation attenuated by tissue at a measurement site 102. The measurement site 102 can be any location on a patient's body, such as a finger, foot, earlobe, wrist, forehead, or the like.

The pulse oximetry system 800 can include a sensor 801 (or multiple sensors) that is coupled to a processing device or physiological monitor 809. In an embodiment, the sensor 801 and the monitor 809 are integrated together into a single unit. In another embodiment, the sensor 801 and the monitor 809 are separate from each other and communicate with one another in any suitable manner, such as via a wired or wireless connection. The sensor 801 and monitor 809 can be attachable and detachable from each other for the convenience of the user or caregiver, for ease of storage, sterility issues, or the like.

In the depicted embodiment shown in FIG. 8, the sensor 801 includes an emitter 804, a detector 806, and a front-end interface 808. The emitter 804 can serve as the source of optical radiation transmitted towards measurement site 102. The emitter 804 can include one or more sources of optical radiation, such as light-emitting diodes (LEDs), laser diodes, incandescent bulbs with appropriate frequency-selective filters, combinations of the same, or the like. In an embodiment, the emitter 804 includes sets of optical sources that are capable of emitting visible and near-infrared optical radiation.

The pulse oximetry system 800 also includes a driver 811 that drives the emitter 804. The driver 111 can be a circuit or the like that is controlled by the monitor 809. For example, the driver 811 can provide pulses of current to the emitter 804. In an embodiment, the driver 811 drives the emitter 804 in a progressive fashion, such as in an alternating manner. The driver 811 can drive the emitter 804 with a series of pulses for some wavelengths that can penetrate tissue relatively well and for other wavelengths that tend to be significantly absorbed in tissue. A wide variety of other driving powers and driving methodologies can be used in various embodiments. The driver 811 can be synchronized with other parts of the sensor 801 to minimize or reduce jitter in the timing of pulses of optical radiation emitted from the emitter 804. In some embodiments, the driver 811 is capable of driving the emitter 804 to emit optical radiation in a pattern that varies by less than about 10 parts-per-million.

The detector 806 captures and measures light from the tissue measurement site 102. For example, the detector 806 can capture and measure light transmitted from the emitter 804 that has been attenuated or reflected from the tissue at the measurement site 102. The detector 806 can output a detector signal 107 responsive to the light captured and measured. The detector 806 can be implemented using one or more photodiodes, phototransistors, or the like. In some embodiments, a detector 806 is implemented in detector package to capture and measure light from the tissue measurement site 102 of the patient. The detector package can include a photodiode chip mounted to leads and enclosed in an encapsulant. In some embodiments, the dimensions of the detector package are approximately 2 square centimeters. In other embodiments, the dimensions of the detector package are approximately 1.5 centimeters in width and approximately 2 centimeters in length.

The front-end interface 808 provides an interface that adapts the output of the detectors 806, which is responsive to desired physiological parameters. For example, the front-end interface 808 can adapt the signal 807 received from the detector 806 into a form that can be processed by the monitor 809, for example, by a signal processor 810 in the monitor 809. The front-end interface 808 can have its components assembled in the sensor 801, in the monitor 809, in a connecting cabling (if used), in combinations of the same, or the like. The location of the front-end interface 808 can be chosen based on various factors including space desired for components, desired noise reductions or limits, desired heat reductions or limits, and the like.

The front-end interface 808 can be coupled to the detector 806 and to the signal processor 810 using a bus, wire, electrical or optical cable, flex circuit, or some other form of signal connection. The front-end interface 808 can also be at least partially integrated with various components, such as the detectors 806. For example, the front-end interface 808 can include one or more integrated circuits that are on the same circuit board as the detector 806. Other configurations can also be used.

As shown in FIG. 8, the monitor 909 can include the signal processor 810 and a user interface, such as a display 812. The monitor 809 can also include optional outputs alone or in combination with the display 812, such as a storage device 814 and a network interface 816. In an embodiment, the signal processor 810 includes processing logic that determines measurements for desired analytes based on the signals received from the detector 806. The signal processor 810 can be implemented using one or more microprocessors or sub-processors (e.g., cores), digital signal processors, application specific integrated circuits (ASICs), field programmable gate arrays (FPGAs), combinations of the same, and the like.

The signal processor 810 can provide various signals that control the operation of the sensor 801. For example, the signal processor 810 can provide an emitter control signal to the driver 811. This control signal can be useful in order to synchronize, minimize, or reduce jitter in the timing of pulses emitted from the emitter 804. Accordingly, this control signal can be useful in order to cause optical radiation pulses emitted from the emitter 804 to follow a precise timing and consistent pattern. For example, when a transimpedance-based front-end interface 808 is used, the control signal from the signal processor 810 can provide synchronization with an analog-to-digital converter (ADC) in order to avoid aliasing, cross-talk, and the like. As also shown, an optional memory 813 can be included in the front-end interface 808 and/or in the signal processor 810. This memory 813 can serve as a buffer or storage location for the front-end interface 808 and/or the signal processor 810, among other uses.

The user interface 812 can provide an output, e.g., on a display, for presentation to a user of the pulse oximetry system 800. The user interface 812 can be implemented as a touch-screen display, a liquid crystal display (LCD), an organic LED display, or the like. In alternative embodiments, the pulse oximetry system 800 can be provided without a user interface 812 and can simply provide an output signal to a separate display or system.

The storage device 814 and a network interface 816 represent other optional output connections that can be included in the monitor 809. The storage device 814 can include any computer-readable medium, such as a memory device, hard disk storage, EEPROM, flash drive, or the like. The various software and/or firmware applications can be stored in the storage device 814, which can be executed by the signal processor 810 or another processor of the monitor 809. The network interface 816 can be a serial bus port (RS-232/RS-485), a Universal Serial Bus (USB) port, an Ethernet port, a wireless interface (e.g., WiFi such as any 802.1x interface, including an internal wireless card), or other suitable communication device(s) that allows the monitor 809 to communicate and share data with other devices. The monitor 809 can also include various other components not shown, such as a microprocessor, graphics processor, or controller to output the user interface 812, to control data communications, to compute data trending, or to perform other operations.

Although not shown in the depicted embodiment, the pulse oximetry system 800 can include various other components or can be configured in different ways. For example, the sensor 801 can have both the emitter 804 and detector 806 on the same side of the tissue measurement site 102 and use reflectance to measure analytes.

Although the foregoing disclosure has been described in terms of certain preferred embodiments, many other variations than those described herein will be apparent to those of ordinary skill in the art.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

While the above detailed description has shown, described, and pointed out novel features as applied to various embodiments, it will be understood that various omissions, substitutions, and changes in the form and details of the systems, devices or algorithms illustrated can be made without departing from the spirit of the disclosure. As will be recognized, certain embodiments of the disclosure described herein can be embodied within a form that does not provide all of the features and benefits set forth herein, as some features can be used or practiced separately from others.

The term "and/or" herein has its broadest, least limiting meaning which is the disclosure includes A alone, B alone, both A and B together, or A or B alternatively, but does not require both A and B or require one of A or one of B. As used herein, the phrase "at least one of" A, B, "and" C should be construed to mean a logical A or B or C, using a non-exclusive logical or.

The apparatuses and methods described herein may be implemented by one or more computer programs executed by one or more processors. The computer programs include processor-executable instructions that are stored on a non-transitory tangible computer readable medium. The computer programs may also include stored data. Non-limiting examples of the non-transitory tangible computer readable medium are nonvolatile memory, magnetic storage, and optical storage. Although the foregoing disclosure has been described in terms of certain preferred embodiments, other embodiments will be apparent to those of ordinary skill in the art from the disclosure herein. Additionally, other combinations, omissions, substitutions and modifications will be apparent to the skilled artisan in view of the disclosure herein. Accordingly, the present invention is not intended to be limited by the description of the preferred embodiments, but is to be defined by reference to claims.

Additionally, all publications, patents, and patent applications mentioned in this specification are herein incorporated by reference to the same extent as if each individual publication, patent, or patent application were specifically and individually indicated to be incorporated by reference.

What is claimed is:

1. A physiological monitoring device comprising:
    an emitter comprising a set of LEDs configured to emit light;
    an engineered microlens-based material positioned between the emitter and tissue of a wrist of a user when the physiological monitoring device is attached to the user, wherein the engineered microlens-based material comprises a texture configured to change an output pattern by which light emitted by the emitter is directed toward the tissue;
    a detector configured to detect at least a portion of the light emitted from the emitter after the light is attenuated by the tissue, the detector configured to output a signal responsive to the detected light, wherein the detector and the emitter are arranged in a reflectance measurement configuration;
    a light block surrounding the detector and configured to prevent at least a portion of the light emitted from the emitter from reaching the detector without first passing through the tissue; and
    a processor configured to determine a physiological parameter of the user responsive to the signal.

2. The physiological monitoring device of claim 1, wherein the engineered microlens-based material comprises glass.

3. The physiological monitoring device of claim 1, wherein the engineered microlens-based material comprises plastic.

4. The physiological monitoring device of claim 1, wherein the detector comprises one or more photodiodes.

5. The physiological monitoring device of claim 1, wherein the physiological parameter is oxygen saturation.

6. The physiological monitoring device of claim 1, wherein the light block comprises a circular chamber surrounding the detector.

7. The physiological monitoring device of claim 1, wherein the engineered microlens-based material is aligned with the emitter about an axis that is configured to be perpendicular to the tissue when the physiological monitoring device is attached to the user.

8. The physiological monitoring device of claim 1, wherein the light block comprises a first surface and a second surface, the first surface disposed along a same plane as the detector and the second surface configured to be positioned proximate the user's wrist when the physiological monitoring device is attached to the user.

9. The physiological monitoring device of claim 8, wherein the light block comprises a height extending between the first and second surfaces, and wherein the light block is configured such that, when the physiological monitoring device is attached to the user, the height of the light block is oriented perpendicular to the tissue.

10. The physiological monitoring device of claim 1, further comprising a surface comprising a dark-colored coating, the surface configured to be positioned between the detector and the tissue when the physiological monitoring device is attached to the user, wherein a window formed in the dark-colored coating is configured to allow light reflected from the tissue to pass through the surface and to the detector.

11. The physiological monitoring device of claim 10, wherein the surface comprising the dark-colored coating is configured to be positioned against the tissue when the physiological monitoring device is attached to the user.

12. A physiological monitoring device comprising:
    an emitter comprising a set of LEDs configured to emit light;
    an engineered microlens-based material positioned between the emitter and tissue of a wrist of a user when the physiological monitoring device is attached to the user, wherein the engineered microlens-based material comprises a texture configured to change an output pattern by which light emitted by the emitter is directed toward the tissue;
    a detector configured to detect at least a portion of the light emitted from the emitter after the light is attenuated by the tissue, the detector configured to output a signal responsive to the detected light, wherein the detector and the emitter are arranged in a reflectance measurement configuration;
    a light block surrounding the detector and configured to prevent at least a portion of the light emitted from the emitter from reaching the detector without first passing through the tissue, wherein at least a portion of an end of the light block is configured to be positioned proximate skin of the user proximate the tissue when the physiological monitoring device is attached to the user; and
    a processor configured to determine a physiological parameter of the user responsive to the signal.

13. The physiological monitoring device of claim 12, wherein the engineered microlens-based material comprises glass.

14. The physiological monitoring device of claim 12, wherein the engineered microlens-based material comprises plastic.

15. The physiological monitoring device of claim 12, wherein the detector comprises one or more photodiodes.

16. The physiological monitoring device of claim 12, wherein the physiological parameter is oxygen saturation.

17. The physiological monitoring device of claim 12, wherein the light block comprises a circular chamber surrounding the detector.

18. The physiological monitoring device of claim 12, wherein the engineered microlens-based material is aligned with the emitter about an axis that is configured to be perpendicular to the tissue when the physiological monitoring device is attached to the user.

19. The physiological monitoring device of claim 12, wherein the light block comprises a first surface and a second surface, the first surface disposed along a same plane as the detector and the second surface configured to be positioned proximate the user's wrist when the physiological monitoring device is attached to the user.

20. The physiological monitoring device of claim 19, wherein the light block comprises a height extending between the first and second surfaces, and wherein the light block is configured such that, when the physiological monitoring device is attached to the user, the height of the light block is oriented perpendicular to the tissue.

21. The physiological monitoring device of claim 12, further comprising a surface comprising a dark-colored coating, the surface configured to be positioned between the detector and the tissue when the physiological monitoring device is attached to the user, wherein an opening formed in the dark-colored coating is configured to allow light reflected from the tissue to pass through the surface and to the detector.

22. The physiological monitoring device of claim 21, wherein the surface comprising the dark-colored coating is configured to be positioned against the tissue when the physiological monitoring device is attached to the user.

* * * * *